United States Patent
Kwon et al.

(10) Patent No.: US 12,331,116 B2
(45) Date of Patent: *Jun. 17, 2025

(54) BISPECIFIC EPITOPE BINDING PROTEIN COMPRISING ANTI-4-1BB ANTIBODY AND A PD-1 PROTEIN OR FRAGMENTS THEREOF AND USE THEREOF

(71) Applicant: EUTILEX CO., LTD., Seoul (KR)

(72) Inventors: Byoung S. Kwon, Seoul (KR); Hanna Lee, Seoul (KR); Jin Sung Park, Seoul (KR); Seung Hee Han, Seoul (KR); Hyun Tae Son, Seoul (KR); Sun Woo Im, Seoul (KR); Hyeok-Jun Park, Seoul (KR); Eunhye Yoo, Seoul (KR); Sung Min Park, Seoul (KR); Yeonji Oh, Seoul (KR)

(73) Assignee: Eutilex Co., Ltd., Seoul (KR)

( * ) Notice: Subject to any disclaimer, the term of this patent is extended or adjusted under 35 U.S.C. 154(b) by 9 days.

This patent is subject to a terminal disclaimer.

(21) Appl. No.: 17/647,665

(22) Filed: Jan. 11, 2022

(65) Prior Publication Data

US 2022/0275083 A1    Sep. 1, 2022

Related U.S. Application Data

(60) Provisional application No. 63/135,812, filed on Jan. 11, 2021.

(51) Int. Cl.
| | | |
|---|---|---|
| *C07K 16/28* | (2006.01) | |
| *A61K 39/00* | (2006.01) | |
| *A61P 35/00* | (2006.01) | |

(52) U.S. Cl.
CPC .......... *C07K 16/2803* (2013.01); *A61P 35/00* (2018.01); *A61K 2039/505* (2013.01); *C07K 2317/21* (2013.01); *C07K 2317/24* (2013.01); *C07K 2317/565* (2013.01); *C07K 2317/732* (2013.01); *C07K 2317/734* (2013.01); *C07K 2317/76* (2013.01); *C07K 2317/92* (2013.01)

(58) Field of Classification Search
CPC ............ C07K 16/2803; C07K 2317/21; C07K 2317/24; C07K 2317/565; C07K 2317/732; C07K 2317/734; C07K 2317/76; C07K 2317/92; C07K 2317/70; C07K 16/2827; C07K 2317/524; C07K 2317/526; C07K 2317/622; C07K 2317/71; C07K 2319/32; C07K 16/2878; C07K 2317/31; C07K 2319/30; C07K 14/70503; A61P 35/00; A61K 2039/505; C12N 15/62

See application file for complete search history.

(56) References Cited

U.S. PATENT DOCUMENTS

| | | | |
|---|---|---|---|
| 9,808,507 B2 * | 11/2017 | Oh ....................... | C07K 16/2863 |
| 2015/0152192 A1 * | 6/2015 | Kim ....................... | C07K 16/22 |
| | | | 530/387.3 |
| 2020/0172626 A1 * | 6/2020 | Kwon ..................... | A61K 45/06 |

FOREIGN PATENT DOCUMENTS

WO    WO-2017070654 A8 *    6/2017    ............. A61K 35/17

OTHER PUBLICATIONS

Chester et. al. Blood. 131(1):49-57. (2018) (Year: 2018).*
Lee et. al. European Journal of Immunogenetics. 29:449-452. (2002) (Year: 2002).*
Almagro et. al., Front. Immunol. 2018; 8:1751 (Year: 2018).*
Rudikoff et al., Proc. Nat'l Acad. Sci. USA, 79:1979-83 (1982) (Year: 1982).*
Brown et al., J. Immunol., 156(9):3285-91 (1996) (Year: 1996).*
Chiu et al., Antibodies, 8(55):1-80. (2019) (Year: 2019).*
Okazaki et. al., (International Immunology. 19(7):813-824. (2007) (Year: 2007).*
Zak et. al. (Structure25:1163-1174. (2017)) (Year: 2017).*
Brinkmann et. al. MABs. 9(2):182-212. (2017) (Year: 2017).*
Herrmann et. al. 132(23):2484-2494. (2018) (Year: 2018).*
Li et. al. (Cellular & Molecular Immunology. 17(5):451-461 (2020)) (Year: 2020).*

* cited by examiner

*Primary Examiner* — Meera Natarajan
*Assistant Examiner* — Francesca Edgingtongiordano
(74) *Attorney, Agent, or Firm* — Wood, Phillips, Katz, Clark & Mortimer

(57) ABSTRACT

The present invention provides a bispecific epitope binding protein comprising an anti-4-1BB agonist antibody and a PD-1 protein or a fragment thereof that binds to PD-L1 with high affinity. The bispecific epitope binding protein simultaneously and independently binds to 4-1BB and PD-L1, which engage 4-1BB upregulated T cells, especially effector CD8+ T cells, with tumor cells expressing PD-L1. These interactions induce strong activation of the cytotoxic activity of anti-tumor effector CD8+ T cells by both blocking PD-1/PD-L1-mediated inhibitory signaling and activating 4-1BB-mediated costimulatory signaling in mouse models. This bispecific epitope binding protein has a much stronger oncolytic effect compared to each component alone.

27 Claims, 28 Drawing Sheets

Specification includes a Sequence Listing.

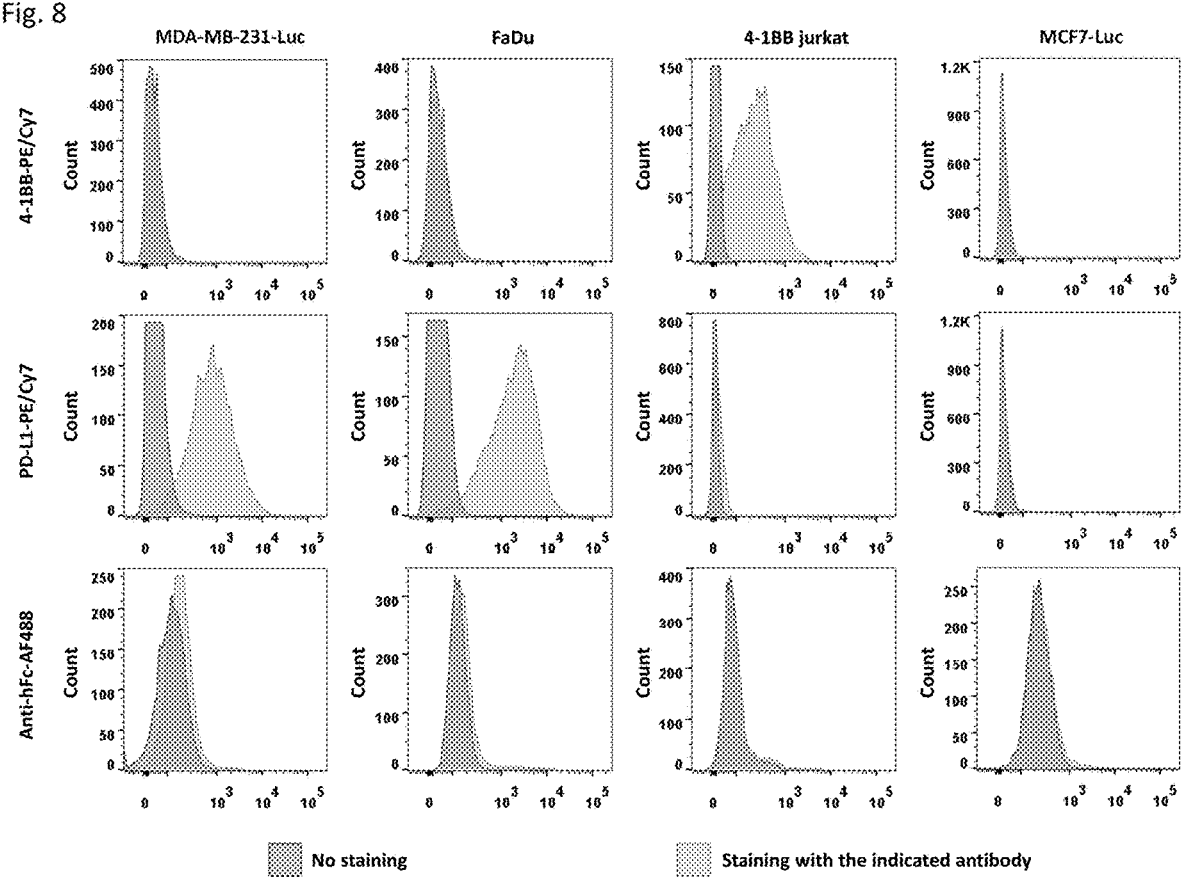

BISPECIFIC EPITOPE BINDING PROTEIN COMPRISING ANTI-4-1BB ANTIBODY AND A PD-1 PROTEIN OR FRAGMENTS THEREOF AND USE THEREOF

CROSS-REFERENCE TO RELATED APPLICATIONS

The present application claims priority to US provisional application no. U.S. 63/135,812, filed Jan. 11, 2021, the entire contents of which are incorporated herein by reference.

REFERENCE TO A SEQUENCE LISTING

In accordance with 37 CFR § 1.52(e)(5), the present specification makes reference to a Sequence Listing submitted electronically as a .txt file named "539293US_ST25.txt". The .txt file was generated on Jan. 10, 2022 and is 120,095 bytes in size. The entire contents of the Sequence Listing are herein incorporated by reference and form an integral part of this application's disclosure.

Technical Field of Invention

The present invention provides a bispecific epitope binding protein comprising an anti-4-1BB agonist antibody and a PD-1 protein or a fragment thereof that binds to PD-L1 with high affinity. The bispecific epitope binding protein simultaneously and independently binds to 4-1BB and PD-L1, which engage 4-1BB upregulated T cells, especially effector CD8+ T cells, with tumor cells expressing PD-L1. These interactions induce strong activation of the cytotoxic activity of anti-tumor effector CD8+ T cells by both blocking PD-1/PD-L1-mediated inhibitory signaling and activating 4-1BB-mediated costimulatory signaling in mouse models. This bispecific epitope binding protein has a much stronger oncolytic effect compared to each component alone.

BACKGROUND OF THE INVENTION

Cancer remains one of the leading causes of death in the world. Recent statistics report that 13% of the world population dies from cancer. According to estimates from the International Agency for Research on Cancer (IARC), in 2020 there were 19.3 million new cancer cases and 10.0 million cancer deaths worldwide. By 2030, the global burden is expected to grow to 21.7 million new cancer cases and 13 million cancer deaths due to population growth and aging and exposure to risk factors such as smoking, unhealthy diet and physical inactivity. Further, pain and medical expenses for cancer treatment cause reduced quality of life for both cancer patients and their families. Thus, there remains a critical need to expand the arsenal available to medical professionals to combat the ever-growing cancer crisis.

4-1BB is a type of costimulatory molecule expressed on the surface of T cells and antigen presenting cells in an immune response and is known as a type of tumor necrosis factor (TNF) receptor group, which is a cell membrane protein. The expression of 4-1BB is rapidly induced on the surface of CD4+ and CD8+ T cells after antigen- or mitogen-induced activation. The 4-1BB is a 55 kDa homodimer, and known to be expressed in various sites such as in T cell lines, thymocytes, and mature T cells of mouse, activated by ConA, phytohemagglutinin (PHA) and ionomycin, anti-CD3 antibodies or molecules, etc. In addition, some 4-1BB are present inside cells and binds to p561 which is a type of protein kinase, and thus it can be inferred that an extracellular signal is transduced into cells through 4-1BB.

Programmed cell death protein 1 (PD-1) is an immune checkpoint receptor that is an excellent target protein for cancer immunotherapy in the treatment of various cancers such as malignant melanoma, non-small cell lung cancer, and renal cell carcinoma. PD-1 is a receptor present on the surface of T cells and belongs to the immunoglobulin superfamily. When PD-1 binds to programmed death ligand 1 (PD-L1) or programmed death ligand 2 (PD-L2), signal transduction involving PD-1 is activated, and T cell proliferation, interferon gamma and interleukin 2 production, and T cell receptor signal transduction are inhibited, thereby inhibiting T cell activation. It is known that various types of cancer cells express PD-L1, which results in the loss of function of T cells, and this acts as a mechanism for cancer cells to evade the attack of the immune system.

4-1BB/4-1BBL (4-1BB ligand) provides a stimulatory signal, whereas PD-1/PD-L1 provides an inhibitory signal to T lymphocytes. Various forms of agonists for 4-1BB or blockers to PD-L1 show strong anti-tumor activity, mainly on regulating CD8+ T cells. Therefore, a synergistic or additive anti-tumor effect can be achieved by combining an agonist of 4-1BB with a PD-L1 blocker.

Under this technical background, the inventors of the present application developed the present invention by considering the overall size of the therapeutic candidate material, testing various combinations of antibodies and proteins, and selecting the bispecific epitope binding protein exhibiting the best anti-tumor activity.

SUMMARY OF THE INVENTION 4-1BB/4-1BBL provides a stimulatory signal, whereas PD-1/PD-L1 provides an inhibitory signal to T lymphocytes. Various forms of agonists for 4-1BB or blockers to PD-L1 show strong anti-tumor activity, mainly on regulating CD8+ T cells. Therefore, the present inventors speculate that a synergistic or additive anti-tumor effect can be achieved by combining an agonist of 4-1BB with a PD-L1 blocker.

In view of the foregoing, the inventors of the present application developed the present invention by considering the overall size of the therapeutic candidate material, testing various combinations of antibodies and proteins, and selecting the bispecific epitope binding protein exhibiting the best anti-tumor activity.

The purpose of the present invention is to provide a bispecific epitope binding protein exhibiting excellent anti-tumor activity.

In order to achieve the foregoing purpose, the present invention provides a bispecific epitope binding protein which comprises a combination of (VH), (VL), (X), (VH)n, (VL)n, (X)n, (VH)n-Y, (VL)n-Y, (VH-VL)n-Y, (VL-VH)n-Y, (X)n-Y, Y-(VH)m, Y-(VL)m, Y-(VH-VL)m, Y-(VL-VH)m, and/or Y-(X)m. In the present invention, the domains can be in a single polypeptide or the "heavy chain" and "light chain" can be in separate polypeptides.

In the foregoing, VH, VL, and/or X are connected to Y directly or through a hinge and/or a linker on either the N-terminal side or the C-terminal side.

In the foregoing, VH and VL refer to the variable heavy region and variable light region, respectively, of antibodies or antigen-binding fragments thereof that bind to 4-1BB.

In the foregoing, X is a PD-1 protein or fragment thereof that binds to PD-L1, including modified or engineered, affinity matured, and/or mutated PD-1 protein or fragment thereof.

In the foregoing, Y refers to a fragment of the heavy chain constant region or the light chain constant region. The fragment of the heavy chain constant region can include one or more of the three constant region domains CH1, CH2 and CH3, and fragments thereof. The fragment of the light chain constant region can include the constant region domain CL or a fragment thereof. In an embodiment of the invention, Y is a fragment comprising either the CH2 or the CH3 domain. In an embodiment of the invention, Y is a fragment comprising either the CH1. In an embodiment of the invention, Y is a fragment comprising the CL domain.

In the foregoing, n and m are each independently an integer of 1 to 5, inclusive of all integers 1, 2, 3, 4, or 5.

The bispecific epitope binding protein of the present invention may contain an N-terminal signal peptide. Signal peptides that may be used in the present invention generally are 12 to 40, 15 to 35, or 16 to 30 amino acids in length and function to prompt a cell to translocate the protein, usually to the cellular membrane. The specific sequence of the signal peptide for us in the present invention is not particularly limited and may include, for example, any known signal peptide sequence. A non-limiting example of a suitable N-terminal signal peptide has the sequence: MEWSWVFLVTLLNGIQC (SEQ ID NO: 29). Although less preferred, it is also possible that the signal peptide can be located at the C-terminus.

Examples of bispecific epitope binding proteins of the present invention are SEQ ID NO: 1-10 and 14 (S01-S10). In a preferred embodiment, the bispecific epitope binding protein of the present invention has the sequence of SEQ ID NO: 3 (S03).

With respect to these identified exemplary bispecific epitope binding proteins, it is understood that variation in the sequence is permitted so long as bispecific binding is preserved. Thus, the present invention sequences that retain bispecific binding affinity for 4-1BB and PD-L1 which have at least about 30-40% overall sequence identity, preferably at least about 50%, 60%, 70%, 80% or 85% or greater sequence identity, and more preferably at least about 90%, 95%, 96%, 97%, 98%, or 99% or greater sequence identity.

In some embodiments, the bispecific epitope binding protein of the present invention is a humanized antibody.

In some embodiments are polynucleotides expression the bispecific epitope binding protein of the present invention, vectors comprising the polynucleotides, and cells containing the polynucleotide or vector of the present invention.

Provided herein are pharmaceutical compositions comprising: bispecific epitope binding protein, any one of the nucleic acid molecules described herein, any one of the recombinant vectors described herein, or any one of the cells described herein; and a pharmaceutically acceptable carrier.

Provided herein are kits comprising any one of the pharmaceutical compositions described herein.

Provided herein are methods of producing a bispecific epitope binding protein, the method comprising: culturing any one of the cells described herein in a culture medium under conditions sufficient to result in the production of the bispecific epitope binding protein; and recovering the bispecific epitope binding protein from the cell and/or the culture medium.

Provided herein are methods of treating a subject in need thereof, the method comprising: administering to the subject a composition that comprises or delivers any one of the bispecific epitope binding proteins described herein, any one of the nucleic acid molecules described herein, any one of the recombinant vectors described herein, or any one of the cells described herein, thereby treating a disease or a condition. In some embodiments, the subject has, or is at risk for developing, cancer. In some embodiments, the cancer comprises a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, prostate cancer, and combinations thereof.

The above objects highlight certain aspects of the invention. Additional objects, aspects and embodiments of the invention are found in the following detailed description of the invention.

BRIEF DESCRIPTION OF DRAWINGS

A more complete appreciation of the invention and many of the attendant advantages thereof will be readily obtained as the same becomes better understood by reference to the following Figures in conjunction with the detailed description below.

FIG. 8 shows the results of the cell binding assay in Example 7. Specifically, FIG. 8 shows the expression levels of 4-1BB and PD-L1 in various cell lines to be used in the assay.

DETAILED DESCRIPTION OF THE INVENTION

Figure 1:
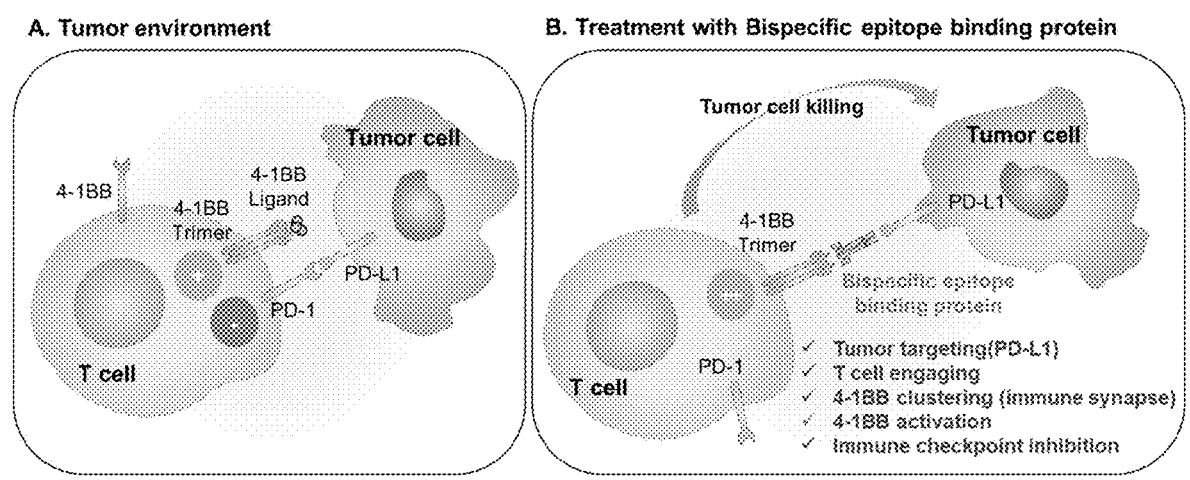
FIG. 1 shows the mode of action of bispecific epitope binding proteins for its dual function of: T cell engagers and checkpoint inhibitors.

Unless defined otherwise, all technical and scientific terms used herein have the same meaning as commonly understood by one of ordinary skill in the art to which this invention belongs (e.g., the fields of enzymology, biochemistry, cellular biology, molecular biology, and the medical sciences). In general, the nomenclature used herein is well known and commonly used in the art.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present invention provides a bispecific epitope binding protein which comprises a combination of (VH), (VL), (X), (VH)n, (VL)n, (X)n, (VH)n-Y, (VL)n-Y, (VH-VL)n-Y, (VL-VH)n-Y, (X)n-Y, Y-(VH)m, Y-(VL)m, Y-(VH-VL)m, Y-(VL-VH)m, and/or Y-(X)m. In the present invention, the domains can be in a single polypeptide or the "heavy chain" and "light chain" can be in separate polypeptides.

In the foregoing, VH, VL, and/or X are connected to Y directly or through a hinge and/or a linker on either the N-terminal side or the C-terminal side. For example, VH, VL, and/or X are connected to CH2 directly or through a hinge or a linker and, independently, CH3 is connected to VH, VL, and/or X directly or through a hinge or a linker.

In the foregoing, VH and VL refer to a variable heavy region and a variable light region, respectively, of antibodies or antigen-binding fragments thereof that bind to 4-1BB.

In the foregoing, X is a PD-1 protein or fragment thereof that binds to PD-L1, including modified or engineered, affinity matured, and/or mutated PD-1 protein or fragment thereof.

In the foregoing, Y refers to a fragment of the heavy chain constant region or the light chain constant region. The fragment of the heavy chain constant region can include one or more of the three constant region domains CH1, CH2 and CH3, and fragments thereof. The fragment of the light chain constant region can include the constant region domain CL. In an embodiment of the invention, Y is a fragment comprising either the CH2 or the CH3 domain. In an embodiment of the invention, Y is a fragment comprising either the CH1. In an embodiment of the invention, Y is a fragment comprising the CL domain.

In an embodiment of the present invention, Y is derived from a human IgG antibody.

With respect to the three constant region domains CH1, CH2 and CH3, and fragments thereof, the heavy chain constant region for each of IgG1 (SEQ ID NO: 32), IgG2 (SEQ ID NO: 34), IgG3 (SEQ ID NO: 35), and IgG4 (SEQ ID NO: 36) embracing the CH1, CH2, and CH3 domains are well known in the art. In the present invention, one or more of the three constant region domains CH1, CH2 and CH3, and fragments thereof, may be used. To this end, Y (including the one or more constant region domains CH1, CH2 and CH3, and fragments thereof) may be derived from any of SEQ ID NOs: 32, 34, 35, or 36 or a sequence that has at least about 80%, 85%, 90%, 95%, 96%, 97%, 98%, or 99% or greater sequence identity. In a preferred embodiment, Y (including the one or more constant region domains CH1, CH2 and CH3, and fragments thereof) is derived from IgG1 heavy chain constant region having the sequence of SEQ ID NO: 32 or a sequence that is at least about 80%, 85%, 90%, 95%, 96%, 97%, 98%, or 99% or greater sequence identity to SEQ ID NO: 32 wherein the variations include additions, deletions, and/or substitutions. An example of a modified heavy chain constant region is SEQ ID NO: 33 from which one or more of constant region domains CH1, CH2 and CH3, and fragments thereof, for use in the present invention can be derived.

With respect to the constant region CL, and fragments thereof, the light chain constant region for immunoglobulin kappa (SEQ ID NO: 37), immunoglobulin lambda 1 (SEQ ID NO: 38), and immunoglobulin lambda 2 (SEQ ID NO: 39) are well known in the art. To this end, Y may be derived from any of SEQ ID NOs: 37-39 or a sequence that has at least about 80%, 85%, 90%, 95%, 96%, 97%, 98%, or 99% or greater sequence identity. In a preferred embodiment, Y is derived from immunoglobulin kappa light chain constant region having the sequence of SEQ ID NO: 37 or a sequence that is at least about 80%, 85%, 90%, 95%, 96%, 97%, 98%, or 99% or greater sequence identity to SEQ ID NO: 37 wherein the variations include additions, deletions, and/or substitutions.

In the foregoing, n and m are each independently an integer of 1 to 5, inclusive of all integers 1, 2, 3, 4, or 5.

The regions of (VH), (VL), (VH)n-Y, (VL)n-Y, (VH-VL)n-Y, (VL-VH)n-Y, (X)n-Y, Y-(VH)m, Y-(VL)m, Y-(VH-VL)m, Y-(VL-VH)m, and/or Y-(X)m, when present, may appear in any order from the N-terminus to the C-terminus. Further, when multiple copies of (VH), (VL), (VH)n-Y, (VL)n-Y, (VH-VL)n-Y, (VL-VH)n-Y, (X)n-Y, Y-(VH)m, Y-(VL)m, Y-(VL-VH)m, and/or Y-(X)m are present, they may be present in any order relative to the other regions and need not be directly adjacent to like kind regions.

In an embodiment of the present invention, the bispecific epitope binding protein has the structure of An-A'n'-B-Cm-C'm',
  wherein:
  A, A', C, C': VH, VL, VH-VL, VL-VH or X
  B: Y
  VH, VL, X, Y, n, and m are as defined above and each of VH, VL, X, Y are connected directly or with a linker and/or a hinge. The values n' and m' are independently an integer of 1 to 5, inclusive of all integers 1, 2, 3, 4, or 5.

In an embodiment of the present invention, the bispecific epitope binding protein has the structure of An-B-Cm,
  wherein:
  A or C: VH-VL, VL-VH or X
  B: Y
  VH, VL, X, Y, n, and m are as defined above and each of VH, VL, X, Y are connected directly or with a linker and/or a hinge.

In an embodiment of the present invention, a CH1 domain is C-terminally linked to (VH-VL)n, (VL-VH)n, or (X)n directly or with a hinge and/or a linker and a CH2/CH3 domain(s) is N-terminally linked to (VH-VL)m, (VL-VH)m, (X)m directly or with a hinge and/or a linker. Further, in this embodiment the CH1 domain is linked to the CH2/CH3 domains(s) directly or with a hinge and/or linker. In the foregoing, VH, VL, X, n, and m are as defined above.

The present invention also embraces embodiments wherein the bispecific epitope binding protein has a heavy chain and a light chain each on distinct polypeptides. In this embodiment, the heavy chain comprises VH-VL, VL-VH, X, and/or VH-CH1 connected to CH2 directly or through a linker and/or a hinge and, independently, CH3 is connected to VH-VL, VL-VH or X directly or through a linker and/or a hinge. In this embodiment, the light chain comprises VL connected to CL directly or with a linker and/or a hinge. VH, VL, are X, are as defined above and each of VH, VL, X, CH1, CH2, CH3, and CL are connected directly or via a linker and/or a hinge. As an example of this embodiment, reference is made to S09 and S10 (see FIG. 2) wherein S09 has a heavy chain of SEQ ID NO: 9 and a light chain of SEQ ID NO: 14 and S10 has a heavy chain of SEQ ID NO: 10 and a light chain of SEQ ID NO: 14.

It is preferred that the bispecific epitope binding protein is in scFv form.

In an exemplary embodiment of the present invention, provided is a bispecific epitope binding protein which comprises (VH and VL, in either order)n-Y and/or Y-(X)m,
  wherein:
  Y is independently a CH2 or CH3 domain;
  the VH, and VL, and CH2 and/or CH3, or CH2 and/or CH3 and X are connected directly or with a hinge and/or a linker;
  the VH and VL refer to the variable heavy region and variable light region, respectively, of antibodies or antigen-binding fragments thereof that bind to 4-1BB;
  the X is a PD-1 protein or fragment thereof that binds to PD-L1, including modified or engineered, affinity matured, and/or mutated PD-1 protein or fragment thereof;
  and n and m are each an integer of 1-5, inclusive of all integers 1, 2, 3, 4, or 5.

A specific example of this embodiment is a scFv arranged as (VL-VH)n-CH2-CH3-(X)m written from N-terminus to C-terminus. VL, VH, X, n, and m are as defined above. In an embodiment of this example is where VL and VII are connected by a linker, VII and CH2 are connected by a linker, CH3 and (X)m are connected by a linker, and/or CH2 and CH3 are connected by a linker. In this embodiment, one or more of the linkers may be followed by or follow a hinge. Alternatively, one or more of the aforementioned connections may be direct or by a hinge.

Another exemplary embodiment of the present invention is a bispecific epitope binding protein which comprises (X)m-Y and/or Y-(VH and VL, in either order)n,
  wherein:
  Y is independently a CH2 or CH3 domain;
  the VH, and VL, and CH2 and/or CH3, or CH2 and/or CH3 and X are connected directly or through a hinge and/or a linker;
  the VH and VL refer to the variable heavy region and variable light region, respectively, of antibodies or antigen-binding fragments thereof that bind to 4-1BB;
  the X is a PD-1 protein or fragment thereof that binds to PD-L1, including modified or engineered, affinity matured, and/or mutated PD-1 protein or fragment thereof;
  and n and m are each an integer of 1-5, inclusive of all integers 1, 2, 3, 4, or 5.

A specific example of this embodiment is a scFv arranged as (X)m-CH2-CH3-(VH-VL)n written from N-terminus to C-terminus. VL, VH, X, n, and m are as defined above. In an embodiment of this example is where (X)m and CH2 are connected by a linker, CH3 and VH are connected by a linker, VH and VL are connected by a linker, and/or CH2 and CH3 are connected by a linker. In this embodiment, one or more of the linkers may be followed by or follow a hinge. Alternatively, one or more of the aforementioned connections may be direct or by a hinge.

In an embodiment of the present invention each of n and m are individually selected from integers 1, 2, 3, 4, or 5 such that any combination of n and m having these integer values may be present. Where multiple VH, VL, and/or X are present (i.e., n and/or m is a value greater than 1) they may be connected directly or the copies may be separated by a hinge and/or a linker sequence. In a preferred embodiment the multiple copies are separated by a linker sequence.

The bispecific epitope binding protein comprising (VII and VL, in either order)n-Y and/or Y-(X)m according to the present invention is the first arm of a dual specific therapeutic agent, and has a bispecific epitope binding protein comprising the same (VII and VL, in either order)n-Y and/or Y-(X)m, as a second arm, to form a pair. The same would be the case wherein when the first arm of the pair is (X)m-Y and/or Y-(VH and VL, in either order)n, the second arm of the bispecific epitope binding protein would comprise the same (X)m-Y and/or Y-(VH and VL, in either order)n. In other words, the resulting antibody making up the bispecific epitope binding protein of the present invention should have the same arrangement in one arm as the other arm of the pair.

The VH, and VL and CH2 and/or CH3, or CH2 and/or CH3 and X may be connected directly or through a hinge and/or a linker. A cysteine residue may be included at the linking site for linking via a hinge and/or a linker. While the cysteine residue forms a disulfide bond, VH and VL and CH2 and/or CH3, or CH2 and/or CH3 and X may be connected directly or through a hinge and/or a linker.

In consideration of the overall size of the therapeutic candidate material and various combinations of antibodies and proteins, the best anti-tumor activity was shown through the combination of the agonist anti 4-1BB antibody fragment and the soluble PD-1 that binds to PD-L1 with high affinity.

In an embodiment of the present invention, the VH region includes SEQ ID NO: 23. In an embodiment of the present invention, the VL region includes SEQ ID NO: 25. In an embodiment of the present invention, the anti-4-113B antibody fragment has a VH region including SEQ ID NO: 23 and a VL region including SEQ ID NO: 25.

In an embodiment of the present invention, the anti-4-1BB antibody fragment is in scFv form.

In an embodiment of the present invention, nucleic acid encoding SEQ ID NO: 23 is the sequence of SEQ ID NO: 24. In an embodiment of the present invention, the nucleic acid encoding SEQ ID NO: 25 is the sequence of SEQ ID NO: 26.

```
SEQ ID NO: 23:
QVQLVQSGAEVKKPGASVKLSCKASGYTFSSYWMHWVRQAPGQGLEWIGEI

NPGNGHTNYNEKFKSRVTMTRDTSTSTAYMELSSLRSEDTAVYYCARSFKT

ARAFAYWGQGTLVTVSS

SEQ ID NO: 24:
caggtccagctggtgcagagcggcgccgaagtgaaaaaacctggggcaagt gtcaagctgtcctgtaaggccagcggttataccttctcctcatattggatg cactgggtgaggcaagcccctggacaagggctggaatggatcggtgaaatt aatcccggaaatggccatacaaactacaatgaaaaattcaaaagtcgagtg accatgacacgggacacatccacttccactgcatacatggagctttcgagt ctgcgctccgaggatacagctgtctattactgcgcacgcagtttttaaaact gccagagcctttgcctactggggtcagggaaccctggtcaccgttagcagc

SEQ ID NO: 25:
DIVMTQSPAFLSVTPGEKVTITCRASQTISDYLHWYQQKPDQAPKLLIKYA

SQSISGIPSRFSGSGSGTDFTFTISSLEAEDAATYYCQDGHSWPPTFGQGT

KLEIK

SEQ ID NO: 26:
gacattgtgatgacacagtcccctgctttcctgagcgttacacccggcgaa aaggtgactatcacatgcagggctagtcagaccatctcagactaccttcat tggtatcaacagaagccagaccaggctcctaagttgctgataaagtacgcc tcccaatccatttccggcattccttcccgttttttccggctccggctccggc
```

-continued
```
accgactttacgttcaccatctcttctttggaggctgaagacgcagctacc tattactgtcaggatggtcacagaggccaccaactttcgggcaaggcacca agctggagatcaaa
```

The PD-1 protein or fragment can be used with/without affinity maturation so long as it binds to PD-L1. Thus, the PD-1 protein or fragment thereof may be native PD-1 or a fragment thereof. Alternatively, the PD-1 protein or fragment thereof may be modified or engineered, affinity matured, and/or mutated. To obtain molecularly evolved PD-1, first, a 3D complex between PD-1 and PD-L1 is used, major contributing PD-1 amino acids were selected, random mutations with the selected amino acids were constructed, and yeast surface display was used for screening. Affinity matured PD-1 was referred to as euPD-1. With respect to the mutations of the PD-1 protein or fragment thereof, the which have at least about 30-40% overall sequence identity, preferably at least about 50%, 60%, 70%, 80%, or 85% or greater sequence identity, and more preferably at least about 90%, 95%, 96%, 97%, 98%, or 99% or greater sequence identity, wherein the PD-1 protein or fragment thereof retains specific binding affinity for PD-L1.

In an embodiment of the present invention, the euPD-1 may include the sequence of SEQ ID NO: 27. Consistent with the foregoing description, the PD-1 protein or fragment thereof may have at least about 30-40% overall sequence identity to SEQ ID NO: 27, preferably at least about 50%, 60%, 70%, 80%, or 85% or greater sequence identity to SEQ ID NO: 27, and more preferably at least about 90%, 95%, 96%, 97%, 98%, or 99% or greater sequence identity to SEQ ID NO: 27, wherein the PD-1 protein or fragment thereof retains specific binding affinity for PD-L1.

In an embodiment of the present invention, the nucleic acid encoding SEQ ID NO: 27 is the sequence of SEQ ID NO: 28.

```
SEQ ID NO: 27:
FLESPDRPWNAPTFSPALLLVAEGDNATFTCSFSNASESFHVVWHRESPSG

QTDTLAAFPEDRSQPGQDHRFRVTRLPNGRDFHMSVVRAQRNDSGTYVCGV

ISLAPKIQIKESLRAELRVTERRAEVPTAHPSPSPRPAGQFQTLVVG

SEQ ID NO: 28:
tttctcgaatcaccggacagaccctggaatgcgcccacattctcaccagca cttttgcggtagcagagggcgataatgctacattcacgtgttccttcagta atgcaagcgagtcatttcatgtggtttggcatcgagagtcacctagtgggc agactgatacacttgccgcattcccggaagatcgctcccagccaggtcagg atcaccggttcagggtaacccgactgccgaatgggcgcgatttccatatga gcgttgtccgggcgcaacggaacgatagtggaacatacgtgtgtggcgtaa tatccctcgctcccaaaatacaaataaaggagtctctgagagcagagctga gagtgacagaacgacgggcggaagttcccacggctcatccgtcaccaagtc cgcgccccgcaggccaatttcaaacgctcgtcgtaggc
```

The bispecific epitope binding protein of the present invention may contain a signal peptide, for example an N-terminal signal peptide. Signal peptides that may be used in the present invention generally are 12 to 40, 15 to 35, or 16 to 30 amino acids in length and function to prompt a cell to translocate the protein, usually to the cellular membrane.

The specific sequence of the signal peptide for us in the present invention is not particularly limited and may include, for example, any known signal peptide sequence. A non-limiting example of a suitable N-terminal signal peptide has the sequence: MEWSWVFLVTLLNGIQC (SEQ ID NO: 29). Although less preferred, it is also possible that the signal peptide can be located at the C-terminus.

Examples of bispecific epitope binding proteins of the present invention are SEQ ID NO: 1-10 and 14 (S01-S10). In a preferred embodiment, the bispecific epitope binding proteins of the present invention has the sequence of SEQ ID NO: 3 (S03).

With respect to these identified exemplary bispecific epitope binding proteins, it is understood that variation in the sequence is permitted so long as bispecific binding is preserved. Thus, the present invention sequences that retain bispecific binding affinity for 4-1BB and PD-L1 which have at least about 30-40% overall sequence identity, preferably at least about 50%, 60%, 70%, 80%, or 85% or greater sequence identity, and more preferably at least about 90%, 95%, 96%, 97%, 98%, or 99% or greater sequence identity.

Through cell binding and dual antigen analysis, it was confirmed that S03 (SEQ ID NO: 3) independently binds to both targets at the same time.

As results of the 4-1BB bioassay, a biologically relevant MOA-based assay showed strong PD-L1-dependent T cell activation by S03.

When tested on human PD-L1-expressing tumor cells in the 4-1BB knock-in mouse model, S03 showed a much stronger oncolytic effect compared to each component alone and other candidates such S05 or S07.

Furthermore, when S03 was injected, the T cells, especially effector CD8+ T cells, were increased in the peripheral blood, and as a result, the size of the tumor decreased. S03 is a promising anti-tumor agent, which promotes CD8+ T cell infiltration and activates T cells in situ at the tumor site by simultaneously binding to two different targets, 4-1 BB and PD-L1.

As a result, S03 is a bispecific epitope binding protein comprising an anti-4-1BB antibody and euPD-1, and exhibits the following properties:
1. Reduced ADCC and CDC activity through Fc engineering;
2. Stronger binding affinity than native PD-1;
3. Selectively activates and potentiates PD-L1-positive tumor-directed T-cell responses in in-vitro preclinical studies.
4. A better effect on tumor removal compared to the control group antibody.

"Bispecific" or "dual specific" is a property of a binding protein capable of modulating the activity of two different targets by specifically binding to the targets, and preparation is carried out by an antibody or a protein that specifically binds to each target, or a fragment thereof, and two distinct antigen-binding arms (arm: specificity to two targets) is possessed, which is monovalent for each antigen that binds thereto. In particular, the bispecific epitope binding protein of the present invention relates to the specific binding of 4-1BB and PD-L1 or having a specific affinity for 4-1BB and PD-L1.

As used herein, the term "antibody" refers to an anti-4-1BB antibody that specifically binds to 4-1BB. The scope of the present invention includes not only complete antibody forms that specifically bind to 4-1BB, but also antigen-binding fragments of the antibody molecule.

The term "a PD-1 protein" includes a PD-1 protein or fragment that binds to PD-L1. The scope of the present invention includes not only complete recombinant protein forms that specifically bind to PD-L1, but also PD-1-binding fragments of the recombinant protein molecule. Further, as stated above, the PD-1 protein or fragment can be used with/without affinity maturation so long as it binds to PD-L1. Thus, the PD-1 protein or fragment thereof may be native PD-1 or a fragment thereof. Alternatively, the PD-1 protein or fragment thereof may be modified or engineered, affinity matured, and/or mutated consistent with the description above.

A complete antibody has a structure having two full-length light chains and two full-length heavy chains, and each light chain is linked to a heavy chain by a disulfide bond.

As used herein, the term "heavy chain" refers to the full-length heavy chain comprising a variable region domain VH comprising an amino acid sequence having sufficient variable region sequence to confer specificity to an antigen, and three constant region domains CH1, CH2 and CI-13, and the fragments thereof. In addition, as used herein, the term "light chain" refers to the full-length light chain comprising a variable region domain VL comprising an amino acid sequence having sufficient variable region sequence to confer specificity to an antigen, and a constant region domain CL, and the fragments thereof.

The whole antibody includes subtypes or variants of IgA, IgD, IgE, IgM and IgG, in particular, IgG includes IgG1, IgG2, IgG3 and IgG4. The heavy chain constant region has gamma ($\gamma$), mu ($\mu$), alpha ($\alpha$), delta ($\delta$) and epsilon ($\epsilon$) types and subclasses gamma 1 ($\gamma$1), gamma 2 ($\gamma$2), gamma 3 ($\gamma$3), gamma 4 ($\gamma$4), alpha1 ($\alpha$1) and alpha2 ($\alpha$2). The constant region of the light chain includes a kappa ($\kappa$) and a lambda ($\lambda$) type.

An antigen-binding fragment or antibody fragment of an antibody refers to a fragment having an antigen-binding function, and includes Fab, F(ab'), F(ab')2, Fv and the like. Among the antibody fragments, Fab has a structure having variable regions of light and heavy chains, constant regions of light chain and the first constant region (CH1) of heavy chain, and has one antigen-binding site. Fab' differs from Fab in that it has a hinge-region comprising one or more cysteine residues at the C-terminus of the heavy chain CH1 domain. F(ab')2 fragment is formed when a cysteine residue in the hinge region of Fab' forms a disulfide bond.

Fv corresponds to a minimal antibody fragment having only a heavy chain variable region and a light chain variable region. In a double-chain Fv (two-chain Fv), the heavy chain variable region and the light chain variable region are connected by a non-covalent bond, and in single-chain Fv (scFv), the heavy chain variable region and the light chain variable region are connected by a covalent bond through a peptide linker or directly connected at the C-terminus to form a structure such as a dimer like double chain Fv. These antibody fragments can be prepared by proteolytic enzymes (for example, restriction digestion of the intact antibody with papain yields Fab, and digestion with pepsin yields F(ab')2), or genetic recombination technology.

An "Fv" fragment is an antibody fragment that comprises a complete antibody recognition and binding site. This region is a dimer in which one heavy chain variable domain and one light chain variable domain are joined.

A "Fab" fragment comprises the variable and constant domains of a light chain and the variable and first constant domains (CH1) of a heavy chain. F(ab')2 antibody fragments generally comprise a pair of Fab' fragments covalently linked by cysteines in the hinge region present at the C-terminus of the Fab' fragment.

A "single chain Fv(scFv)" antibody fragment is a construct consisting of a single polypeptide chain comprising the VH and VL domains of an antibody. A polypeptide linker, that allows scFv to form a desired structure for antigen binding, may be additionally included between VH domain and VL domain.

A "hinge" in the present invention is not specifically limited and is well known in the art. The hinge is refers to a flexible amino acid stretch in the central part of the heavy chains of the IgG and IgA immunoglobulin classes, which links these 2 chains by disulfide bonds. It is rich in cysteine and proline amino acids, extremely variable in amino acid sequence, and has no resemblance to any other immunoglobulin region. The hinge region may vary in length and is generally in the range of 10 to 50 amino acid residues. Reference is made to the review of Adlersberg J B, Ric Clin Lab. July-September 1976; 6(3):191-205. By way of example, mention is made to the hinge sequences of EPKSCDKTHTCPPCP (SEQ ID NO: 30) and DKTHTCPPCP (SEQ ID NO: 31).

It is particularly advantageous in the present invention to have the hinge follow a linker sequence. It is also possible for a hinge to precede a linker sequence.

Antibodies of the present invention include monoclonal antibodies, multispecific antibodies, human antibodies, humanized antibodies, chimeric antibodies, scFvs, Fab fragments, F(ab')2 fragments, disulfide-linked Fvs (sdFv) and anti-idiotypic (anti-Id) antibodies, or epitope-binding fragments of the antibodies, and the like, but are not limited thereto.

The heavy chain constant region may be selected from any one isotype of gamma (γ), mu (μ), alpha (α), delta (δ) or epsilon (ε). For example, the constant region is gamma 1 (IgG1), gamma 2 (IgG2), gamma 3 (IgG3) or gamma 4 (IgG4). The light chain constant region may be kappa or lambda type.

The monoclonal antibody refers to antibodies obtained from a substantially homogeneous population of antibodies. In other words, it refers to the same except for natural mutations which may exist in a small amount among the antibodies. As the monoclonal antibodies are highly specific, they are induced against a single antigenic site. In contrast to conventional (polyclonal) antibodies, which typically include different antibodies for different determinants (epitopes), each monoclonal antibody is directed against a single determinant on the antigen.

The term "epitope" refers to a protein determinant to which an antibody can specifically bind. Epitopes are usually composed of a group of chemically active surface molecules, such as amino acids or sugar side chains, and generally have specific three-dimensional structural characteristics as well as specific charge properties.

The non-human (e.g. mouse) antibody of a "humanized" form is a chimeric antibody that comprises minimal sequence derived from non-human immunoglobulin. In most cases, a humanized antibody is a human immunoglobulin (receptor antibody) in which residues from a hypervariable region of a recipient are replaced by residues from a hypervariable region of a non-human species (donor antibody), such as the mouse, rat, rabbit or non-human primate that retains the desired specificity, affinity and ability.

The term "human antibody" refers to a molecule derived from human immunoglobulin, in which the entire amino acid sequence constituting the antibody, including the complementarity determining region and structural region, is composed of human immunoglobulin.

A chimeric antibody (immunoglobulin) and a fragment of the antibody exhibiting a desired biological activity, the chemical antibody in which a part of a heavy chain and/or a light chain is identical to or homologous to the corresponding sequence in an antibody derived from a particular species or belonging to a particular antibody class or subclass, while the remaining chain(s) have is identical to or homologous to a corresponding sequence in an antibody derived from another species or belonging to another antibody class or subclass.

The "variable region" of an antibody used herein refers to light chain and heavy chain parts of an antibody molecule comprising amino acid sequences of complementarity determining region (CDR; that is, CDR1, CDR2 and CDR3) and framework region (FR). VH refers to a variable domain of a heavy chain. VL refers to a variable domain of a light chain.

The term "complementarity determining region (CDR)" refers to an amino acid residue of an antibody variable domain, which is an entity necessary for antigen binding. Each variable domain typically has three CDR regions identified as CDR1, CDR2 and CDR3.

A "framework region (FR)" is a variable domain residue other than a CDR residue. Each variable domain typically has four FRs: FR1, FR2, FR3 and FR4.

An scFv is an antibody fragment, which is a construct consisting of a single polypeptide chain comprising the VH and VL domains of an antibody. It may further comprise a polypeptide linker between the VII domain and the VL domain so that the scFv can form the desired structure for antigen binding.

In a particularly preferred embodiment of the present invention, the bispecific epitope binding protein is a single polypeptide.

The linker may be a peptide linker and may have a length of about 10-25 aa, about 10 to 20 aa, or about 12 to 19 aa, inclusive of each integer value therein as if recited. For example, hydrophilic amino acids such as glycine and/or serine may be included but are not limited thereto.

Specifically, the linker may include, for example, $(GS)_n$, $(GGS)_n$, $(GSGGS)_n$ or $(G_nS)_m$ (n and m are each 1 to 10, in other words n and m can be independently any of 1, 2, 3, 4, 5, 6, 7, 8, 9, or 10), but the linker may be, for example, $(G_nS)_m$ (n and m are each 1 to 10, in other words n and m can be independently any of 1, 2, 3, 4, 5, 6, 7, 8, 9, or 10). Specific reference is given to a $(G_4S)_3$ (SEQ ID NO: 15) or a $(G_4S)_2$ (SEQ ID NO: 16) linker. The linker may also be one or more copies of a 218 linker (SEQ ID NO: 17) or a 218S linker (SEQ ID NO: 18). Of course, also envisioned in the present invention are combinations of the foregoing linkers.

In an embodiment, the present invention relates to a nucleic acid encoding the bispecific epitope binding protein. A bispecific epitope binding protein can be recombinantly produced by isolating the nucleic acid. That is, embraced by the present invention are nucleic acids encoding the bispecific epitope binding protein, vectors containing a nucleic acid encoding the bispecific epitope binding protein, and cells containing the nucleic acid and/or vector.

It is interpreted that "nucleic acid" comprehensively includes DNA (gDNA and cDNA) and RNA molecules, and nucleotides, which are the basic constituent unit of nucleic acids, include natural nucleotides as well as analogues in which sugar or base sites are modified. The sequences of the nucleic acids encoding the heavy chain and light chain variable regions of the present invention may be modified. Such modifications include additions, deletions, or non-conservative or conservative substitutions of nucleotides.

DNA can be easily isolated or synthesized using conventional molecular biological techniques, and nucleic acid is isolated and inserted into a replicable vector for further cloning (amplification of DNA) or further expression. Based on this, the present invention relates to a recombinant expression vector comprising the nucleic acid from another aspect.

As used herein, the term "vector" is a means for expressing a target gene in a host cell, and includes a plasmid vector, a cosmid vector, a bacteriophage vector, an adenovirus vector, a retroviral vector, an adeno-associated viral vector and the like. Components of a vector generally include, but are not limited to, one or more of the following: a signal sequence, an origin of replication, one or more antibiotic resistance marker genes, an enhancer element, a promoter and a transcription termination sequence. The nucleic acid encoding the bispecific epitope binding protein is operatively linked with a promoter, transcription termination sequence and the like.

The term "operably linked" refers to a functional linkage between a nucleic acid expression regulatory sequence (e.g. an array of promoter, signal sequence or transcriptional regulator binding sites) and another nucleic acid sequence, such that the regulatory sequence regulates the transcription and/or translation of other nucleic acid sequences.

If a prokaryotic cell is a host, it generally includes a strong promoter capable of propagating transcription (e.g. tac promoter, lac promoter, lacUV5 promoter, lpp promoter, pL$\lambda$, promoter, pR$\lambda$, promoter, racy promoter, amp promoter, recA promoter, SP6 promoter, trp promoter and T7 promoter, etc.), a ribosome binding site for initiation of translation, and a transcription/translation termination sequence. In addition, for example, if a eukaryotic cell is used as a host, a promoter derived from the genome of a mammalian cell (e.g. metallothionein promoter, $\beta$-actin promoter, human hemogglobin promoter and human muscle creatine promoter) or promoters derived from mammalian viruses (e.g., adenovirus late promoter, vaccinia virus 7.5K promoter, SV40 promoter, cytomegalovirus (CMV) promoter, HSV tk promoter, mouse mammary tumor virus (MMTV) promoter, HIV LTR promoter, promoter of moloney virus, promoter of Epstein-Barr virus (EBV) and promoter of loose sarcoma virus (RSV)) can be used, and a polyadenylation sequence is included as a transcription termination sequence in general.

According to circumstances, the vector may be fused with other sequences to facilitate purification of the bispecific epitope binding protein expressed therefrom. The sequence to be fused includes, for example, glutathione S-transferase (Pharmacia, USA), maltose binding protein (NEB, USA), FLAG (IBI, USA), 6× His (hexahistidine; Qiagen, USA) and the like.

The vector contains an antibiotic resistance gene commonly used in the art as a selection marker. For example, these are genes resistant to ampicillin, gentamicin, carbenicillin, chloramphenicol, streptomycin, kanamycin, geneticin, neomycin, and tetracycline.

In another aspect, the present invention relates to a host cell transfected with the recombinant expression vector. The host cell used to produce the bispecific epitope binding protein of the present invention may be, but is not limited to, a prokaryotic, yeast or higher eukaryotic cell.

Prokaryotic host cells, such as *Escherichia coli, Bacillus* genus strains including *Bacillus subtilus* and *Bacillus thuringiensis, Streptomyces, Pseudomonas* (e.g. *Pseudomonas putida*), *Proteus mirabilis* and *Staphylococcus* (e.g. *Staphylocus carnosus*) may be used.

However, animal cells are of greatest interest, and the examples of useful host cell lines may be MDA-MB-231, MCF-7, FaDu, Jurkat, MC38, COS-7, BHK, CHO, CHOK1, DXB-11, DG-44, CHO/–DHFR, CV1, COS-7, HEK293, BHK, TM4, VERO, HELA, MDCK, BRL 3A, W138, Hep G2, SK-Hep, MMT, TRI, MRC 5, FS4, 3T3, R1N, A549, PC12, K562, PER.C6, SP2/0, NS-0, U20S, or HT1080 but not limited thereto.

In another aspect, the present invention relates to a method for preparing a bispecific epitope binding protein, comprising the steps of: culturing the host cell to generate a bispecific epitope binding protein; and isolating and purifying the resulting bispecific epitope binding protein.

The host cells can be cultured in various media. Commercially available media can be used as a culture medium without limitation. All other essential supplements known to those skilled in the art may be included in appropriate concentrations. Culture conditions, such as temperature, pH, etc. are already used with the host cells selected for expression and will be apparent to those skilled in the art.

For the recovery of the bispecific epitope binding protein, impurities may be removed by centrifugation or ultrafiltration, and the result may be purified using methods such as affinity chromatography. Other additional purification techniques such as anion or cation exchange chromatography, hydrophobic interaction chromatography, hydroxylapatite chromatography and the like may be used.

In another aspect, the present invention relates to a composition for preventing or treating a tumor or cancer, comprising the bispecific epitope binding protein.

The term "prevention" does not require absolute elimination of any breakthrough instance. The term "prevention" thus refers to any action of suppressing the clinical symptoms of a disease or delaying the progression by administration of the composition according to the present invention, and the term "treatment" refers to the inhibition of the development of clinical symptoms of the disease, or alleviation or elimination of clinical symptoms.

Pharmaceutically acceptable carriers included in the composition of the present invention are commonly used in formulation, and include lactose, dextrose, sucrose, sorbitol, mannitol, starch, acacia gum, calcium phosphate, alginate, gelatin, calcium silicate, microcrystalline cellulose, polyvinylpyrrolidone, water, syrup, methyl cellulose, methyl hydroxybenzoate, propyl hydroxybenzoate, talc, magnesium stearate, mineral oil, and the like, but are not limited thereto. The composition of the present invention may further include a lubricant, a wetting agent, a sweetening agent, a flavoring agent, an emulsifying agent, a suspending agent, a preservative, and the like, in addition to the above components.

The pharmaceutical composition of the present invention may be administered orally or parenterally, and in the case of parenteral administration, through intravenous injection, subcutaneous injection, intramuscular injection, intraperitoneal injection, endothelial administration, local administration, intranasal administration, intrapulmonary administration and rectal administration.

Since the protein or peptide is digested upon oral administration, oral compositions should be formulated to coat the active agent or to protect it from degradation in the stomach. In addition, the pharmaceutical composition may be administered by any device capable of transporting the active substance to a target cell.

A suitable dosage of the composition according to the present invention depends on factors such as formulation method, administration mode, patient's age, weight, sex, medical condition, food, administration time, administration route, excretion rate, and response sensitivity. An ordinarily skilled physician can readily determine and prescribe a dosage effective for the desired treatment or prophylaxis. For example, the daily dosage of the pharmaceutical composition of the present invention is 0.0001-100 mg/kg wherein the "kg" refers to the weight of the subject. The lower limit of the daily dosage may be 0.0001, 0.0005, 0.001, 0.005, 0.01, 0.05, 0.1, 0.5, 1, 2.5, 5, 7.5, 10, 12.5, 15, 17.5, 20, 22.5, 25, 27.5, 30, 32.5, 35, 37.5, and 40 mg/kg. The upper limit of the daily dosage may be 100, 97.5, 95, 92.5, 90, 87.5, 85, 82.5, 80, 77.5, 75, 72.5, 70, 67.5, 65, 62.5, 60, 57.5, 55, 52.5, 50, 47.5, 45, 42.5, and 40 mg/kg. Also embraced by the present invention is any range defined by a lower limit and an upper limit selected from the foregoing, as well as ranges wherein the values recited as a lower limit can serve as a upper limit (e.g., a range of 0.01 to 10 mg/kg is embraced by the present invention) and where a value recited as an upper limit can serve as a lower limit (e.g., a range of 45 to 75 mg/kg is embraced by the present invention). As used herein, the term "pharmaceutically effective dose" refers to a dose sufficient to prevent or treat cancer.

The pharmaceutical composition of the present invention may be prepared in a unit dose by formulating using a pharmaceutically acceptable carrier and/or excipient, or may be prepared by internalizing it in a multi-dose container, according to a method that can be easily carried out by a person of ordinary skill in the art to which the invention belongs. In this case, the formulation may be in the form of a solution in oil or aqueous medium, suspension or emulsion, or may be in the form of an extract, powder, suppository, granule, tablet or capsule. A dispersing agent or a stabilizing agent may be additionally included.

In some embodiments, the bispecific epitope binding protein, single-chain chimeric polypeptide, or nucleic acid constructs described herein may be used for treating a subject in need thereof.

In some embodiments, a pharmaceutical composition that includes a bispecific epitope binding protein, single-chain chimeric polypeptide and a pharmaceutically acceptable carrier can be administered to the subject diagnosed with a disease or condition.

In some embodiments, the subject has, or is at risk for developing cancer.

In some embodiments, the pharmaceutical composition can be administered with one or more additional anti-tumor therapies that include, but are not limited to, ionizing radiation, a chemotherapeutic agent, a therapeutic antibody, and a checkpoint inhibitor.

Cancer can refer to a broad group of diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. Cancer or cancer tissue may include a tumor.

Cancers suitable for treatment by a method of the present disclosure can include, but are not limited to, bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, and prostate cancer. In some embodiments, a cancer for treatment by a method of the present disclosure can include may include, but is not limited to, carcinoma, lymphoma (e.g., Hodgkin's and non-Hodgkin's lymphomas), blastoma, sarcoma and leukemia. In some embodiments, cancer may include squamous cell carcinoma, small cell lung cancer, non-small cell lung cancer, lung adenocarcinoma, squamous cell carcinoma of the lung, peritoneal cancer, hepatocellular carcinoma, gastric cancer, pancreatic cancer, glioma, cervical cancer, ovarian cancer, liver cancer, bladder cancer, hepatocellular carcinoma, breast cancer, colon cancer, colorectal cancer, endometrial or uterine carcinoma, salivary carcinoma, kidney cancer, prostate cancer, vulvar cancer, thyroid cancer, liver carcinoma, leukemia and other lymphoproliferative disorders, and various types of head and neck cancer.

Also provided herein are compositions (e.g., pharmaceutical compositions) that include at least one of any bispecific epitope binding proteins, single-chain chimeric polypeptides, any of the cells, or any of the nucleic acids described herein. In some embodiments, the compositions include at least one of any of the bispecific epitope binding proteins single-chain chimeric polypeptides described herein. In some embodiments, the compositions include any of the immune cells (e.g., any of the immune cells described herein, e.g., any of the immune cells produced using any of the methods described herein).

In some embodiments, the pharmaceutical compositions are formulated for different routes of administration (e.g., intravenous, subcutaneous). In some embodiments, the pharmaceutical compositions can include a pharmaceutically acceptable carrier (e.g., phosphate buffered saline).

Single or multiple administrations of pharmaceutical compositions can be given to a subject in need thereof depending on for example: the dosage and frequency as required and tolerated by the subject. The formulation should provide a sufficient quantity of active agent to effectively treat, prevent, or ameliorate conditions, diseases, or symptoms.

Also provided herein are kits that include any of the bispecific epitope binding proteins, single-chain chimeric polypeptides, compositions, nucleic acids, or cells (e.g., immune cells) described herein. In some embodiments, the kits can include instructions for performing any of the methods described herein. In some embodiments, the kits can include at least one dose of any of the pharmaceutical compositions described herein.

Definitions

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that are within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, "affinity" is a measure of the strength a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies, polyclonal antibodies, and fragments thereof. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE, or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); Anticalins®; Nanobodies minibodies; BiTE®s; ankyrin repeat proteins or DARPINs®; Avimers®; DARTs; TCR-like antibodies; Adnectins®; Affilins®; Trans-Bodies®; Affibodies®; TrimerX®; MicroProteins; Fynomers®, Centyrins®; and KALBITOR®s. In some embodiments, an antibody agent may lack a covalent modification (e.g., attachment of a glycan) that it would have if produced naturally. In some embodiments, an antibody agent may contain a covalent modification (e.g., attachment of a glycan, a payload [e.g., a detectable moiety, a therapeutic moiety, a catalytic moiety, etc.], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 80%, 81%, 82%, 83%, 84% 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 90%, 91%, 92%, 93%, 94%, 95%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain. In some embodiments, an antibody agent is or comprises at least a portion of a chimeric antigen receptor (CAR).

Antigen: The term "antigen", as used herein, refers to an agent that binds to an antibody agent. In some embodiments, an antigen binds to an antibody agent and may or may not induce a particular physiological response in an organism. In general, an antigen may be or include any chemical entity such as, for example, a small molecule, a nucleic acid, a polypeptide, a carbohydrate, a lipid, a polymer (including biologic polymers [e.g., nucleic acid and/or amino acid polymers] and polymers other than biologic polymers [e.g., other than a nucleic acid or amino acid polymer]) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some certain embodiments, an antigen is present in a cellular context (e.g., an antigen is expressed on the surface of a cell or expressed in a cell). In some embodiments, an antigen is a recombinant antigen.

Antigen binding domain: As used herein, refers to an antibody agent or portion thereof that specifically binds to a target moiety or entity. Typically, the interaction between an antigen binding domain and its target is non-covalent. In some embodiments, a target moiety or entity can be of any chemical class including, for example, a carbohydrate, a lipid, a nucleic acid, a metal, a polypeptide, or a small molecule. In some embodiments, an antigen binding domain may be or comprise a polypeptide (or complex thereof). In some embodiments, an antigen binding domain is part of a fusion polypeptide.

Associated with: Two events or entities are "associated" with one another, as that term is used herein, if the presence, level, and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Chemotherapeutic Agent: The term "chemotherapeutic agent", has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents (e.g., biofunctional alkylators such as Cyclophosphamide, Mechlorethamine, Chlorambucil, and Melphalan and monofunctional alkylators such as Dacarbazine, Nitrosoureas, Temozolomide), one or more anthracyclines (e.g., Daunorubicin, Doxorubicin, Epirubicin, Idarubicin, and Mitoxantrone), valrubicinone or more cytoskeletal disruptors (e.g. microtubule targeting agents such as taxanes, maytansine and analogs thereof, with specific examples including Paclitaxel, Docetaxel, Arabaxane, and Taxotere), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more vinca alkaloids, and/or one or more analogs of one or more of the following (i.e., that share a relevant anti-proliferative activity). In some particular embodiments, a chemotherapeutic agent may be or comprise one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine.

Engineered: In general, the term "engineered" refers to the aspect of having been manipulated by the hand of man. For example, a polypeptide is considered to be "engineered" when the polypeptide sequence manipulated by the hand of man. For example, in some embodiments of the present invention, an engineered polypeptide comprises a sequence that includes one or more amino acid mutations, deletions and/or insertions that have been introduced by the hand of man into a reference polypeptide sequence. In some embodiments, an engineered polypeptide includes a polypeptide that has been fused (i.e., covalently linked) to one or more additional polypeptides by the hand of man, to form a fusion polypeptide that would not naturally occur in vivo. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, derivatives and/or progeny of an engineered polypeptide or cell are typically still referred to as "engineered" even though the actual manipulation was performed on a prior entity.

Pharmaceutical composition: As used herein, the term "pharmaceutical composition" refers to a composition in which an active agent is formulated together with one or more pharmaceutically acceptable carriers. In some embodiments, the composition is suitable for administration to a human or animal subject. In some embodiments, the active agent is present in unit dose amount appropriate for administration in a therapeutic regimen that shows a statistically significant probability of achieving a predetermined therapeutic effect when administered to a relevant population.

Pharmaceutically acceptable carrier: In addition to the example given above, the term "pharmaceutically acceptable carrier", as used herein, generally has its art-recognized meaning of a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. The term "pharmaceutically acceptable carrier" may further include a pharmaceutically acceptable salt of the compound useful within the invention. Other additional ingredients that may be included in the pharmaceutical compositions used in the practice of the invention are described, for example, in Remington's Pharmaceutical Sciences (Genaro, Ed., Mack Publishing Co., 1985, Easton, Pa.), which is incorporated herein by reference. The "pharmaceutically acceptable carrier" is useful for the preparation of a pharmaceutical composition that is: generally compatible with the other ingredients of the composition, not deleterious to the recipient, and neither biologically nor otherwise undesirable. "A pharmaceutically acceptable carrier" includes one or more than one carrier. Embodiments include carriers for topical, ocular, parenteral, intravenous, intraperitoneal intramuscular, sublingual, nasal or oral administration. "Pharmaceutically acceptable carrier" also includes agents for preparation of aqueous dispersions and sterile powders for injection or dispersions.

Pharmaceutically acceptable salt: As used herein, the term "pharmaceutically acceptable salt" generally has its art-recognized meaning and refers to derivatives of the compounds provided herein wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by combining the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile may be used. Lists of suitable salts are found in Remington's Pharmaceutical Sciences, 17$^{th}$ ed., Mack Publishing Company, Easton, Pa., 1985, p. 1418 and Journal of Pharmaceutical Science, 66, 2 (1977), each of which is incorporated herein by reference in its entirety.

Excipient: As used herein, the term "excipient" generally has its art-recognized meaning and refers to physiologically compatible additives useful in preparation of a pharmaceutical composition. Examples of pharmaceutically acceptable carriers and excipients can, for example, be found in Remington Pharmaceutical Science, 16th Ed.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often at least about 50%, 60%, 70%, 80%, or 85% or greater and further usually including at least one region of much higher identity, often at least about 90%, 95%, 96%, 97%, 98%, or 99% or greater in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibody agents, antibody fragments, biologically active portions thereof, and/or characteristic portions thereof.

Recombinant: as used herein, is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silica. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

Specific binding: As used herein, the term "specific binding" refers to an ability to discriminate between possible binding partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically Effective Amount As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. For example, in some embodiments, term "therapeutically effective amount", refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy such as a pancreatic carcinoma or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor such as a pancreatic adenocarcinoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in any of the pro-angiogenic markers discussed above, an increase in anti-angiogenic markers described herein, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Variant: As used herein in the context of molecules, e.g., nucleic acids, proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence. In some embodiments, a variant polypeptide or nucleic acid shows an overall sequence identity with a reference polypeptide or nucleic acid that is at least 80%, 81%, 82%, 83%, 84%, 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid.

Vector: as used herein, and further to the disclosure above, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., *Molecular Cloning: A Laboratory Manual* $2^{nd}$ ed., Cold Spring Harbor Laboratory Press, Cold Spring Harbor, N.Y. (1989)), which is incorporated herein by reference for any purpose.

In the context of the present description, all publications, patent applications, patents and other references mentioned herein, if not otherwise indicated, are explicitly incorporated by reference herein in their entirety for all purposes as if fully set forth, and shall be considered part of the present disclosure in their entirety.

Unless otherwise defined, all technical and scientific terms used herein have the same meaning as commonly understood by one of ordinary skill in the art to which this disclosure belongs. In case of conflict, the present specification, including definitions, will control.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Without being bound to the following specific embodiments, the present invention is exemplified by the follow:

(1) A bispecific epitope binding protein which comprises a combination of (VH), (VL), (X), (VH)n, (VL)n, (X)n, (VH)n-Y, (VL)n-Y, (VH-VL)n-Y, (VL-VH)n-Y, (X)n-Y, Y-(VH)m, Y-(VL)m, Y-(VH-VL)m, Y-(VL-VH)m, and/or Y-(X)m, wherein VH and VL refer to a variable heavy region and a variable light region, respectively, of antibodies or antigen-binding fragments thereof that bind to 4-1BB, X is a PD-1 protein or fragment thereof that binds to PD-L1, Y refers to a fragment of the heavy chain constant region or the light chain constant region comprising one or more domain selected from the group consisting of CL, CH1, CH2, and CH3, and n and m are each an integer of 1 to 5.

(2) The bispecific epitope binding protein of (1), wherein (VH), (VL), (VH)n-Y, (VL)n-Y, (VH-VL)n-Y, (VL-VH)n-Y, (X)n-Y, Y-(VH)m, Y-(VL)m, Y-(VH-VL)m, Y-(VL-VH)m, and/or Y-(X)m, when present, may appear in any order from the N-terminus to the C-terminus.

(3) The bispecific epitope binding protein of (1) or (2), wherein when multiple copies of (VH), (VL), (VH)n-Y, (VL)n-Y, (VH-VL)n-Y, (VL-VH)n-Y, (X)n-Y, Y-(VH)m, Y-(VL)m, Y-(VH-VL)m, Y-(VL-VH)m, and/or Y-(X)m are present, they may be present in any order relative to the other regions and need not be directly adjacent to like kind regions.

(4) The bispecific epitope binding protein of any of (1) to (3), wherein the bispecific epitope binding protein is in scFv form.

(5) The bispecific epitope binding protein of any of (1) to (4), wherein said bispecific epitope binding protein has the structure of An-A'n'-B-Cm-C'm', wherein:
A, A', C, C': VH, VL, VH-VL, VL-VH or X
B: Y
VH, VL, X, Y, n, and m are as defined above and each of VH, VL, X, Y are connected directly or by a linker and/or a hinge, and
n' and m' are independently an integer of 1 to 5.

(6) The bispecific epitope binding protein of any of (1) to (4), wherein said bispecific epitope binding protein has the structure of An-B-Cm, wherein:
A or C: VH-VL, VL-VH or X
B: Y
VH, VL, X, Y, n, and m are as defined above and each of VH, VL, X, Y are connected directly or by a linker and/or a hinge.

(7) The bispecific epitope binding protein of any of (1) to (4), wherein a CH1 domain is C-terminally linked to (VH-VL)n, (VL-VH)n, or (X)n directly or by a hinge and/or a linker and a CH2/CH3 domain(s) is N-terminally linked to (VH-VL)m, (VL-VH)m, (X)m directly or by a hinge and/or a linker, wherein VH, VL, X, n, and m are as defined above.

(8) The bispecific epitope binding protein of (7), wherein the CH1 domain is linked to the CH2/CH3 domains(s) directly or by a hinge and/or linker.

(9) The bispecific epitope binding protein of any of (1) to (3), wherein said bispecific epitope binding protein comprises
a heavy chain comprising VH-VL, VL-VH, X, and/or VH-CH1 connected to CH2 directly or through a linker and/or a hinge and, independently, CH3 is connected to VH-VL, VL-VH or X directly or through a linker and/or a hinge and
a light chain comprising VL connected to CL via a linker and/or a hinge
wherein VH, VL, are X, are as defined above and each of VH, VL, X, CH1, CH2, CH3, and CL are connected directly or by a linker and/or a hinge.

(10) The bispecific epitope binding protein of any of (1) to (4), which comprises (VII and VL, in either order)n-Y and/or Y-(X)m,
wherein Y is independently a CH2 or CH3 domain, the VH, and VL and CH2 and/or CH3, or CH2 and/or CH3 and X are connected directly or through a hinge and/or a linker; and
VH, VL, X, n, and m are as defined above.

(11) The bispecific epitope binding protein of any of (1) to (4) and (10), wherein the bispecific epitope binding protein is a scFv arranged as (VL-VH)n-CH2-CH3-(X)m written from N-terminus to C-terminus.

(12) The bispecific epitope binding protein of (11), wherein VL and VH, VH and CH2, CH3 and (X)m, and/or CH2 and CH3 are connected directly or by a linker and/or a hinge.

(13) The bispecific epitope binding protein of any of (1) to (4), which comprises (X)m-Y and/or Y-(VH and VL, in either order)n,
wherein Y is independently a CI-12 or CH3 domain, the VII, and VL and CH2 and/or CH3, or CH2 and/or CH3 and X are connected directly or through a hinge and/or a linker; and
VH, VL, X, n, and m are as defined above.

(14) The bispecific epitope binding protein of (13), wherein the bispecific epitope binding protein is a scFv arranged as (X)m-CH2-CI-13-(VH-VL)n written from N-terminus to C-terminus.

(15) The bispecific epitope binding protein of (14), wherein (X)m and CH2, CH3 and VH, and VII and VL, and/or C112 and CH3 are connected directly or by a linker and/or a hinge.

(16) The bispecific epitope binding protein of any of (1) to (15), wherein each of n and m are individually selected from integers 1, 2, 3, 4, or 5 such that any combination of n and m having these integer values may be present.

(17) The bispecific epitope binding protein of any of (1) to (16), wherein where multiple VH, VL, and/or X are present (i.e., n and/or m is a value greater than 1) the copies are directly connected or separated by a hinge and/or a linker sequence.

(18) The bispecific epitope binding protein of (17), wherein copies are separated by a linker sequence.

(19) The bispecific epitope binding protein of any of (5) to (18), wherein the linker comprises about 10 to 25 amino acid residues, 10 to 20 amino acid residues, or 12 to 19 amino acid residues.

(20) The bispecific epitope binding protein of any of (5) to (19), wherein the linker is at least one selected from $(GS)_n$, $(GGS)_n$, $(GSGGS)_n$ or $(G_nS)_m$ (n and m are each 1 to 10), a 218 linker, or a 218S linker.

(21) The bispecific epitope binding protein of any of (5) to (20), wherein the linker is a $(G_4S)_3$ linker, a $(G_4S)_2$ linker, a 218 linker, or a 218S linker.

(22) The bispecific epitope binding protein of any of (1) to (21), wherein the 4-1BB-binding antibody or antigen-binding fragment thereof comprises VH of SEQ ID NO: 23.

(23) The bispecific epitope binding protein of any of (1) to (22), wherein the 4-1BB-binding antibody or antigen-binding fragment thereof comprises VL of SEQ ID NO: 25.

(24) The bispecific epitope binding protein of any of (1) to (21), wherein the 4-1BB-binding antibody or antigen-binding fragment thereof comprises VH of SEQ ID NO: 23 and VL of SEQ ID NO: 25.

(25) The bispecific epitope binding protein of any of (1) to (24), wherein the PD-1 protein or fragment thereof comprises the sequence of SEQ ID NO: 27.

(25) The bispecific epitope binding protein of any of (1) to (21), wherein the 4-1BB-binding antibody or antigen-binding fragment thereof comprises VH of SEQ ID NO: 23 and VL of SEQ ID NO: 25 and the PD-1 protein or fragment thereof comprises the sequence of SEQ ID NO: 27.

(27) The bispecific epitope binding protein of any of (1) to (26), wherein said bispecific epitope binding protein has a sequence selected from the group consisting of SEQ ID NOs: 1-10 and 14 or said bispecific epitope binding protein has at least 80% sequence identity to a bispecific epitope binding protein having a sequence selected from the group consisting of SEQ ID NOs: 1-10 and 14 and which has bispecific binding affinity for 4-1BB and PD-L1.

(28) The bispecific epitope binding protein of any of (1) to (26), wherein said bispecific epitope binding protein has a sequence selected from the group consisting of SEQ ID NOs: 1-10 and 14.

(29) The bispecific epitope binding protein of any of (1) to (26), wherein said bispecific epitope binding protein has at least 80% sequence identity to a bispecific epitope binding protein having a sequence selected from the group consisting of SEQ ID NOs: 1-10 and 14 and which has bispecific binding affinity for 4-1BB and PD-L1.

(30) The bispecific epitope binding protein of any of (1) to (26), wherein said bispecific epitope binding protein has a sequence of SEQ ID NO: 3.

(31) The bispecific epitope binding protein of any of (1) to (26), wherein said bispecific epitope binding protein has at least 80% sequence identity to a bispecific epitope binding protein having a sequence of SEQ ID NO: 3 and which has bispecific binding affinity for 4-1BB and PD-L1.

(32) The bispecific epitope binding protein of any of (1) to (31), further comprising a signal peptide.

(33) The bispecific epitope binding protein of (32), wherein said signal peptide is an N-terminal signal peptide comprising 12 to 40 amino acids.

(34) The bispecific epitope binding protein of any of (5) to (33), wherein the hinge has a sequence of SEQ ID NO: 30 or SEQ ID NO: 31.

(35) The bispecific epitope binding protein of any of (5) to (34), wherein the hinge has a sequence of SEQ ID NO: 31.

(36) The bispecific epitope binding protein of any of (1) to (35), wherein the PD-1 protein or fragment thereof is affinity matured.

(37) A pair of bispecific epitope binding proteins of any of (1) to (36), wherein both members of the pair are the same.

(38) A nucleic acid molecule encoding the bispecific epitope binding protein of any of (1) to (36).

(39) A recombinant vector comprising the nucleic acid molecule of (38).

(40) A cell comprising the nucleic acid molecule of (38) or the recombinant vector of (28).

(41) A method of producing a bispecific epitope binding protein, the method comprising: culturing the cell of (40) in a culture medium under conditions sufficient to result in the production of the bispecific epitope binding protein; and recovering the bispecific epitope binding protein from the cell and/or the culture medium.

(42) A pharmaceutical composition comprising the bispecific epitope binding protein of any of (1) to (36), a nucleic acid of (38), a recombinant vector of (39), or a cell of (40) and pharmaceutically acceptable carrier.

(43) A kit comprising the pharmaceutical composition of (42).

(44) A method of treating cancer in a subject in need thereof, the method comprising:
administering to the subject a composition that comprises or delivers an effective amount of the bispecific epitope binding protein of any of (1) to (36), a nucleic acid of (37), a recombinant vector of (38), or a cell of (40).

(45) The method of (44), wherein the subject has cancer.

(46) The method of (44), wherein the subject is at risk for developing cancer.

(47) The method of any of (44) to (46), wherein the cancer comprises a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, prostate cancer, and combinations thereof.

(48) A method of preventing cancer in a subject in need thereof, the method comprising:
administering to the subject a composition that comprises or delivers an effective amount of the bispecific epitope binding protein of any of (1) to (36), a nucleic acid of (38), a recombinant vector of (39), or a cell of (40).

(49) The method of (48), wherein the subject has cancer.

(50) The method of (48), wherein the subject is at risk for developing cancer.

(51) The method of any of (48) to (50), wherein the cancer comprises a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, prostate cancer, and combinations thereof.

(52) The method of any of (48) to (51), wherein preventing is inhibition of the development of clinical symptoms of cancer.

(53) The method of any of (48) to (51), wherein preventing is alleviation of clinical symptoms associated with cancer.

(54) The method of any of (47) to (50), wherein preventing is elimination of clinical symptoms associated with cancer.

Having generally described this invention, a further understanding can be obtained by reference to certain specific examples, which are provided herein for purposes of illustration only, and are not intended to be limiting unless otherwise specified.

EXAMPLES

The disclosure is further described in the following examples, which do not limit the scope of the disclosure described in the claims.

Example 1: Bispecific Antibody (BsAB) Design and Production

Figure 2:
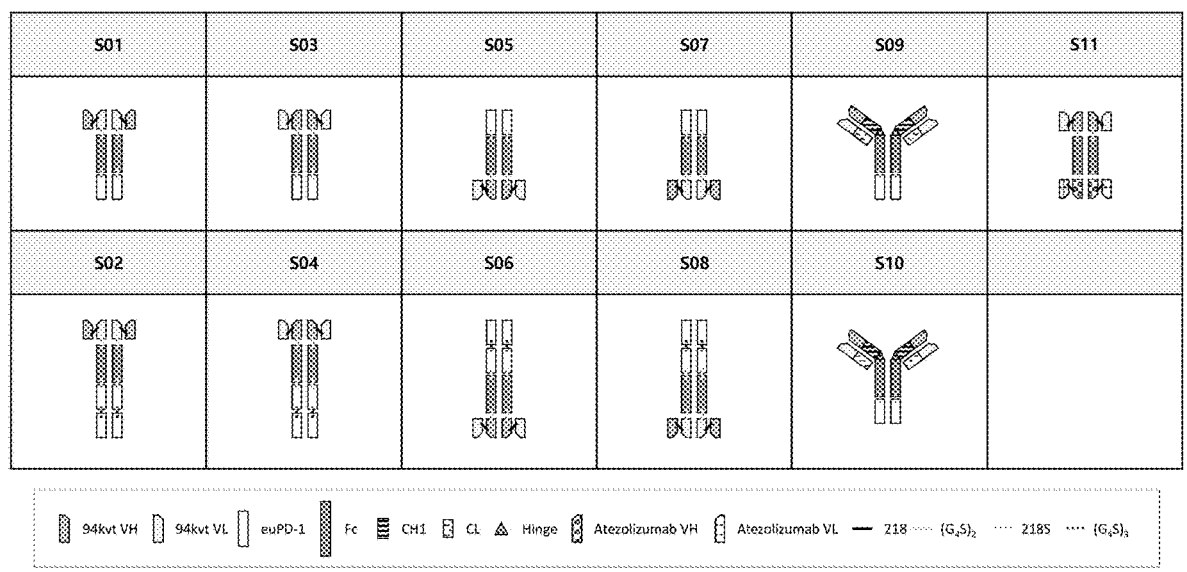
FIG. 2 shows designs of for bispecific epitope binding proteins S01-S11 described in Example 1.

For anti-4-1BB antibody, a 94kvt clone was used (EU101 as described in WO2018-127787, incorporated herein by reference in its entirety), and for anti-PD-L1 protein, affinity matured PD-1 protein (euPD-1, EU131 as described in U.S. Ser. No. 17/469,549, incorporated herein by reference in its entirety) was used. A total of 10 (S01-S10) anti-4-1BB antibody x euPD-1 variants (referred to herein as "bispecific epitope binding protein variants") were designed (SEQ ID NO: 1-10, 14; bispecific epitope binding proteins SOI-S10 and 94kvt Light chain respectively) by changing the arrangement, and $(G_4S)_3$, $(G_4S)_2$, and 218 or 218S (SEQ ID NO:15-18) were used as the linker to connect each part. For 94kvt, the scFv form was used. A hinge and an Fc part of engineered IgG1 was used to link with euPD-1. For Fc, point mutations (L234A, L235A, K322A, D356E, L358M) were introduced to reduce ADCC and CDC. (FIG. 2)

In addition, S11 (SEQ ID NO: 11) antibody is developed by attaching an approved and commercially available anti-PD-L1 antibody (Atezolizumab, Genentech) in an scFv form to the C-terminal of antibody to use as control. (FIG. 2)

Expression of the generated bispecific antibodies was performed using the Expi293F expression system (Invitrogen) or the ExpiCHO expression system (ThermoFisher scientific). Purification was performed using AktaPure (cytiva) instrument, a protein A column (Hitrap MabSelectSure, cytiva, Cat. no. 11003495) and a desalting column (Hiprep 26/10 Desalting, Cytiva Cat. no. 17508702).

Example 2: SDS-PAGE Analysis of the Bispecific Epitope Binding Protein Variants

Figure 3:
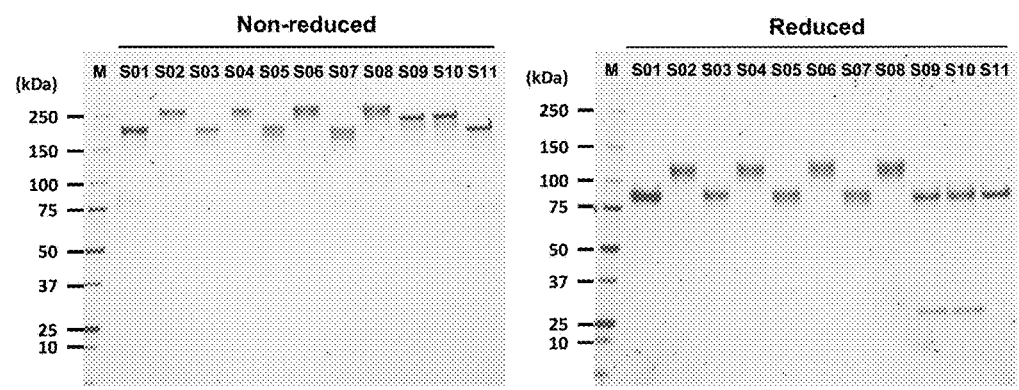
FIG. 3 shows the results of SDS-PAGE analysis (see Example 2) for bispecific epitope binding proteins S01-S11 under non-reducing and reducing conditions.
Figure 4A:
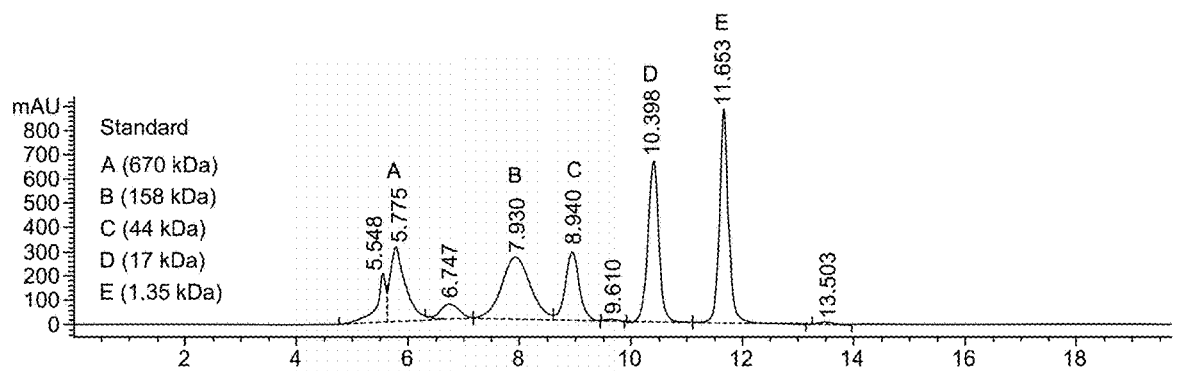
FIGS. 4A-4L show the results of size-exclusion chromatography (see Example 3) for bispecific epitope binding proteins S01-S11.
Figure 4B:
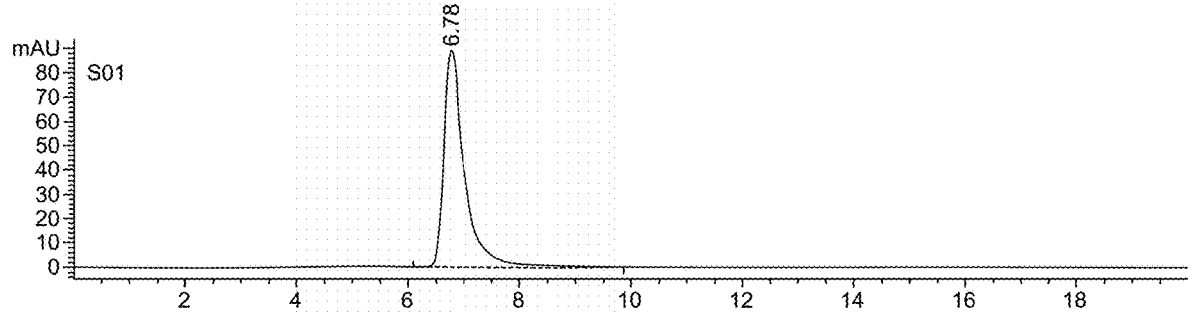
Figure 4C:
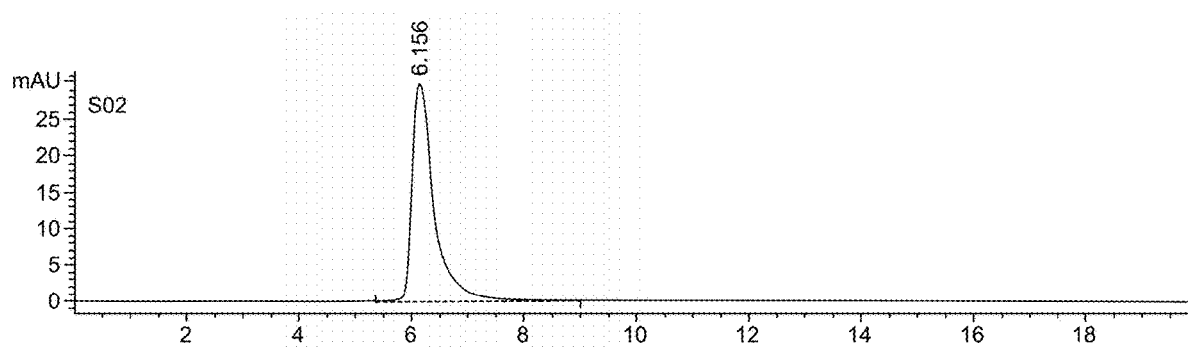
Figure 4D:
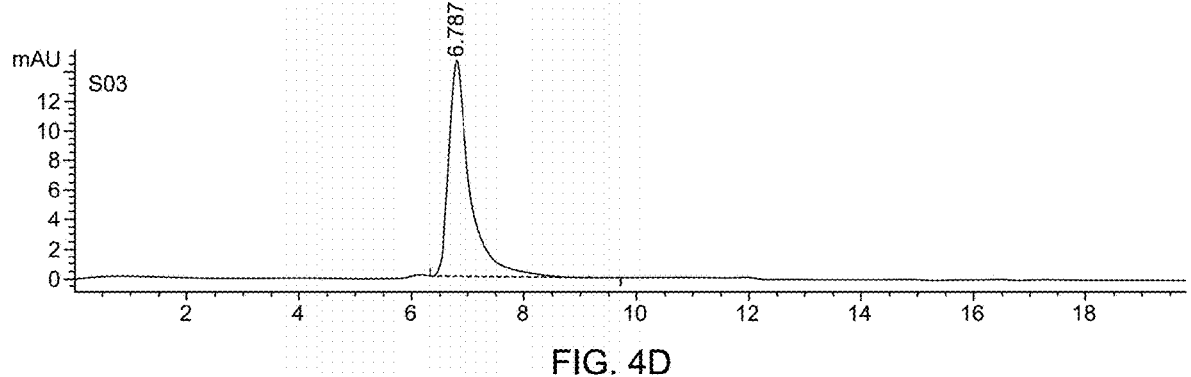
Figure 4E:
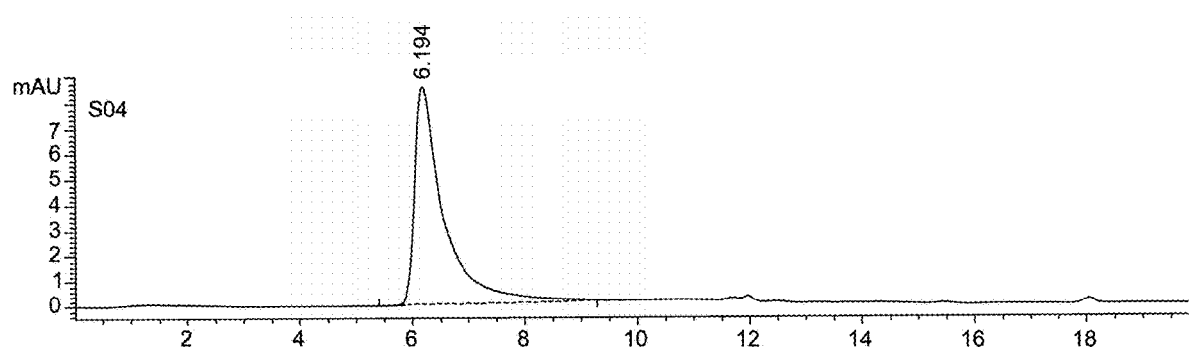
Figure 4F:
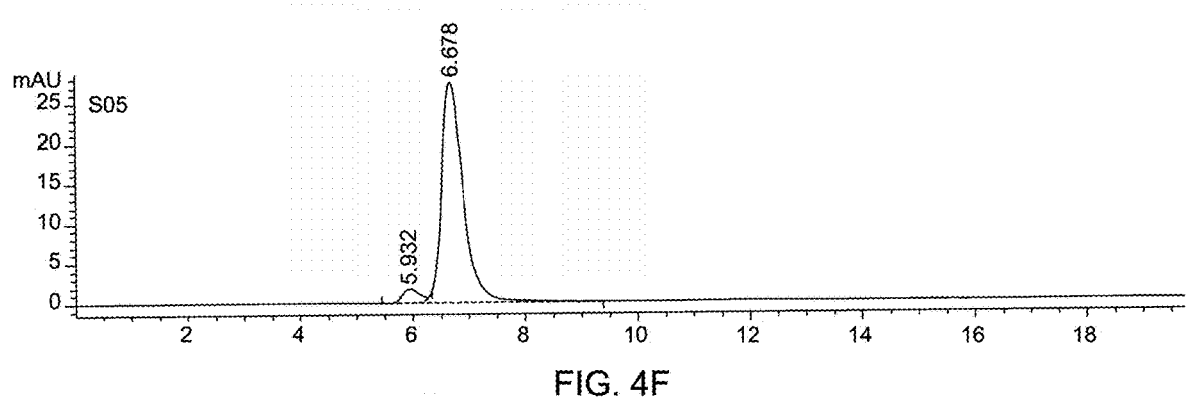
Figure 4G:
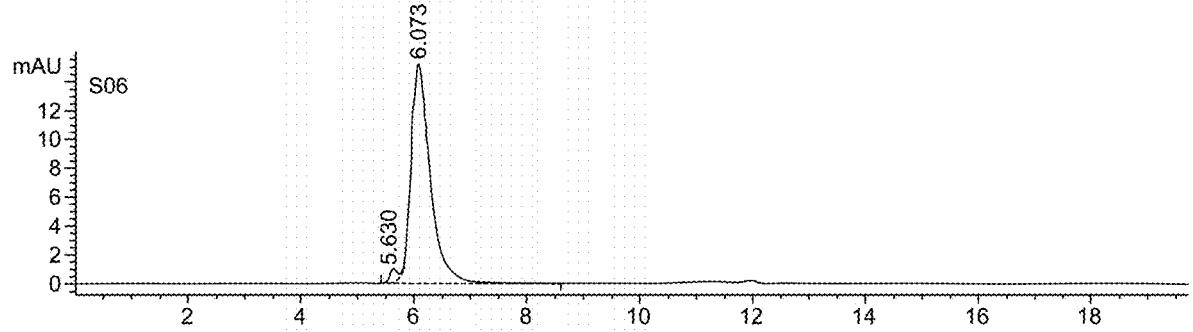
Figure 4H:
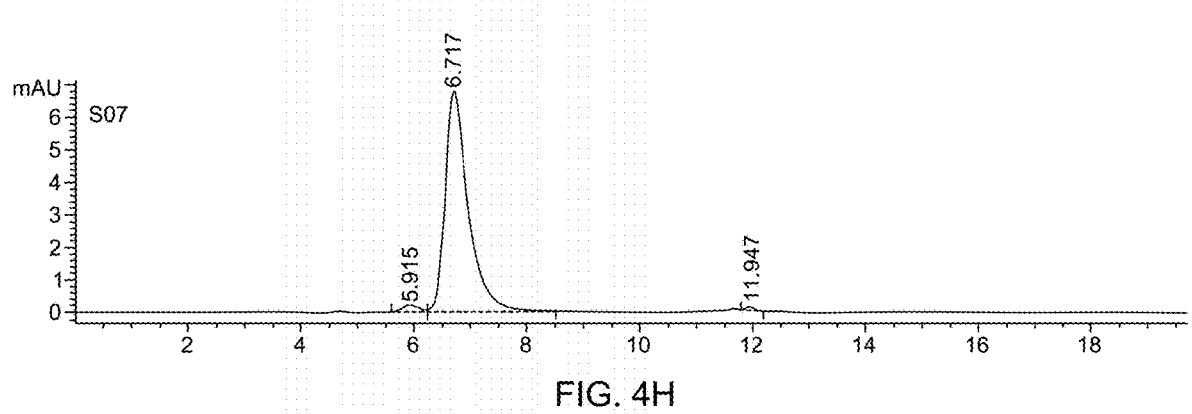
Figure 4I:
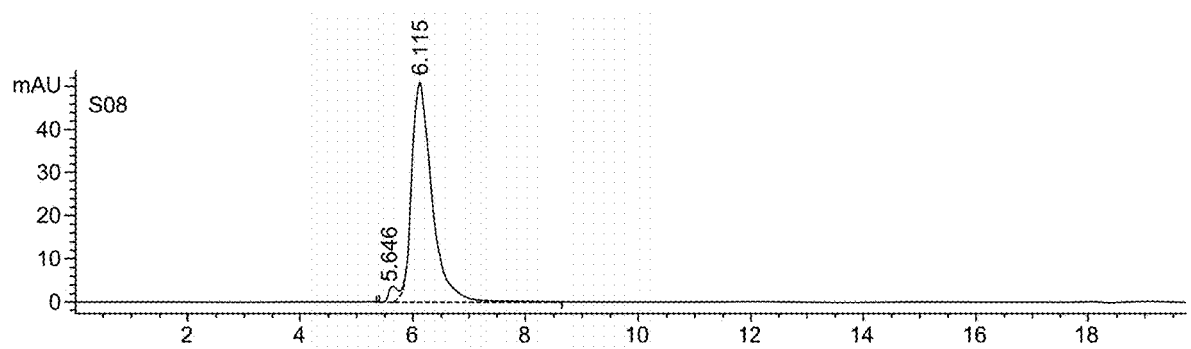
Figure 4J:
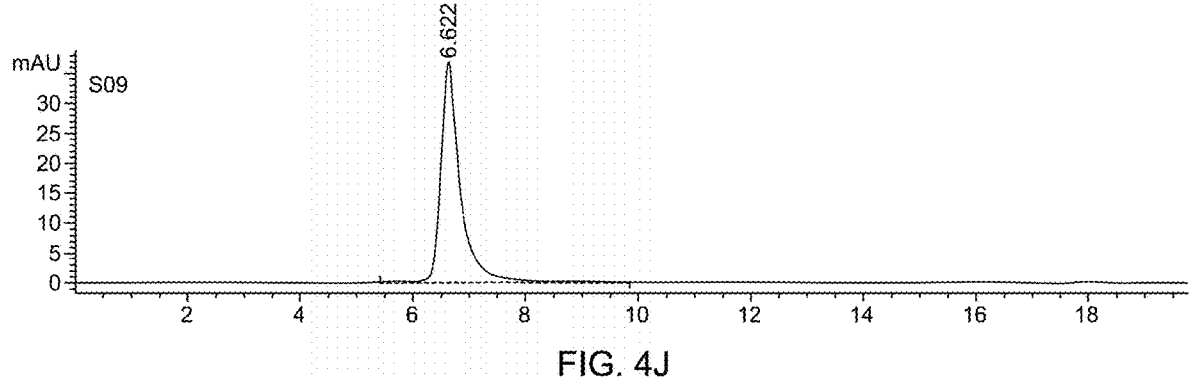
Figure 4K:
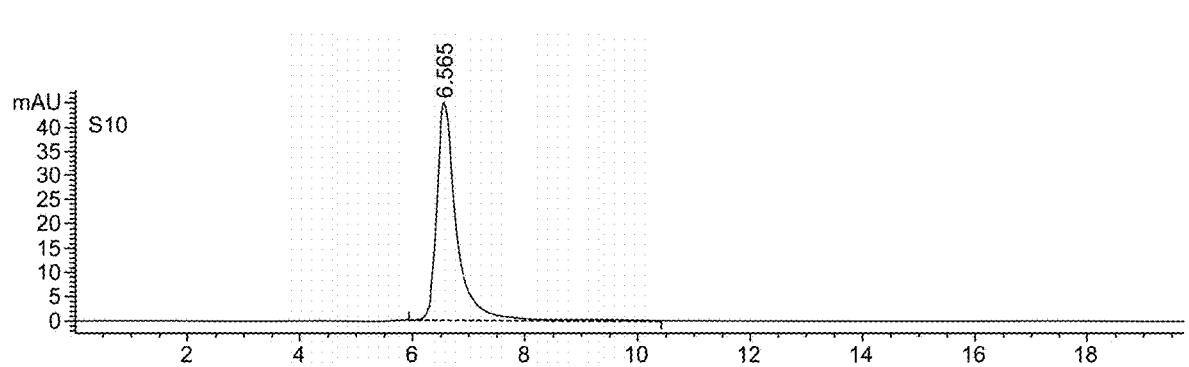
Figure 4L:
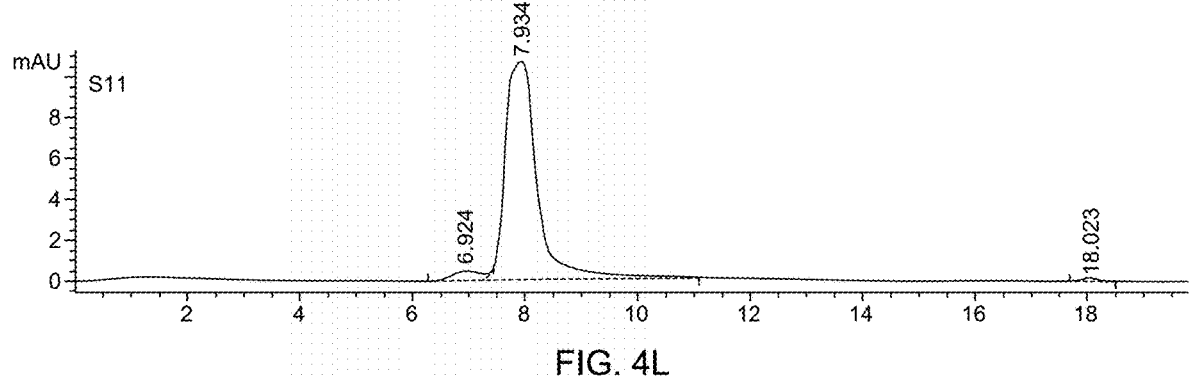

SDS-PAGE analysis was performed to analyze the bispecific epitope binding protein variants under reducing and non-reducing conditions. The reducing condition is to add 1 μg of bispecific epitope binding protein variants to LDS sample buffer (Invitrogen, Cat. No. NP0007) with a sample reducing agent (Thermo, Cat. No. NP0009). Boiling was subsequently performed for 3 min at 95° C. For the non-reducing conditions, only LDS sample buffer was added and used. After loading the produced sample on Mini-PROTEAN TGX stain-free gel (Bio-rad), the gel was run in 1× Tris/Glycine/SDS buffer (Bio-rad, Cat. No. 1610732) at 125 V for 30 min. The results were analyzed with Chemidoc (Bio-rad) and are shown in FIG. 3.

Example 3: Size-Exclusion Chromatography Analysis of Bispecific Epitope Binding Protein Variants The bispecific epitope binding protein variants were also subjected to SEC analysis using an HPLC instrument (Agilent Technologies, 1260 infinity II LC system) and a size exclusion column (Tosoh, TSKgel G3000 SWXL, 7.8×300 mm, Part No. 0008541, Column No. 004E04320E). Gel filtration standard (Bio-rad, Cat no. 1511901) was used as a control. The results are shown in FIGS. 4A-4L.

Example 4: Analyzing the Affinity of Bispecific Epitope Binding Protein Variants Surface plasmon resonance (SPR) was used to analyze the affinity of the bispecific epitope binding protein variants.

Affinity for 4-1BB

Affinity to 4-1BB was determined using the bispecific epitope binding protein variants diluted to 5 μg/ml and then fixed to CM5 chip (Cytiva, BR-1005-30) with human capture (Cytiva, Cat. No. BR-1008-39). The 4-1BB antigen (abclon) was injected at concentrations of 100, 50, 25, 12.5, 6.25, and 3.125 nM, the association time was set to 150 seconds, and the dissociation time was set to 240 seconds. Biacore T200 (cytiva) was used as the analysis equipment. The result of the 4-1BB affinity assessment is provided in Table 1:

TABLE 1

| | Affinity to 4-1BB | | |
|---|---|---|---|
| No. | Ka (1/Ms) | Kd (1/s) | KD (nM) |
| S01 | 1.61E+05 | 5.37E−04 | 3.34 |
| S02 | 1.79E+05 | 6.58E−04 | 3.67 |
| S03 | 2.08E+05 | 6.34E−04 | 3.05 |
| S04 | 2.31E+05 | 6.62E−04 | 2.87 |
| S05 | 1.27E+05 | 4.66E−04 | 3.66 |
| S06 | 2.45E+05 | 9.14E−04 | 3.72 |
| S07 | 6.43E+03 | 6.76E−04 | 105.2 |
| S08 | 1.12E+05 | 7.64E−04 | 6.83 |
| S09 | 2.61E+05 | 5.68E−04 | 2.17 |
| S10 | 2.62E+05 | 6.01E−04 | 2.3 |
| S11 | 2.06E+05 | 4.42E−04 | 2.14 |

Affinity for PD-L1

Affinity to PD-L1 was determined using the bispecific epitope binding protein variants diluted to 10 μg/ml and then fixed to CM5 chip with human capture. PD-L1 antigen (SinoBiologics, Cat. No. 10084-H08H) was injected at concentrations of 100, 50, 25, 12.5, 6.25, and 3.125 nM, and the subsequent procedure was the same as the 4-1BB affinity analysis procedure. The result of the PD-L1 affinity assessment is provided in Table 2:

TABLE 2

| | Affinity to PD-L1 | | |
|---|---|---|---|
| No. | Ka (1/Ms) | Kd (1/s) | KD (nM) |
| S01 | 2.30E+05 | 1.32E−03 | 5.73 |
| S02 | 3.24E+05 | 1.32E−03 | 4.06 |
| S03 | 2.27E+05 | 1.15E−03 | 5.07 |
| S04 | 5.96E+05 | 1.40E−03 | 2.34 |
| S05 | 1.46E+06 | 1.69E−03 | 1.16 |
| S06 | 8.37E+05 | 1.86E−03 | 2.22 |
| S07 | 1.00E+06 | 1.58E−03 | 1.58 |
| S08 | 8.37E+05 | 1.86E−03 | 2.22 |
| S09 | 2.09E+05 | 1.31E−03 | 6.26 |
| S10 | 3.77E+05 | 1.41E−03 | 3.73 |
| S11 | 7.11E+04 | 5.53E−05 | 0.78 |

Figure 5A:
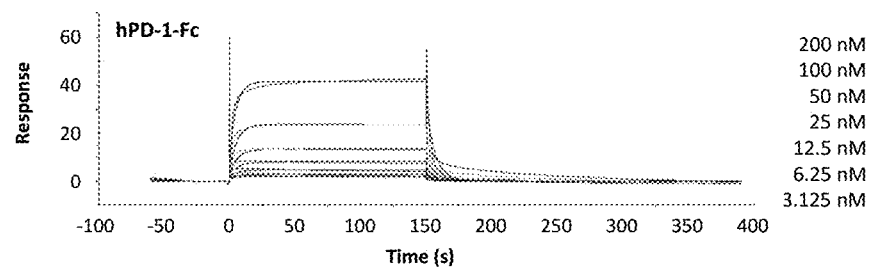
FIG. 5A shows the results of surface plasmon resonance assays for human PD1-Fc binding to PD-L1.
Figure 5B:
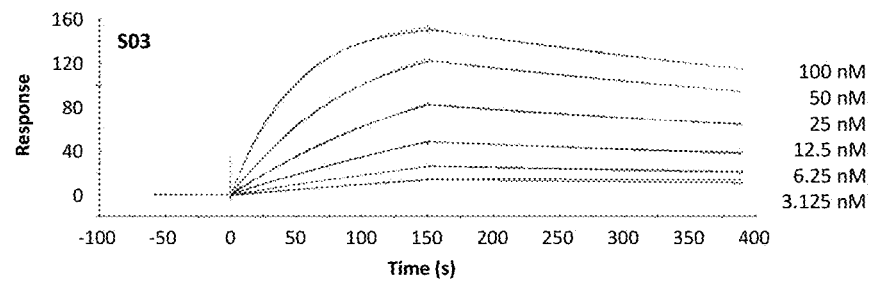
FIG. 5B shows the results of surface plasmon resonance assays for S03 binding to PD-L1. (See Example 4)

For comparison of binding differences to PD-L1 between natural PD-1 and S03 and binding of mouse PD-1 and human PD-L1, human PD-1-Fc (SinoBiologics) and mouse PD-1 Fc (SinoBiologics, Cat No. 50124-M02H) were diluted to 15 μg/ml and fixed to a CM5 chip with human capture. PD-L1 antigen was injected at concentrations of 200, 100, 50, 25, 12.5, 6.25, and 3.125 nM, and the subsequent procedure was the same as the 4-1BB affinity analysis procedure. The results are shown in FIG. 5A for human natural PD1-Fc and FIG. 5B for S03. It was identified that S03 binds to PD-L1 approximately 93 times stronger than natural PD-1 does. Also, no affinity by mouse PD-1 to human PD-L1 was identified (see Table 3).

TABLE 3

| | Affinity to PD-L1 | | |
|---|---|---|---|
| | ka (1/Ms) | Kd (1/s) | KD (nM) |
| Mouse PD1-Fc | Not detected | | |
| Human PD1-Fc | 3.13E+05 | 1.48E−01 | 471.40 |
| S03 | 2.27E+05 | 1.15E−03 | 5.07 |

Example 5: Single Antigen Binding ELISA

Figure 6A:
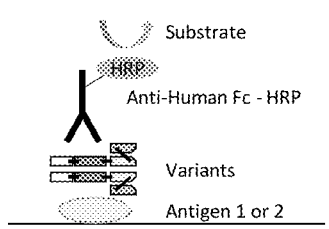
FIG. 6A shows the assay method for the single antigen binding ELISA in Example 5.

Single antigen binding ELISA was performed to confirm whether the bispecific epitope binding protein variants bind to each target antigen. The assay method was performed as shown in FIG. 6A.

Figure 6B:
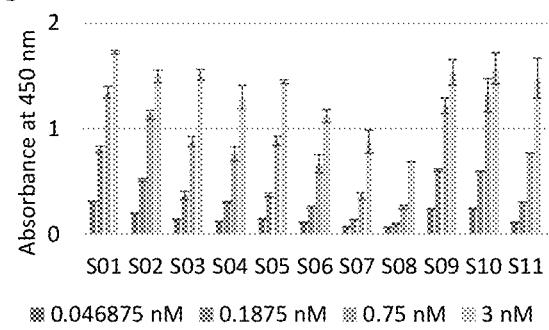
FIG. 6B shows the results of bispecific epitope binding proteins S01-S11 binding to 4-1BB.

To identify 4-1BB binding, 96-well immuno plate was coated with 4-1BB antigen (abclon) of 1 at 4° C. overnight and added with 150 μl of 1× assay buffer (BioLegend) for 1 hour to block non-specific binding. After four-fold serial dilution of the bispecific epitope binding protein variants from 3 nM for 4 points, and 100 μl per well was treated for 2 hours. Next, HRP-conjugated anti-human IgG, Fcγ antibody (Jackson Immunoresearch, Cat. No. 10-035-008) was diluted 2000 times and 100 μl was added to each well for incubation for 1 hour. After color development with TMB, the reaction was stopped using sulfuric acid. Washing was performed 3 times using washing buffer in all processes except for the processes after TMB treatment, and all processes except for the coating process were carried out at room temperature. (FIG. 6B)

Figure 6C:
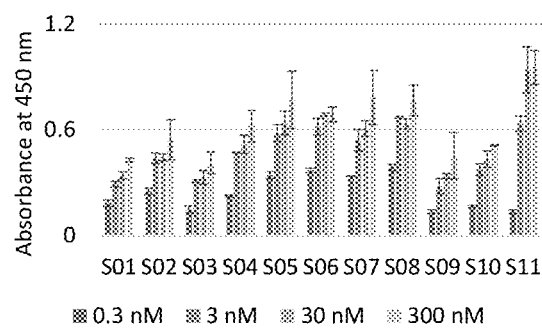
FIG. 6C shows the results of bispecific epitope binding proteins S01-S11 binding to PD-L1.

In order to identify PD-L1 binding, 96-well immuno plate was coated with PD-L1 antigen (SinoBiologics) of 1 μg/ml at 4° C. overnight, and added with 150 μl of 1× assay buffer (BioLegend) for 1 hour to block non-specific binding. The bispecific epitope binding protein variants were serially diluted ten-fold from 300 nM for 4 points, and 100 μl per well was treated for 2 hours. The other procedures after this were the same as those of the 4-1BB binding ELISA. (FIG. 6C)

Figure 6D:
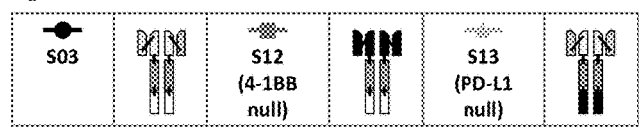
FIG. 6D shows bispecific antibody design of bispecific epitope binding proteins S03 and the null variants S12 (4-1BB null) and S13 (PD-L1 null).

In addition, in order to identify whether it was a specific binding by each antigen binding part, i) S12 (SEQ ID NO: 12) was produced by substituting the anti-4-1 BB antibody of S03 with human germline antibody (DP47) to prevent binding to 4-1BB, ii) S13 (SEQ ID NO: 13) was produced by point mutating the euPD-1 of S03 and substituting it with euPD-ln to prevent binding to PD-L1 and the single antigen binding ELISA for 4-1BB and PD-L1 was performed. (FIG. 6D)

Figure 6E:
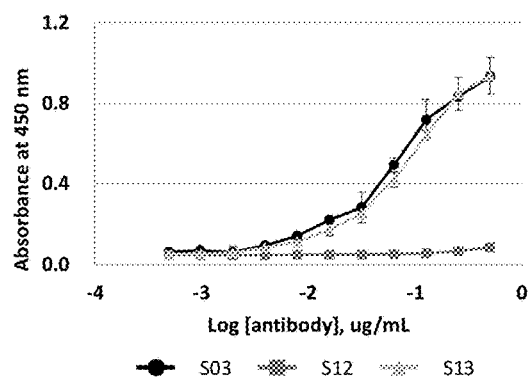
FIG. 6E shows the results of bispecific epitope binding protein S03, as well as null variants S12 and S13, binding to 4-1BB.

As for 4-1BB binding, a total of 11 points were identified by twofold serial dilution of S03, S12, and S13 from 0.5 μg/ml. It was identified that S12 without anti-4-1BB antibody failed to bind to 4-1BB, and S03 and S13 bound to the 4-1BB dose-dependently. (FIG. 6E)

Figure 6F:
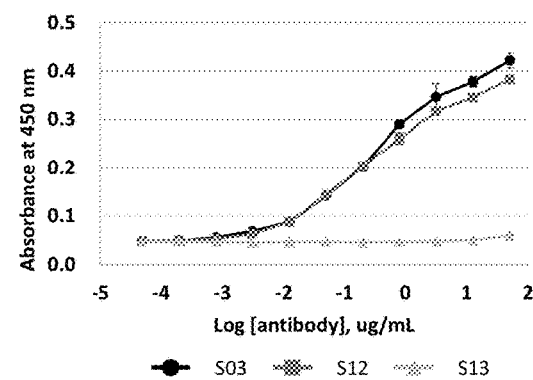
FIG. 6F shows the results of bispecific epitope binding protein S03, as well as null variants S12 and S13, binding to PD-L1.

For PD-L1 binding, a total of 11 points were identified by four-fold serial dilution of S03, S12, and S13 from 100 μg/ml. It was noted that S13, which was point mutated so as not to be able to bind to PD-L1, did not bind to PD-L1, whereas S03 and S12 bound to PD-L1 dose-dependently. (FIG. 6F)

Example 6: Dual Antigen Binding ELISA

A dual binding assay was performed to identify that the bispecific epitope binding protein variants bind to both antigen 4-1BB and PD-L1.

Figure 7A:
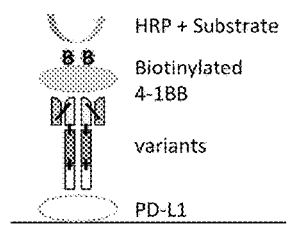
FIG. 7A shows the assay method for the dual antigen binding ELISA in Example 6.
Figure 7B:
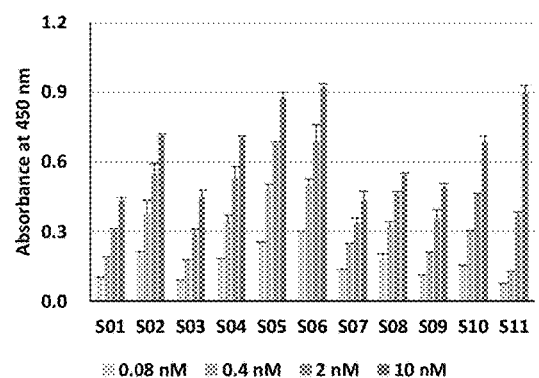
FIG. 7B shows the results of the dual antigen binding ELISA for bispecific epitope binding proteins S0I-S11.

The assay method was performed as shown in FIG. 7A. In brief, a 96-well immuno plate was coated with PD-L1 antigen (SinoBiologics) of 1 μg/ml at 4° C. overnight, and added with 150 μl of 1× assay buffer (BioLegend) for 1 hour to block non-specific binding. A five-fold serial dilution of the bispecific epitope binding protein variants was performed from 10 nM for 4 points, 100 μl per well was treated for 2 hours, and 100 μl of biotinylated 4-1BB antigen (SinoBiologics, Cat. No. 10041-H08H-B) at a concentration of 0.1 μg/ml was added to each well for incubation for 1 hour. Next, avidin-HRP (BioLegend, Cat No. 79004) was diluted 1/1000, added to each well by 100 μl for treatment for 30 minutes, color development with TMB was carried out, and the reaction was stopped using sulfuric acid. Washing was performed 3 times using the washing buffer in all processes except for the process after TMB addition, and all processes except for the coating process were carried out at room temperature. (FIG. 7B)

Figure 7C:
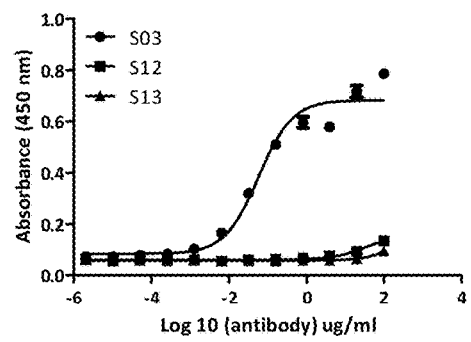
FIG. 7C shows the results of the dual antigen binding ELISA for bispecific epitope binding protein S03, the null variants S12 (4-1BB null) and S13 (PD-L1 null).

Dual antigen ELISA for S03, S12 and S13 was also performed using five-fold serial dilution from 100 μg/ml for 12 points to identify a specific binding by each antigen binding part. It can be seen that S12 without anti-4-1BB antibody and S13 which were point mutated to prevent binding to PD-L1 did not show dual antigen binding, but S03 bound dose-dependently. (FIG. 7C)

Example 7: Cell Binding Assay

MDA-MB-231-Luc (human breast cancer cell, JCRB, JCRB1559), FaDu (human squamous cell carcinoma cell, ATCC, HTB-43) which are PD-L1 positive cell line, 4-1BB Jurkat (in-house generated) which is 4-1BB positive cell line, and MCF-7 (human breast cancer cell) which is PD-L1 and 4-1BB negative cell line were used for the assay. FIG. 8 shows the expression levels of 4-1BB and PD-L1 in each cell line. It was determined that there was almost no background signal by the second antibody.

$2 \times 10^5$ cells from each cell line were treated with bispecific epitope binding protein variants at a final concentration of 50, 5, 0.5, and 0.05 nM, and then incubated at 4° C. for 20 min. Next, washing was carried out once by using FACS washing buffer and 1 μl/tube of anti-hFC-488 $2^{nd}$ antibody (Jackson ImmunoResearch) was added for treatment for 20 min. After washing twice, analysis was performed using FACS (FACSCelesta, BD).

Figure 9A:
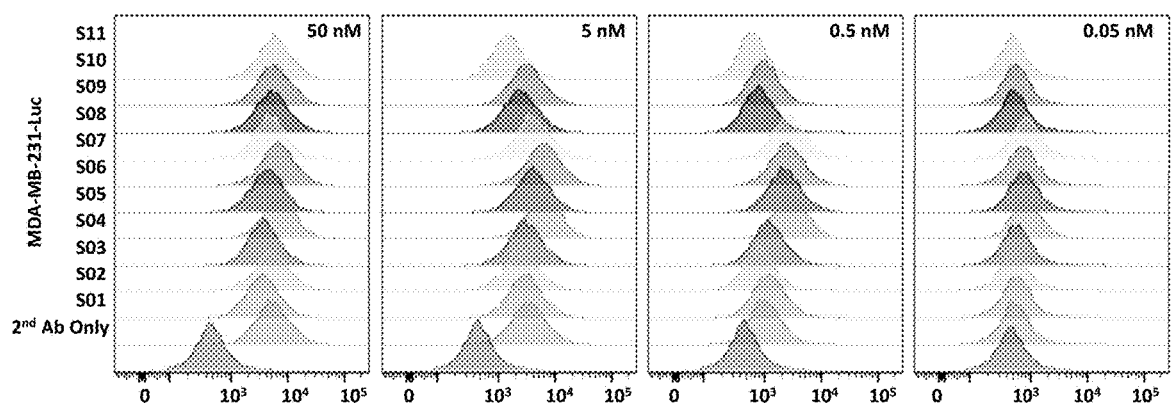
FIG. 9A (MDA-MB-231-Luc) and FIG. 9B (FaDu) show the results of FACS analysis for the bispecific epitope binding protein variants with PD-L1 positive cell line.
Figure 9B:
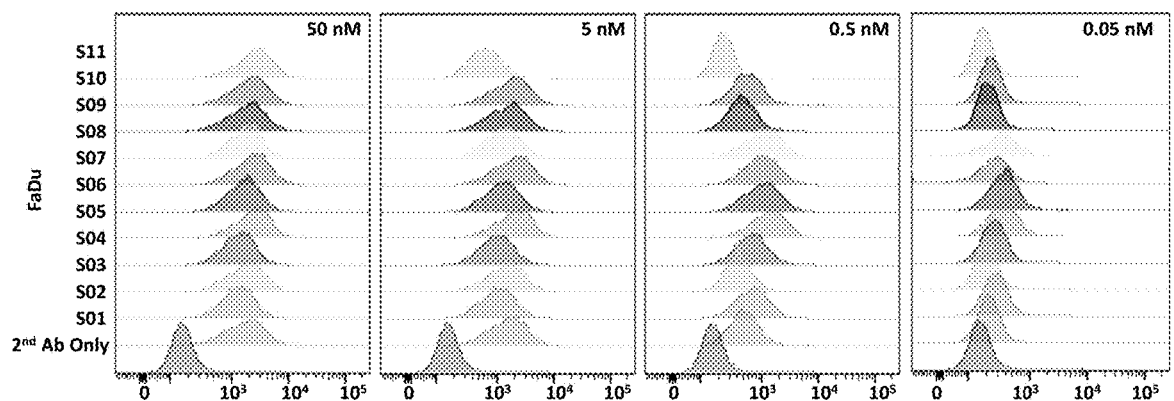
FIG. 9C (4-1BB Jurkat) shows the results of FACS analysis for the bispecific epitope binding protein variants with 4-1BB positive cell line.
FIG. 9D (MCF-7) shows the results of FACS analysis for the bispecific epitope binding protein variants with a PD-L1 and 4-1 BB negative cell line. (see Example 7)
Figure 9C:
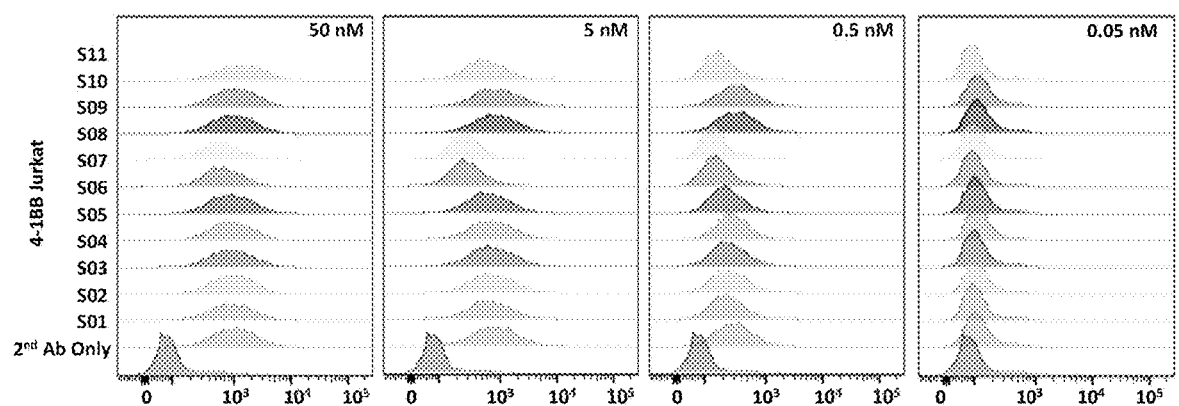
Figure 9D:
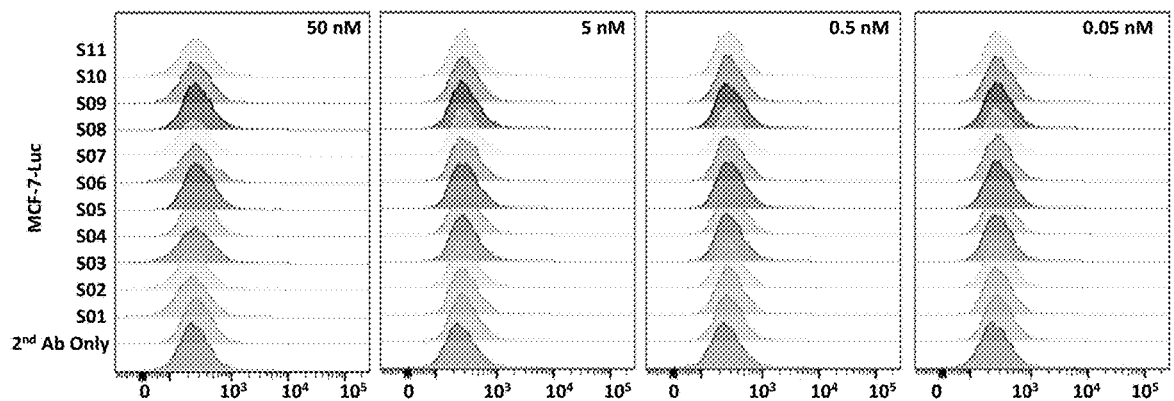

As a result of FACS analysis, it was found that the bispecific epitope binding protein variants bound to PD-L1 (FIGS. 9A-B) and 4-1BB positive cell line (FIG. 9C) dose-dependently. In addition, they did not bind to cells that did not express both 4-1BB and PD-L1 (FIG. 9D), Example 8: 4-1BB Bioassay To verify the 4-1BB activity effect, a 4-1BB bioassay (Promega, J2332) was performed according to the principle that luciferase is expressed when 4-1BB of effector cell is activated.

Figure 10:
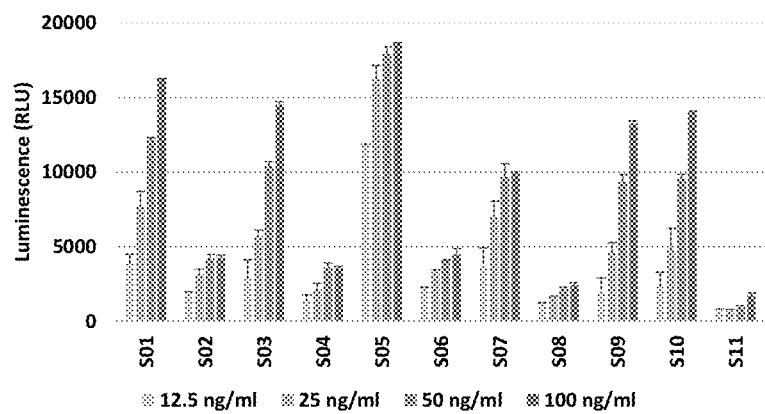
FIG. 10 shows the results of a 4-1BB bioassay in Example 8 for bispecific epitope binding proteins S01-S11.

The bioassay and luciferase assay were carried out in accordance with the manufacturer's protocol. MDA-MB-231 cells expressing PD-L1 were seeded in 96-well white plate (Costar). After overnight incubation in a 37° C. $CO_2$ incubator, the bispecific epitope binding protein variants and 4-1BB effector cells were added for treatment. The twofold serial dilution of the antibody was performed from 100 ng/ml for 4 points. After the treatment with 4-1BB effector cells, incubation in a 37° C. $CO_2$ incubator was carried out for 6 hours, and the luminescence intensity was measured by using a luminometer (Floroskan Ascent FL, Thermo). The results appear in FIG. 10.

Example 9: 4-1BB/PD-1 Combination Bioassay

Figure 11A:
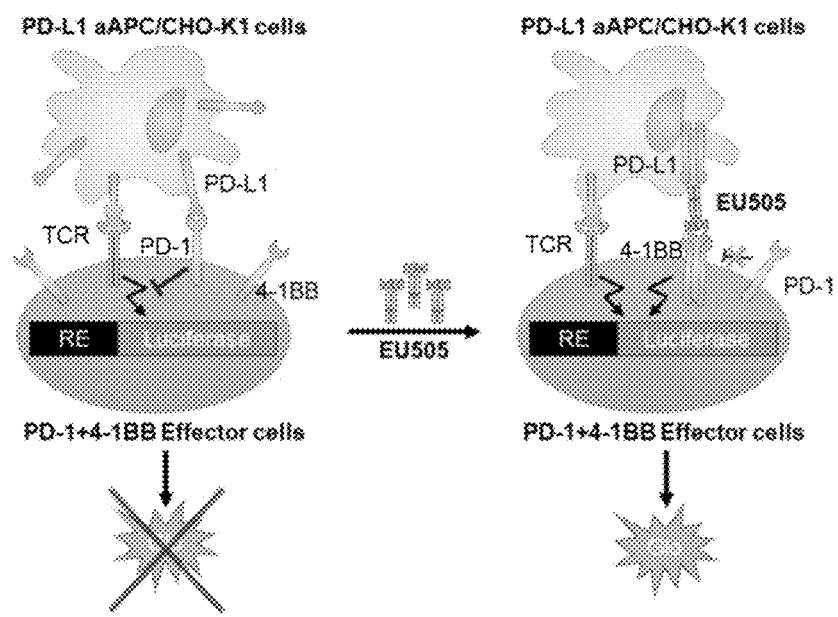
FIG. 11A shows a 4-1BB/PD-1 combination bioassay described in Example 9.

A 4-1BB/PD-1 combination bioassay (Promega, CS1978110) was carried out to verify the effect of inhibiting the binding of PD-1 and PD-L1 and the effect of 4-1BB activity according to the principle that luciferase is expressed when the binding of effector cell to PD-1 and PD-L1 is blocked and the 4-1BB is activated. (FIG. 11A)

The bioassay and luciferase assay were carried out in accordance with the manufacturer's protocol. PD-L1 aAPC/CHO-K1 cells expressing PD-L1 was seeded in a 96-well white plate. It was cultured in 37° C. $CO_2$ incubator overnight and the antibody and effector cells were added for treatment. S03, anti-4-1BB antibody (94kvt-engineered IgG1, SEQ ID NO: 14 and 21), anti-PD-1 antibody (Pembrolizumab, MSD), anti-PD-L1 antibody (Atezolizumab, Roche), and euPD-1 Fc (SEQ ID NO: 22) were used. Three-fold serial dilution from 147 nM was performed for 7 points. 4-1BB effector cells were added for treatment, incubation was carried out in a 37° C. $CO_2$ incubator for 6 hours, and the luminescence intensity was measured by using a luminometer (Floroskan Ascent FL, Thermo).

Figure 11B:
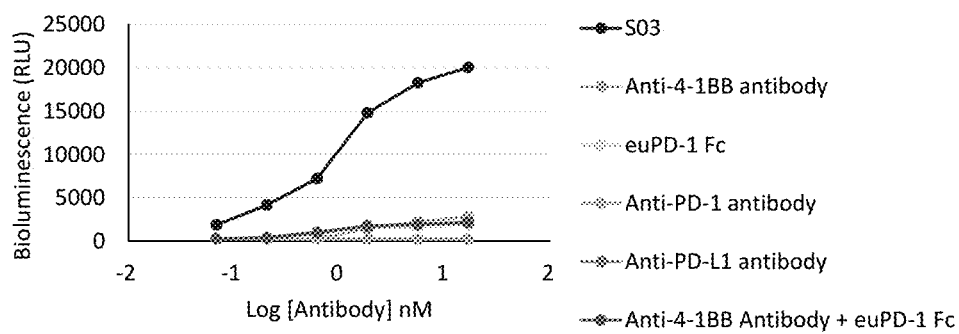
FIG. 11B shows the results of the 4-1BB/PD-1 combination bioassay for bispecific epitope binding protein S03 compared to anti-4-1BB antibody (94kvt-engineered IgG1, SEQ ID NO: 14 and 21), anti-PD-1 antibody (Pembrolizumab, MSD), anti-PD-L1 antibody (Atezolizumab, Roche), and euPD-1 Fc (SEQ ID NO: 22), as well as a specific combination of anti-4-1 BB antibody and euPD-1 Fc.

As a result of the experiment (FIG. 11B), it was identified that the luminescence was strongly detected by S03, which can engage the PD-L1 expression cells and effector cells.

Example 10: Affinity to PD-L1 or PD-L2

PD-1 is known to bind to both PD-L1 and PD-L2. S03 contains euPD-1, an affinity matured form of PD-1. Binding of S03 to PD-L1 and PD-L2 was confirmed by ELISA.

96-well immuno plate was coated with human PD-1-Fc (SinoBiologics, Cat. No. 10377-H02H) of 2 μg/ml, 100 μl per well at 4° C. overnight and added with 150 μl of 1× assay buffer (BioLegend) for 1 hour to block non-specific binding. Three-fold serial dilution of biotinylated PD-L1 (SinoBiologics, Cat. No. 10084-H08H-B) and biotinylated PD-L2 (SinoBiologics, Cat. No. 10292-H08H-B) was carried out from 1 μg/ml for 5 points and 100 μl per well was treated for 1 hour. Thereafter, avidin-HRP (BioLegend, Cat No. 79004) was diluted 1/1000, added thereto 100 ul per well for 30 minutes, color development with TMB was carried out, and the reaction was stopped using sulfuric acid. Washing was performed 3 times using the washing buffer in all processes except for the processes after TMB treatment, and all processes except for the antibody coating process were carried out at room temperature.

Also, four-fold serial dilution of S03, anti-PD-L1 antibody (Roche), and anti-PD-L2 antibody (SinoBiologics, Cat. No. 10292-R018) was performed from 0.1 μg/ml for 4 points, added to 96-well immuno plate 100 μl per well for coating 4° C. overnight. Next, 150 μl of 1× assay buffer was added for treatment for 1 hour to block non-specific binding. 100 μl of biotinylated PD-L1 and biotinylated PD-L2 were added at a concentration of 0.1 μg/ml to each well for treatment for 1 hour. The other procedure after this were the same as human PD-1-Fc ELISA.

Figure 12A:
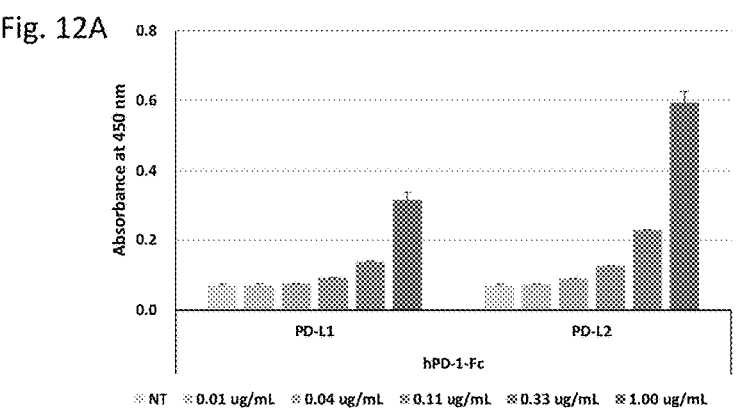
FIG. 12A shows the results of an ELISA assay testing binding of human PD1-Fc to PD-L1 and PD-L2.
Figure 12B:
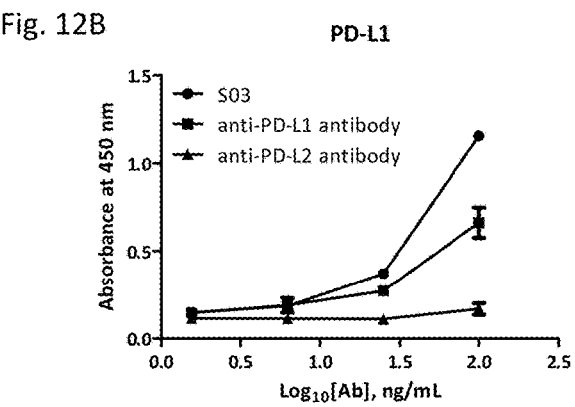
FIG. 12B shows the results of an ELISA assay testing biding of bispecific epitope binding protein S03, anti-PD-L1 antibody, and anti-PD-L2 antibody to PD-L1.
Figure 12C:
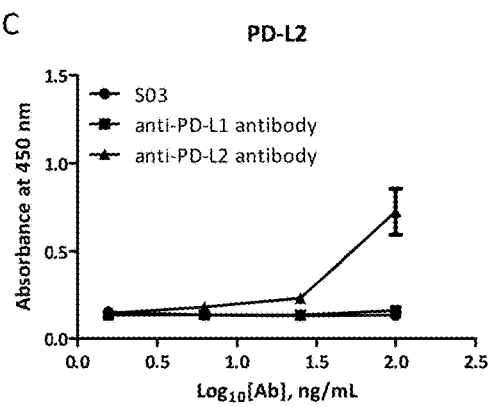
FIG. 12C shows the results of an ELISA assay testing biding of bispecific epitope binding protein S03, anti-PD-L1 antibody, and anti-PD-L2 antibody to PD-L2. (see Example 10)

As a result of the experiment, it was found that human PD-1-Fc binds to both PD-L1 and PD-L2 (FIG. 12A), but the anti-PD-L1 antibody used as a control bind only to PD-L1, and the anti-PD-L2 antibody binds only to PD-L2. The test substance, S03, was only bound to PD-L1. (FIG. 12B-C)

Example 11: Cytotoxicity Assay

A cytotoxicity assay was performed to confirm the T cell medicated cytotoxicity effect on the target cell of S03. T cells isolated by pan T negative selection of human PBMCs (Miltenyi Biotec, Cat. No. 130-096-535) were activated on a plate coated with anti-CD3 antibody (OKT3, Bio X Cell) for 4 days. One day before the T cell and antibody treatment, PD-L1 positive cell line MDA-MB-231-GFP (in-house generated) was seeded $4\times10^4$ cells/well. Three-fold serial dilution of anti-4-1BB antibody (94kvt-engineered IgG1), anti-PD-1 antibody (Pembrolizumab, MSD) and S03 from 1.667 nM was carried out for 4 points for the antibody. The activated T cells were harvested and then treated with tumor cell at 1:1 ratio. GFP signals were measured at 1-hour intervals for 117 hours by using a live-cell analysis system (Incucyte, Sartorius).

Figure 13:
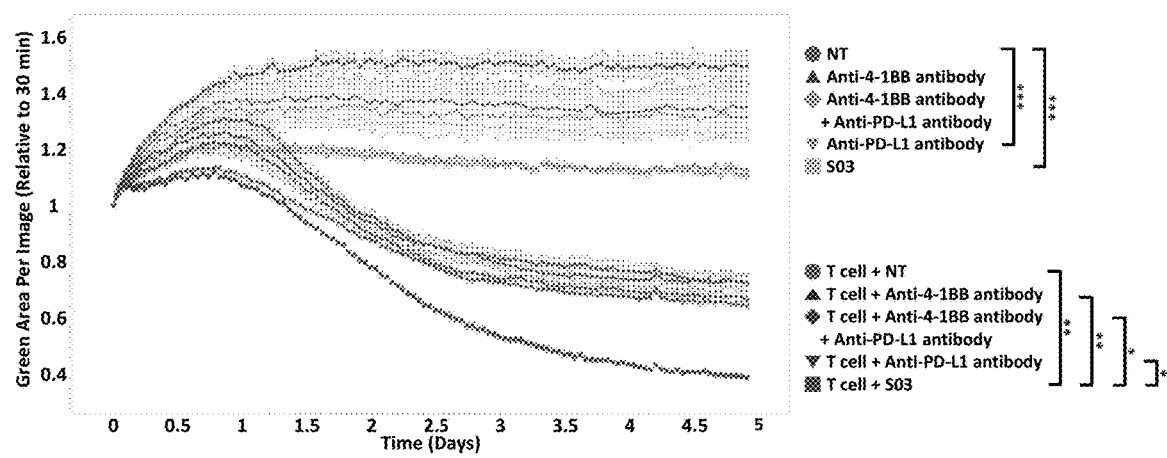
FIG. 13 shows the results of the cytotoxicity assay of Example 11.

The experimental result is data concerning 1.667 nM, and it was confirmed that the T cell-mediated cytotoxicity effect by S03 was superior to the anti-4-1BB antibody and anti-PD-L1 antibody used as controls. (FIG. 13)

Example 12: IFN-γ Assay

The level of IFN-γ produced in T cells was measured by using the supernatant obtained from the cytotoxicity assay (Example 11). The IFN-γ ELISA kit (BioLegend, Cat. No. 430101) was used according to the manufacturer's protocol, and to be brief, 150 μl of 1× assay buffer (BioLegend) was added for 1 hour treatment 1 hour to a plate coated with capture antibody overnight. For the standard, twofold serial dilution was carried out from 500 pg/ml to use 7 points, and supernatant was diluted 50 times and was added by 100 μl to each well for treatment for 2 hours. After treatment with 100 μl of detection antibody for 1 hour, avidin-HRP (BioLegend, Cat No. 79004) was diluted 1/1000 and was added by 100 μl to each well for treatment for 30 minutes. After color development with TMB, the reaction was stopped using sulfuric acid. Washing was performed 3 times using washing buffer in all processes except for the processes after TMB treatment, and all processes except for the antibody coating process were carried out at room temperature.

Figure 14:
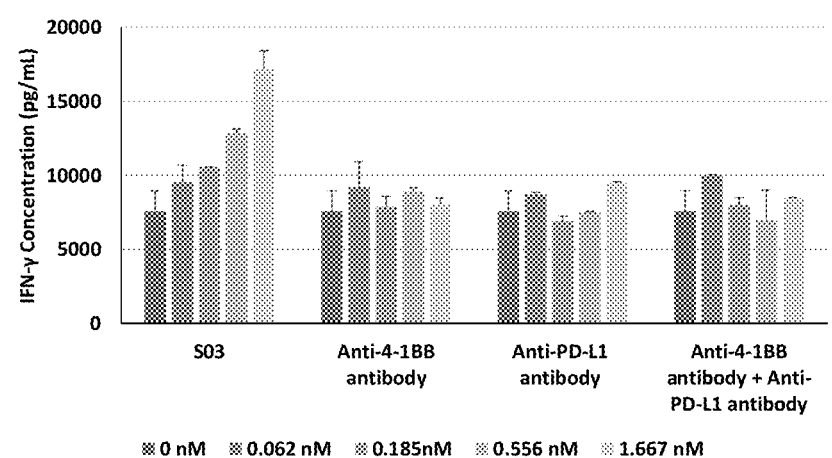
FIG. 14 shows the results of the IFN-γ assay of Example 12.

As a result of the experiment, it can be observed that the IFN-γ production by T cells increases according to the concentration of antibody treatment. (FIG. 14)

Example 13: Antibody-Dependent Cellular Cytotoxicity Assay

IgG1-Fc engineering was utilized for the bispecific epitope binding protein variants to reduce antibody-dependent cellular cytotoxicity (ADCC) and complement-dependent cytotoxicity (CDC). ADCC bioassay (Promega, Cat. No. G701A) was performed using S03 to confirm whether ADCC decreases.

Figure 15A:
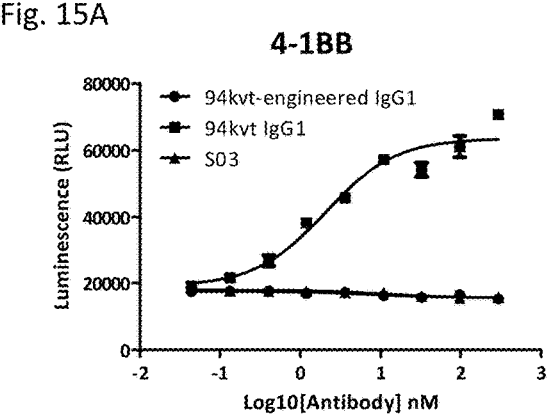
FIG. 15A shows the results of the antibody-dependent cellular cytotoxicity assay of Example 13 with a 4-1BB positive cell line.

A white 96-well plate (Costar) was seeded with 4-1BB positive cell line (4-1BB NF-kB HEK293) and cultured overnight to identify ADCC by anti-4-1BB antibody binding of S03. Next day, three-fold serial dilution of S03 (engineered IgG1, L234A, L235A, K322A, D356E, L358M) and 94kvt-IgG1 (SEQ ID NO: 14 and 20), and 94kvt-engineered IgG1 (L234A, L235A, K322A), which are anti-41BB antibodies, from 294 nM for 8 points. ADCC effector cells were added and incubated for 6 hours in an incubator at 37° C. After that, Bio-Glo luciferase substrate was added and the luminescence intensity was measured using a luminometer (Glo-max, Promega). It can be observed that the 94kvt-IgG1 used as a positive control induces ADCC, while 94kvt-engineered IgG1 and S03, which are negative controls, do not cause ADCC. (FIG. 15A)

Figure 15B:
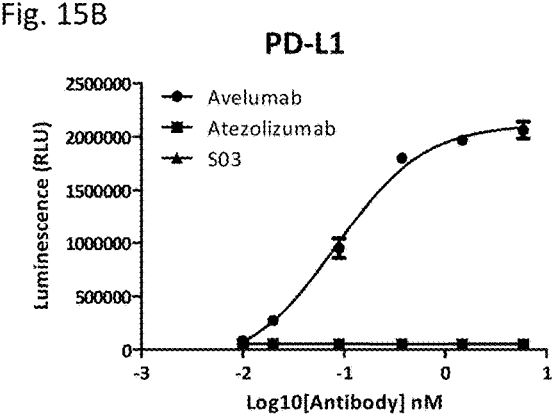
FIG. 15B shows the results of the antibody-dependent cellular cytotoxicity assay of Example 13 with a PD-L1 positive cell line.

To confirm ADCC by euPD-1 of S03, PD-L1 positive cell line (MDA-MB-231) was seeded in a white 96-well plate (Costar) and cultured overnight. The next day, four-fold serial dilution of S03 and Avelumab (Pfizer, IgG1) and Atezolizumab (Roche, Engineered IgG1, N297A), which are anti-PD-L1 antibodies, was carried out from 5.88 nM for 6 points. ADCC effector cells were added and incubated for 6 hours in an incubator at 37° C. After that, Bio-Glo luciferase substrate was added and the luminescence intensity was measured using a luminometer (Glo-max, Promega). Avelumab used as a positive control can be seen to cause ADCC, but it can be observed that Atezolizumab and S03, which are negative controls, do not cause ADCC. (FIG. 15B)

Example 14: Complement-Dependent Cytotoxicity Assay

C1q ELISA was performed to identify that the CDC was reduced by the engineered IgG1 used in S03.

Figure 16:
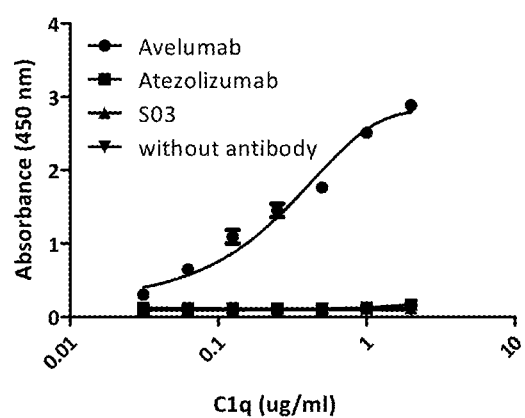
FIG. 16 shows the results of the complement-dependent cytotoxicity assay of Example 14.

96-well immuno plate (NUNC) was coated with 75 nM of S03, Avelumab, and Atezolizumab using 1× coating buffer (BioLegend) at 4° C. overnight, and then 150 µl of 1× assay buffer (BioLegend) was added for 1 hour to block non-specific binding. The biotinylated C1q (comp Tech, Cat. No. A099) protein was processed through twofold serial dilution by using the biotinylation kit (Abcam, Cat. No. Ab201795) from 2 µg/ml for 7 points, 100 µl per well for 2 hours. Next, avidin-HRP (BioLegend, Cat No. 79004) was diluted 1/1000, added to each well by 100 µl for treatment for 1 hour, color development with TMB was carried out, and the reaction was stopped using sulfuric acid. Washing was performed 3 times using washing buffer in all processes except for the processes after TMB treatment, and all processes except for the antibody coating process were carried out at room temperature. It can be observed that Avelumab used as a positive control binds to C1q, but S03 and Atezolizumab, which are negative controls, do not bind to C1q. (FIG. 16)

Example 15: In Vivo Efficacy Study 1—4-1BB KI

To verify the efficacy of S03, an in vivo study was performed using h4-1BB Knock-in mouse (Background: C57BL/6, Biocytogen).

Figure 17A:
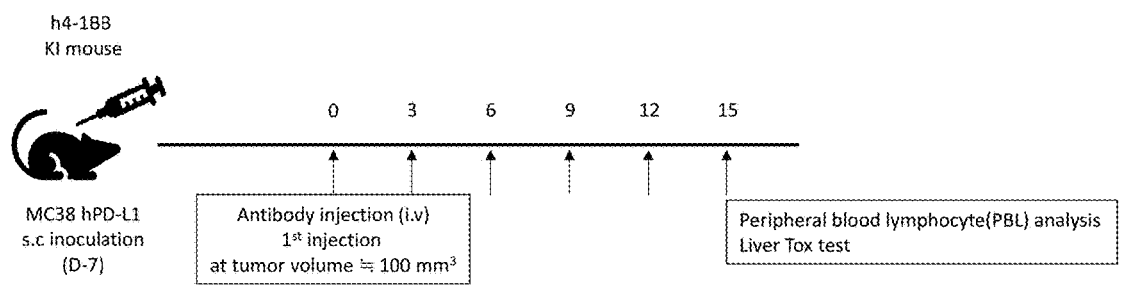
FIG. 17A shows the assay for in vivo efficacy of S03, S05, and S07 using an h4-1BB knock-in mouse as described in Example 15.

MC38 cells expressing PD-L1 were used as the tumor cell as shown in FIG. 17A, and 5×10⁵ tumor cells per individual were administered subcutaneously. One week after administration, the tumor size was measured and the administration groups were divided based on similar mean (within 100 mm³) and standard deviation. Five mice were used for each group.

S03, S05 and S07 were injected intravenously. The excipient DPBS (Gibco) was used as a negative control. The antibody doses were set at 2 mg/kg and 5 mg/kg. The administration was carried out at 100 µl and was administered 5 times at 3-day intervals. The tumor size was also measured at 3-day intervals, and the tumor size was measured until 2 days after the last administration.

Figure 17B:
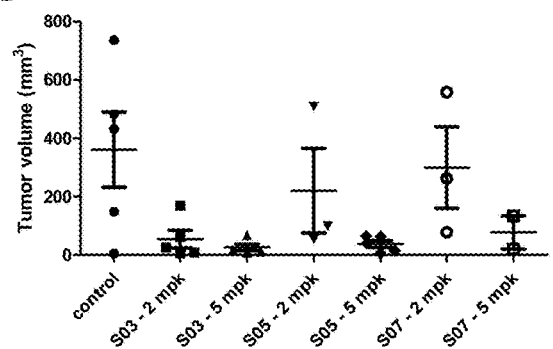
FIG. 17B shows the results of the in vivo efficacy study of S03, S05 and S07 using a h4-1BB knock-in mouse with respect to tumor size.

From the result of tumor size observation, as shown in FIG. 17B, it was confirmed that all of S03, S05 and S07 inhibited tumor growth compared to administration of negative control, and among them, it can be seen that the tumor-reducing effect of S03 was the most outstanding. Further, a dose-dependent response was observed for the tested antibodies.

Example 16: In Vivo Efficacy Study 2—4-1BB KI

To verify the efficacy of S03, an in vivo study was performed using h4-1BB Knock-in mouse (Background: C57BL/6, Biocytogen). The test method is the same as FIG. 17A.

S03, anti-4-1BB antibody (94kvt-engineered IgG1), and anti-PD-L1 antibody (Atezolizumab) were injected intravenously. The excipient DPBS (Gibco) was used as a negative control. The antibody dose was set at 5 mg/kg (5.88 µM) based on S03, and 5.88 µM of anti-4-1BB antibody and anti-PD-L1 antibody were also administered. The administration was carried out at 100 µl and was administered 5 times at 3-day intervals. The tumor size was also measured at 3-day intervals, and the tumor size was measured until 2 days after the last administration. In addition, blood was collected on the day of the end of the experiment and the concentrations of ALT (alanine aminotransferase), AST (aspartate aminotransferase), and BUN (blood urea nitrogen) in the blood were checked using a biochemical analyzer to identify the toxicity.

Figure 18A:
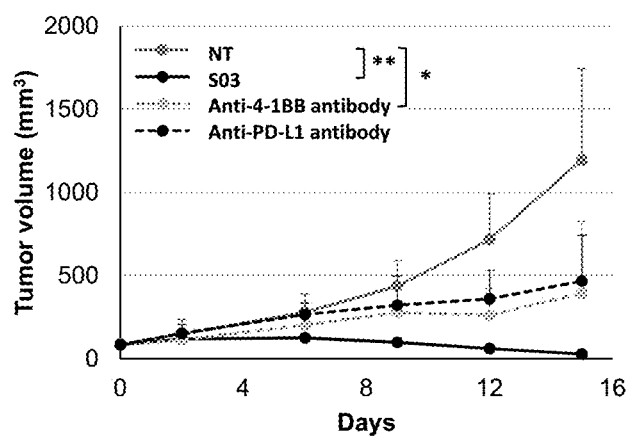
FIG. 18A shows the results of the in vivo efficacy study of S03 using a h4-1BB knock-in mouse with respect to tumor size as described in Example 16.

From the result of tumor size observation, as shown in FIG. 18A, it was confirmed that all of S03, anti-4-1BB antibody, and anti-PD-L1 antibody inhibited tumor growth compared to administration of negative control, and among them, it can be seen that the tumor-reducing effect (approximately 98% reduction) of S03 was the most outstanding.

Figure 18B:
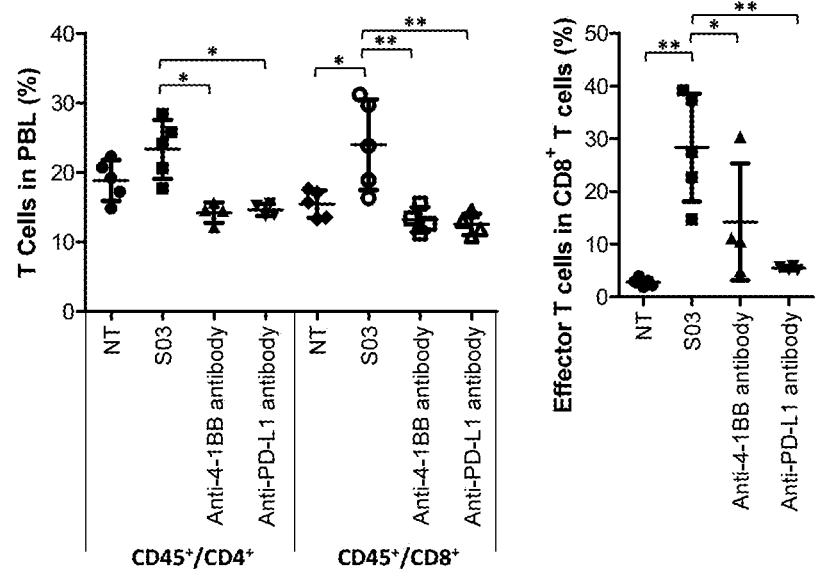
FIG. 18B shows the results of the in vivo efficacy study of S03 using an h4-1BB knock-in mouse with respect to T cell population in the blood.

As shown in FIG. 18B, from the result of analysis of the T cell population in the blood, CD4+ T cell and CD8⁺ T cell in blood were increased by S03, and an increase in effector T cell in CD8+ T cell was observed.

As shown in Table 4, from the result of liver toxicity index analysis, all four indices in the administration group were within the normal range (ALT: 17-77 U/L, AST: 54-298 U/L, BUN: 8-33 mg/dL), and it was confirmed that there was no hepatotoxicity in the liver under the experimental conditions.

TABLE 4

| | Liver hepatotoxicity in serum | | |
|---|---|---|---|
| | ALT (U/L) | AST (U/L) | BUN (mg/dL) |
| Normal range | 17-77 | 54-298 | 8-33 |
| NT | 26.27 ± 1.67 | 97.40 ± 31.32 | 24.61 ± 1.60 |
| S03 | 40.67 ± 8.00 | 59.00 ± 6.63 | 23.21 ± 1.70 |
| Anti-4-1BB antibody | 34.67 ± 6.93 | 69.50 ± 13.40 | 28.72 ± 2.51 |
| Anti-PD-L1 antibody | 28.37 ± 9.24 | 69.50 ± 19.42 | 31.27 ± 8.56 |

Example 17: In Vivo Efficacy Study 3—h4-1BB/hPD-1 DIU

To verify the efficacy of S03, an in vivo study was performed using h4-1BB and hPD-1 double knock-in mouse (Background: C57BL/6, Biocytogen).

MC38 cells expressing PD-L1 were used as the tumor cells as shown in FIG. 17A, and 5×10⁵ tumor cells per individual were subcutaneously administered. One week after administration, the tumor size was measured and the administration groups were divided based on similar mean (around 100 mm³) and standard deviation. Six mice were used in each group.

Antibody S03, anti-4-1BB antibody (94kvt-engineered IgG1), and anti-PD-L1 antibody (Atezolizumab) were injected intravenously. The excipient DPBS (Gibco) was used as a negative control. The antibody dose was set at 5 mg/kg (5.88 µM) based on S03, and 5.88 µM of anti-4-1 BB antibody and anti-PD-L1 antibody were also administered. Administration was carried out at 100 and was administered 5 times at 3-day intervals. The tumor size was also measured at 3-day intervals, and the tumor size was measured until 2 days after the last administration.

Figure 19:
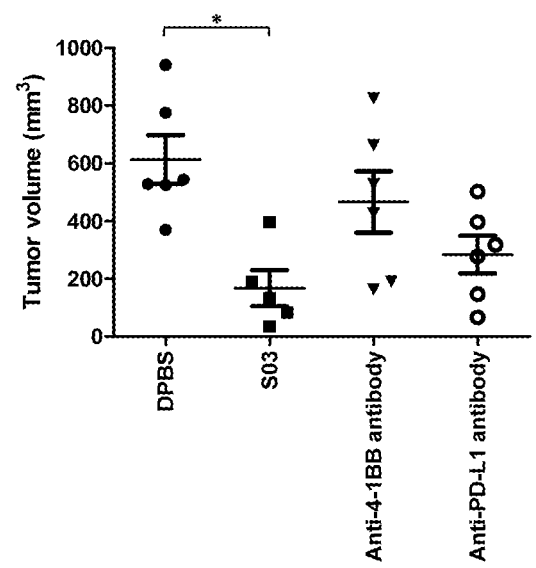
FIG. 19 shows the results of the in vivo efficacy study of S03 using h4-1BB and hPD-1 double knock-in mouse with respect to tumor size as described in Example 17.

As a result of observation of the tumor size, as shown in FIG. 19, it was confirmed that tumor growth was inhibited for all of S03, anti-4-1BB antibody, and anti-PD-L1 antibody compared to administration of the negative control (approximately 73% reduction).

All data are graphed as mean SEM, one-way ANOVA statistical test. All statistics were calculated using per-animal or per-sample average data. $*p<0.05$, $p<0.01$, $*p<0.001$.

The specific part of the content of the present invention has been described as above. For those of ordinary skill in the art, such specific description is only a preferred embodiment, and it will be clear that the scope of the present invention is not limited thereto. Accordingly, it is intended that the substantial scope of the present invention be defined by the appended claims and their equivalents.

---

What we claim is:

1. A bispecific epitope binding protein which comprises (VH-VL) or (VL-VH): and (X) n at the N-terminus or C-terminus: wherein the (X) n linked to VH or VL by Y,
   wherein VH and VL refer to a variable heavy region and a variable light region, respectively, of antibodies or antigen-binding fragments thereof that bind to 4-1BB,
   wherein the VH comprises the sequence of SEQ ID NO: 23,
   wherein the VL comprises the sequence of SEQ ID NO: 25,
   wherein X is a PD-1 protein or fragment thereof that binds to PD-L1,
   wherein the PD-1 protein comprises the sequence of SEQ ID NO: 27,
   wherein Y refers to a fragment of the heavy chain constant region or the light chain constant region comprising one or more domain selected from the group consisting of CL, CH1, CH2, and CH3, and
   wherein n is an integer of 1 to 5.

2. The bispecific epitope binding protein of claim 1, wherein the VH, VL, Y, and (X) n are linked sequentially from the N-terminus to the C-terminus.

3. The bispecific epitope binding protein of claim 1, wherein said bispecific epitope binding protein has bispecific binding affinity for 4-1BB and PD-L1.

4. The bispecific epitope binding protein of claim 1, further comprising a signal peptide connected to the N-terminus or C-terminus.

5. The bispecific epitope binding protein of claim 4, wherein said signal peptide is an N-terminal signal peptide comprising 12 to 40 amino acids.

6. A nucleic acid molecule encoding the bispecific epitope binding protein of claim 1.

7. A recombinant vector comprising the nucleic acid molecule of claim 6.

8. A cell comprising the recombinant vector of claim 7.

9. A method of producing a bispecific epitope binding protein, the method comprising: culturing the cell of claim 8 in a culture medium under conditions sufficient to result in the production of the bispecific epitope binding protein; and recovering the bispecific epitope binding protein from the cell and/or the culture medium.

10. A method of treating cancer in a subject in need thereof, the method comprising:
    administering to the subject a composition that comprises or delivers an effective amount of the bispecific epitope binding protein of claim 1.

11. The method of claim 10, wherein the cancer comprises a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, prostate cancer, and combinations thereof.

12. The bispecific epitope binding protein of claim 1, wherein the VL, VH, Y, and (X) n are linked sequentially from the N-terminus to the C-terminus.

13. The bispecific epitope binding protein of claim 1, wherein the (X) n, Y, VH, and VL are linked sequentially from the N-terminus to the C-terminus.

14. The bispecific epitope binding protein of claim 1, wherein the (X) n, Y, VL, and VH are linked sequentially from the N-terminus to the C-terminus.

15. The bispecific epitope binding protein of claim 1, wherein the VH and VL connected directly or by a linker and/or a hinge, and the (X) n connected by a hinge and/or a linker.

16. The bispecific epitope binding protein of claim 1, wherein the CH1 domain is C-terminally linked to (VH-VL), (VL-VH), or (X) n directly or by a hinge and/or a linker and the CH2/CH3 domain(s) is N-terminally linked to (VH-VL), (VL-VH), (X) n directly or by a hinge and/or a linker.

17. The bispecific epitope binding protein of claim 1, wherein Y is independently a CH2 or CH3 domain, the VH, VL, CH2 and/or CH3; or VH, CH2 and/or CH3 and X; are connected directly or through a hinge and/or a linker.

18. A bispecific epitope binding protein which comprises a heavy chain comprising VH and (X) n, wherein (X) n connected to VH by Y; and a light chain of the sequence of SEQ ID NO: 14;
    wherein the VH refer to a variable heavy region of antibodies or antigen-binding fragments thereof that bind to 4-1BB,
    wherein the VH consist of SEQ ID NO: 23,
    wherein X is a PD-1 protein or fragment thereof that binds to PD-L1,
    wherein the PD-1 protein comprises the sequence of SEQ ID NO: 27,
    wherein Y refers to a fragment of the heavy chain constant region or the light chain constant region comprising one or more domain selected from the group consisting of CL, CH1, CH2, and CH3,
    wherein the bispecific epitope binding protein comprises the 4-1BB-binding antibody or antigen-binding fragment; and a PD-1 protein or fragment; and
    wherein n is an integer of 1 to 5.

19. The bispecific epitope binding protein of claim 18, wherein the bispecific epitope binding protein has bispecific binding affinity for 4-1BB and PD-L1.

20. The bispecific epitope binding protein of claim 18, further comprising a signal peptide connected to the N-terminus or C-terminus.

21. The bispecific epitope binding protein of claim 20, wherein said signal peptide is an N-terminal signal peptide comprising 12 to 40 amino acids.

22. A nucleic acid molecule encoding the bispecific epitope binding protein of claim 18.

23. A recombinant vector comprising the nucleic acid molecule of claim 22.

24. A cell comprising the recombinant vector of claim 23.

25. A method of producing a bispecific epitope binding protein, the method comprising: culturing the cell of claim 24 in a culture medium under conditions sufficient to result in the production of the bispecific epitope binding protein; and recovering the bispecific epitope binding protein from the cell and/or the culture medium.

26. A method of treating cancer in a subject in need thereof, the method comprising:
 administering to the subject a composition that comprises or delivers an effective amount of the bispecific epitope binding protein of claim 18.

27. The method of claim 26, wherein the cancer comprises a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, prostate cancer, and combinations thereof.

* * * * *

SEQUENCE LISTING

```
<160> NUMBER OF SEQ ID NOS: 39

<210> SEQ ID NO 1
<211> LENGTH: 641
<212> TYPE: PRT
<213> ORGANISM: Artificial Sequence
<220> FEATURE:
<223> OTHER INFORMATION: Bispecific epitope  binding protein S01

<400> SEQUENCE: 1

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
    50                  55                  60

Lys Ser Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Lys Thr Ala Arg Ala Phe Ala Tyr Trp Gly Gln Gly
            100                 105                 110

Thr Leu Val Thr Val Ser Ser Gly Ser Thr Ser Gly Ser Gly Lys Pro
        115                 120                 125

Gly Ser Gly Glu Gly Ser Thr Lys Gly Asp Ile Val Met Thr Gln Ser
    130                 135                 140

Pro Ala Phe Leu Ser Val Thr Pro Gly Glu Lys Val Thr Ile Thr Cys
145                 150                 155                 160

Arg Ala Ser Gln Thr Ile Ser Asp Tyr Leu His Trp Tyr Gln Gln Lys
                165                 170                 175

Pro Asp Gln Ala Pro Lys Leu Leu Ile Lys Tyr Ala Ser Gln Ser Ile
            180                 185                 190

Ser Gly Ile Pro Ser Arg Phe Ser Gly Ser Gly Ser Gly Thr Asp Phe
        195                 200                 205

Thr Phe Thr Ile Ser Ser Leu Glu Ala Glu Asp Ala Ala Thr Tyr Tyr
    210                 215                 220

Cys Gln Asp Gly His Ser Trp Pro Pro Thr Phe Gly Gln Gly Thr Lys
225                 230                 235                 240
```

```
Leu Glu Ile Lys Ala Ser Gly Gly Gly Ser Gly Gly Gly Ser
                    245                 250             255

Asp Lys Thr His Thr Cys Pro Pro Cys Pro Ala Pro Glu Ala Ala Gly
            260                 265                 270

Gly Pro Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
            290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Ala Val Ser Asn Lys Ala Leu Pro Ala Pro Ile
            355                 360                 365

Glu Lys Thr Ile Ser Lys Ala Lys Gly Gln Pro Arg Glu Pro Gln Val
            370                 375                 380

Tyr Thr Leu Pro Pro Ser Arg Glu Glu Met Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Gly Gly Gly Ser Gly Gly Gly Ser Phe Leu Glu Ser
                485                 490                 495

Pro Asp Arg Pro Trp Asn Ala Pro Thr Phe Ser Pro Ala Leu Leu Leu
            500                 505                 510

Val Ala Glu Gly Asp Asn Ala Thr Phe Thr Cys Ser Phe Ser Asn Ala
            515                 520                 525

Ser Glu Ser Phe His Val Val Trp His Arg Glu Ser Pro Ser Gly Gln
            530                 535                 540

Thr Asp Thr Leu Ala Ala Phe Pro Glu Asp Arg Ser Gln Pro Gly Gln
545                 550                 555                 560

Asp His Arg Phe Arg Val Thr Arg Leu Pro Asn Gly Arg Asp Phe His
                565                 570                 575

Met Ser Val Val Arg Ala Gln Arg Asn Asp Ser Gly Thr Tyr Val Cys
                580                 585                 590

Gly Val Ile Ser Leu Ala Pro Lys Ile Gln Ile Lys Glu Ser Leu Arg
            595                 600                 605

Ala Glu Leu Arg Val Thr Glu Arg Arg Ala Glu Val Pro Thr Ala His
            610                 615                 620

Pro Ser Pro Ser Pro Arg Pro Ala Gly Gln Phe Gln Thr Leu Val Val
625                 630                 635                 640

Gly

<210> SEQ ID NO 2
```

<211> LENGTH: 805
<212> TYPE: PRT
<213> ORGANISM: Artificial Sequence
<220> FEATURE:
<223> OTHER INFORMATION: Bispecific epitope binding protein S02

<400> SEQUENCE: 2

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
    50                  55                  60

Lys Ser Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Lys Thr Ala Arg Ala Phe Ala Tyr Trp Gly Gln Gly
            100                 105                 110

Thr Leu Val Thr Val Ser Ser Gly Ser Thr Ser Gly Ser Gly Lys Pro
        115                 120                 125

Gly Ser Gly Glu Gly Ser Thr Lys Gly Asp Ile Val Met Thr Gln Ser
    130                 135                 140

Pro Ala Phe Leu Ser Val Thr Pro Gly Glu Lys Val Thr Ile Thr Cys
145                 150                 155                 160

Arg Ala Ser Gln Thr Ile Ser Asp Tyr Leu His Trp Tyr Gln Gln Lys
                165                 170                 175

Pro Asp Gln Ala Pro Lys Leu Leu Ile Lys Tyr Ala Ser Gln Ser Ile
            180                 185                 190

Ser Gly Ile Pro Ser Arg Phe Ser Gly Ser Gly Ser Gly Thr Asp Phe
        195                 200                 205

Thr Phe Thr Ile Ser Ser Leu Glu Ala Glu Asp Ala Ala Thr Tyr Tyr
    210                 215                 220

Cys Gln Asp Gly His Ser Trp Pro Pro Thr Phe Gly Gln Gly Thr Lys
225                 230                 235                 240

Leu Glu Ile Lys Ala Ser Gly Gly Gly Ser Gly Gly Gly Gly Gly Ser
                245                 250                 255

Asp Lys Thr His Thr Cys Pro Pro Cys Pro Ala Pro Glu Ala Ala Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Ala Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

```
Tyr Thr Leu Pro Pro Ser Arg Glu Glu Met Thr Lys Asn Gln Val Ser
385                 390                 395                 400

Leu Thr Cys Leu Val Lys Gly Phe Tyr Pro Ser Asp Ile Ala Val Glu
            405                 410                 415

Trp Glu Ser Asn Gly Gln Pro Glu Asn Asn Tyr Lys Thr Thr Pro Pro
        420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Gly Gly Gly Ser Gly Gly Gly Gly Ser Phe Leu Glu Ser
                485                 490                 495

Pro Asp Arg Pro Trp Asn Ala Pro Thr Phe Ser Pro Ala Leu Leu Leu
            500                 505                 510

Val Ala Glu Gly Asp Asn Ala Thr Phe Thr Cys Ser Phe Ser Asn Ala
        515                 520                 525

Ser Glu Ser Phe His Val Val Trp His Arg Glu Ser Pro Ser Gly Gln
530                 535                 540

Thr Asp Thr Leu Ala Ala Phe Pro Glu Asp Arg Ser Gln Pro Gly Gln
545                 550                 555                 560

Asp His Arg Phe Arg Val Thr Arg Leu Pro Asn Gly Arg Asp Phe His
            565                 570                 575

Met Ser Val Val Arg Ala Gln Arg Asn Asp Ser Gly Thr Tyr Val Cys
        580                 585                 590

Gly Val Ile Ser Leu Ala Pro Lys Ile Gln Ile Lys Glu Ser Leu Arg
        595                 600                 605

Ala Glu Leu Arg Val Thr Glu Arg Arg Ala Glu Val Pro Thr Ala His
    610                 615                 620

Pro Ser Pro Ser Pro Arg Pro Ala Gly Gln Phe Gln Thr Leu Val Val
625                 630                 635                 640

Gly Gly Gly Gly Ser Gly Gly Gly Gly Ser Gly Gly Gly Gly Ser
                645                 650                 655

Phe Leu Glu Ser Pro Asp Arg Pro Trp Asn Ala Pro Thr Phe Ser Pro
            660                 665                 670

Ala Leu Leu Leu Val Ala Glu Gly Asp Asn Ala Thr Phe Thr Cys Ser
        675                 680                 685

Phe Ser Asn Ala Ser Glu Ser Phe His Val Val Trp His Arg Glu Ser
        690                 695                 700

Pro Ser Gly Gln Thr Asp Thr Leu Ala Ala Phe Pro Glu Asp Arg Ser
705                 710                 715                 720

Gln Pro Gly Gln Asp His Arg Phe Arg Val Thr Arg Leu Pro Asn Gly
                725                 730                 735

Arg Asp Phe His Met Ser Val Val Arg Ala Gln Arg Asn Asp Ser Gly
            740                 745                 750

Thr Tyr Val Cys Gly Val Ile Ser Leu Ala Pro Lys Ile Gln Ile Lys
        755                 760                 765

Glu Ser Leu Arg Ala Glu Leu Arg Val Thr Glu Arg Arg Ala Glu Val
    770                 775                 780

Pro Thr Ala His Pro Ser Pro Ser Pro Arg Pro Ala Gly Gln Phe Gln
785                 790                 795                 800
```

```
Thr Leu Val Val Gly
            805

<210> SEQ ID NO 3
<211> LENGTH: 641
<212> TYPE: PRT
<213> ORGANISM: Artificial Sequence
<220> FEATURE:
<223> OTHER INFORMATION: Bispecific epitope binding protein S03

<400> SEQUENCE: 3

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30

Leu His Trp Tyr Gln Gln Lys Pro Asp Gln Ala Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Trp Pro Pro
                85                  90                  95

Thr Phe Gly Gln Gly Thr Lys Leu Glu Ile Lys Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Ala Glu Val Lys Lys Pro Gly Ala Ser Val Lys
    130                 135                 140

Leu Ser Cys Lys Ala Ser Gly Tyr Thr Phe Ser Ser Tyr Trp Met His
145                 150                 155                 160

Trp Val Arg Gln Ala Pro Gly Gln Gly Leu Glu Trp Ile Gly Glu Ile
                165                 170                 175

Asn Pro Gly Asn Gly His Thr Asn Tyr Asn Glu Lys Phe Lys Ser Arg
            180                 185                 190

Val Thr Met Thr Arg Asp Thr Ser Thr Ala Tyr Met Glu Leu
        195                 200                 205

Ser Ser Leu Arg Ser Glu Asp Thr Ala Val Tyr Tyr Cys Ala Arg Ser
210                 215                 220

Phe Lys Thr Ala Arg Ala Phe Ala Tyr Trp Gly Gln Gly Thr Leu Val
225                 230                 235                 240

Thr Val Ser Ser Ala Ser Gly Gly Gly Gly Ser Gly Gly Gly Gly Ser
                245                 250                 255

Asp Lys Thr His Thr Cys Pro Pro Cys Pro Ala Pro Glu Ala Ala Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350
```

```
Lys Glu Tyr Lys Cys Ala Val Ser Asn Lys Ala Leu Pro Ala Pro Ile
            355                 360                 365
Glu Lys Thr Ile Ser Lys Ala Lys Gly Gln Pro Arg Glu Pro Gln Val
        370                 375                 380
Tyr Thr Leu Pro Pro Ser Arg Glu Glu Met Thr Lys Asn Gln Val Ser
385                 390                 395                 400
Leu Thr Cys Leu Val Lys Gly Phe Tyr Pro Ser Asp Ile Ala Val Glu
                405                 410                 415
Trp Glu Ser Asn Gly Gln Pro Glu Asn Asn Tyr Lys Thr Thr Pro Pro
            420                 425                 430
Val Leu Asp Ser Asp Gly Ser Phe Phe Leu Tyr Ser Lys Leu Thr Val
        435                 440                 445
Asp Lys Ser Arg Trp Gln Gln Gly Asn Val Phe Ser Cys Ser Val Met
450                 455                 460
His Glu Ala Leu His Asn His Tyr Thr Gln Lys Ser Leu Ser Leu Ser
465                 470                 475                 480
Pro Gly Gly Gly Gly Ser Gly Gly Gly Gly Ser Phe Leu Glu Ser
                485                 490                 495
Pro Asp Arg Pro Trp Asn Ala Pro Thr Phe Ser Pro Ala Leu Leu Leu
            500                 505                 510
Val Ala Glu Gly Asp Asn Ala Thr Phe Thr Cys Ser Phe Ser Asn Ala
        515                 520                 525
Ser Glu Ser Phe His Val Val Trp His Arg Glu Ser Pro Ser Gly Gln
530                 535                 540
Thr Asp Thr Leu Ala Ala Phe Pro Glu Asp Arg Ser Gln Pro Gly Gln
545                 550                 555                 560
Asp His Arg Phe Arg Val Thr Arg Leu Pro Asn Gly Arg Asp Phe His
                565                 570                 575
Met Ser Val Val Arg Ala Gln Arg Asn Asp Ser Gly Thr Tyr Val Cys
            580                 585                 590
Gly Val Ile Ser Leu Ala Pro Lys Ile Gln Ile Lys Glu Ser Leu Arg
        595                 600                 605
Ala Glu Leu Arg Val Thr Glu Arg Arg Ala Glu Val Pro Thr Ala His
610                 615                 620
Pro Ser Pro Ser Pro Arg Pro Ala Gly Gln Phe Gln Thr Leu Val Val
625                 630                 635                 640
Gly
```

```
<210> SEQ ID NO 4
<211> LENGTH: 805
<212> TYPE: PRT
<213> ORGANISM: Artificial Sequence
<220> FEATURE:
<223> OTHER INFORMATION: Bispecific epitope binding protein S04

<400> SEQUENCE: 4
```

```
Asp Ile Val Met Thr Gln Ser Pro Ala Phe Leu Ser Val Thr Pro Gly
1               5                   10                  15
Glu Lys Val Thr Ile Thr Cys Arg Ala Ser Gln Thr Ile Ser Asp Tyr
            20                  25                  30
Leu His Trp Tyr Gln Gln Lys Pro Asp Gln Ala Pro Lys Leu Leu Ile
        35                  40                  45
Lys Tyr Ala Ser Gln Ser Ile Ser Gly Ile Pro Ser Arg Phe Ser Gly
    50                  55                  60
Ser Gly Ser Gly Thr Asp Phe Thr Phe Thr Ile Ser Ser Leu Glu Ala
```

```
                65                  70                  75                  80
Glu Asp Ala Ala Thr Tyr Tyr Cys Gln Asp Gly His Ser Trp Pro Pro
                        85                  90                  95

Thr Phe Gly Gln Gly Thr Lys Leu Glu Ile Lys Gly Ser Thr Ser Gly
                100                 105                 110

Ser Gly Lys Pro Gly Ser Gly Glu Gly Ser Thr Lys Gly Gln Val Gln
                115                 120                 125

Leu Val Gln Ser Gly Ala Glu Val Lys Lys Pro Gly Ala Ser Val Lys
            130                 135                 140

Leu Ser Cys Lys Ala Ser Gly Tyr Thr Phe Ser Ser Tyr Trp Met His
145                 150                 155                 160

Trp Val Arg Gln Ala Pro Gly Gln Gly Leu Glu Trp Ile Gly Glu Ile
                165                 170                 175

Asn Pro Gly Asn Gly His Thr Asn Tyr Asn Glu Lys Phe Lys Ser Arg
                180                 185                 190

Val Thr Met Thr Arg Asp Thr Ser Thr Ser Thr Ala Tyr Met Glu Leu
            195                 200                 205

Ser Ser Leu Arg Ser Glu Asp Thr Ala Val Tyr Tyr Cys Ala Arg Ser
        210                 215                 220

Phe Lys Thr Ala Arg Ala Phe Ala Tyr Trp Gly Gln Gly Thr Leu Val
225                 230                 235                 240

Thr Val Ser Ser Ala Ser Gly Gly Gly Ser Gly Gly Gly Gly Ser
                245                 250                 255

Asp Lys Thr His Thr Cys Pro Pro Cys Pro Ala Pro Glu Ala Ala Gly
                260                 265                 270

Gly Pro Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
        290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
                340                 345                 350

Lys Glu Tyr Lys Cys Ala Val Ser Asn Lys Ala Leu Pro Ala Pro Ile
            355                 360                 365

Glu Lys Thr Ile Ser Lys Ala Lys Gly Gln Pro Arg Glu Pro Gln Val
        370                 375                 380

Tyr Thr Leu Pro Pro Ser Arg Glu Glu Met Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
        450                 455                 460

His Glu Ala Leu His Asn His Tyr Thr Gln Lys Ser Leu Ser Leu Ser
465                 470                 475                 480

Pro Gly Gly Gly Gly Ser Gly Gly Gly Gly Ser Phe Leu Glu Ser
                485                 490                 495
```

Pro Asp Arg Pro Trp Asn Ala Pro Thr Phe Ser Pro Ala Leu Leu Leu
            500                 505                 510

Val Ala Glu Gly Asp Asn Ala Thr Phe Thr Cys Ser Phe Ser Asn Ala
            515                 520                 525

Ser Glu Ser Phe His Val Val Trp His Arg Glu Ser Pro Ser Gly Gln
            530                 535                 540

Thr Asp Thr Leu Ala Ala Phe Pro Glu Asp Arg Ser Gln Pro Gly Gln
545                 550                 555                 560

Asp His Arg Phe Arg Val Thr Arg Leu Pro Asn Gly Arg Asp Phe His
                565                 570                 575

Met Ser Val Val Arg Ala Gln Arg Asn Asp Ser Gly Thr Tyr Val Cys
            580                 585                 590

Gly Val Ile Ser Leu Ala Pro Lys Ile Gln Ile Lys Glu Ser Leu Arg
            595                 600                 605

Ala Glu Leu Arg Val Thr Glu Arg Arg Ala Glu Val Pro Thr Ala His
            610                 615                 620

Pro Ser Pro Ser Pro Arg Pro Ala Gly Gln Phe Gln Thr Leu Val Val
625                 630                 635                 640

Gly Gly Gly Gly Ser Gly Gly Gly Ser Gly Gly Gly Gly Ser
                645                 650                 655

Phe Leu Glu Ser Pro Asp Arg Pro Trp Asn Ala Pro Thr Phe Ser Pro
                660                 665                 670

Ala Leu Leu Leu Val Ala Glu Gly Asp Asn Ala Thr Phe Thr Cys Ser
            675                 680                 685

Phe Ser Asn Ala Ser Glu Ser Phe His Val Val Trp His Arg Glu Ser
            690                 695                 700

Pro Ser Gly Gln Thr Asp Thr Leu Ala Ala Phe Pro Glu Asp Arg Ser
705                 710                 715                 720

Gln Pro Gly Gln Asp His Arg Phe Arg Val Thr Arg Leu Pro Asn Gly
                725                 730                 735

Arg Asp Phe His Met Ser Val Val Arg Ala Gln Arg Asn Asp Ser Gly
                740                 745                 750

Thr Tyr Val Cys Gly Val Ile Ser Leu Ala Pro Lys Ile Gln Ile Lys
            755                 760                 765

Glu Ser Leu Arg Ala Glu Leu Arg Val Thr Glu Arg Arg Ala Glu Val
            770                 775                 780

Pro Thr Ala His Pro Ser Pro Ser Pro Arg Pro Ala Gly Gln Phe Gln
785                 790                 795                 800

Thr Leu Val Val Gly
                805

<210> SEQ ID NO 5
<211> LENGTH: 641
<212> TYPE: PRT
<213> ORGANISM: Artificial Sequence
<220> FEATURE:
<223> OTHER INFORMATION: Bispecific epitope binding protein S05

<400> SEQUENCE: 5

Phe Leu Glu Ser Pro Asp Arg Pro Trp Asn Ala Pro Thr Phe Ser Pro
1               5                   10                  15

Ala Leu Leu Leu Val Ala Glu Gly Asp Asn Ala Thr Phe Thr Cys Ser
            20                  25                  30

Phe Ser Asn Ala Ser Glu Ser Phe His Val Val Trp His Arg Glu Ser
        35                  40                  45

```
Pro Ser Gly Gln Thr Asp Thr Leu Ala Ala Phe Pro Glu Asp Arg Ser
 50                  55                  60

Gln Pro Gly Gln Asp His Arg Phe Arg Val Thr Arg Leu Pro Asn Gly
 65                  70                  75                  80

Arg Asp Phe His Met Ser Val Val Arg Ala Gln Arg Asn Asp Ser Gly
                 85                  90                  95

Thr Tyr Val Cys Gly Val Ile Ser Leu Ala Pro Lys Ile Gln Ile Lys
                100                 105                 110

Glu Ser Leu Arg Ala Glu Leu Arg Val Thr Glu Arg Arg Ala Glu Val
            115                 120                 125

Pro Thr Ala His Pro Ser Pro Ser Pro Arg Pro Ala Gly Gln Phe Gln
            130                 135                 140

Thr Leu Val Val Gly Ala Ser Gly Gly Gly Ser Gly Gly Gly Gly
145                 150                 155                 160

Ser Asp Lys Thr His Thr Cys Pro Pro Cys Pro Ala Pro Glu Ala Ala
                165                 170                 175

Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
            195                 200                 205

His Glu Asp Pro Glu Val Lys Phe Asn Trp Tyr Val Asp Gly Val Glu
210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Ala Val Ser Asn Lys Ala Leu Pro Ala Pro
            260                 265                 270

Ile Glu Lys Thr Ile Ser Lys Ala Lys Gly Gln Pro Arg Glu Pro Gln
            275                 280                 285

Val Tyr Thr Leu Pro Pro Ser Arg Glu Glu Met Thr Lys Asn Gln Val
            290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
                340                 345                 350

Val Asp Lys Ser Arg Trp Gln Gln Gly Asn Val Phe Ser Cys Ser Val
            355                 360                 365

Met His Glu Ala Leu His Asn His Tyr Thr Gln Lys Ser Leu Ser Leu
            370                 375                 380

Ser Pro Gly Gly Gly Gly Ser Gly Gly Gly Gly Ser Gln Val Gln
385                 390                 395                 400

Leu Val Gln Ser Gly Ala Glu Val Lys Lys Pro Gly Ala Ser Val Lys
                405                 410                 415

Leu Ser Cys Lys Ala Ser Gly Tyr Thr Phe Ser Ser Tyr Trp Met His
            420                 425                 430

Trp Val Arg Gln Ala Pro Gly Gln Gly Leu Glu Trp Ile Gly Glu Ile
            435                 440                 445

Asn Pro Gly Asn Gly His Thr Asn Tyr Asn Glu Lys Phe Lys Ser Arg
450                 455                 460
```

```
Val Thr Met Thr Arg Asp Thr Ser Thr Ser Thr Ala Tyr Met Glu Leu
465                 470                 475                 480

Ser Ser Leu Arg Ser Glu Asp Thr Ala Val Tyr Tyr Cys Ala Arg Ser
            485                 490                 495

Phe Lys Thr Ala Arg Ala Phe Ala Tyr Trp Gly Gln Gly Thr Leu Val
        500                 505                 510

Thr Val Ser Ser Gly Ser Thr Ser Gly Ser Gly Lys Pro Gly Ser Gly
    515                 520                 525

Glu Gly Ser Thr Lys Gly Asp Ile Val Met Thr Gln Ser Pro Ala Phe
    530                 535                 540

Leu Ser Val Thr Pro Gly Glu Lys Val Thr Ile Thr Cys Arg Ala Ser
545                 550                 555                 560

Gln Thr Ile Ser Asp Tyr Leu His Trp Tyr Gln Gln Lys Pro Asp Gln
            565                 570                 575

Ala Pro Lys Leu Leu Ile Lys Tyr Ala Ser Gln Ser Ile Ser Gly Ile
        580                 585                 590

Pro Ser Arg Phe Ser Gly Ser Gly Ser Gly Thr Asp Phe Thr Phe Thr
    595                 600                 605

Ile Ser Ser Leu Glu Ala Glu Asp Ala Ala Thr Tyr Tyr Cys Gln Asp
610                 615                 620

Gly His Ser Trp Pro Pro Thr Phe Gly Gln Gly Thr Lys Leu Glu Ile
625                 630                 635                 640

Lys
```

<210> SEQ ID NO 6
<211> LENGTH: 805
<212> TYPE: PRT
<213> ORGANISM: Artificial Sequence
<220> FEATURE:
<223> OTHER INFORMATION: Bispecific epitope binding protein S06

<400> SEQUENCE: 6

```
Phe Leu Glu Ser Pro Asp Arg Pro Trp Asn Ala Pro Thr Phe Ser Pro
1               5                   10                  15

Ala Leu Leu Leu Val Ala Glu Gly Asp Asn Ala Thr Phe Thr Cys Ser
            20                  25                  30

Phe Ser Asn Ala Ser Glu Ser Phe His Val Val Trp His Arg Glu Ser
        35                  40                  45

Pro Ser Gly Gln Thr Asp Thr Leu Ala Ala Phe Pro Glu Asp Arg Ser
    50                  55                  60

Gln Pro Gly Gln Asp His Arg Phe Arg Val Thr Arg Leu Pro Asn Gly
65                  70                  75                  80

Arg Asp Phe His Met Ser Val Val Arg Ala Gln Arg Asn Asp Ser Gly
            85                  90                  95

Thr Tyr Val Cys Gly Val Ile Ser Leu Ala Pro Lys Ile Gln Ile Lys
        100                 105                 110

Glu Ser Leu Arg Ala Glu Leu Arg Val Thr Glu Arg Arg Ala Glu Val
    115                 120                 125

Pro Thr Ala His Pro Ser Pro Ser Pro Arg Pro Ala Gly Gln Phe Gln
    130                 135                 140

Thr Leu Val Val Gly Gly Gly Gly Ser Gly Gly Gly Gly Ser Gly
145                 150                 155                 160

Gly Gly Gly Ser Phe Leu Glu Ser Pro Asp Arg Pro Trp Asn Ala Pro
            165                 170                 175

Thr Phe Ser Pro Ala Leu Leu Leu Val Ala Glu Gly Asp Asn Ala Thr
```

```
                180             185             190
Phe Thr Cys Ser Phe Ser Asn Ala Ser Glu Ser Phe His Val Val Trp
            195             200             205
His Arg Glu Ser Pro Ser Gly Gln Thr Asp Thr Leu Ala Ala Phe Pro
        210             215             220
Glu Asp Arg Ser Gln Pro Gly Gln Asp His Arg Phe Arg Val Thr Arg
225             230             235             240
Leu Pro Asn Gly Arg Asp Phe His Met Ser Val Arg Ala Gln Arg
            245             250             255
Asn Asp Ser Gly Thr Tyr Val Cys Gly Val Ile Ser Leu Ala Pro Lys
            260             265             270
Ile Gln Ile Lys Glu Ser Leu Arg Ala Glu Leu Arg Val Thr Glu Arg
        275             280             285
Arg Ala Glu Val Pro Thr Ala His Pro Ser Pro Ser Pro Arg Pro Ala
            290             295             300
Gly Gln Phe Gln Thr Leu Val Val Gly Ala Ser Gly Gly Gly Gly Ser
305             310             315             320
Gly Gly Gly Gly Ser Asp Lys Thr His Thr Cys Pro Pro Cys Pro Ala
            325             330             335
Pro Glu Ala Ala Gly Gly Pro Ser Val Phe Leu Phe Pro Pro Lys Pro
            340             345             350
Lys Asp Thr Leu Met Ile Ser Arg Thr Pro Glu Val Thr Cys Val Val
            355             360             365
Val Asp Val Ser His Glu Asp Pro Glu Val Lys Phe Asn Trp Tyr Val
        370             375             380
Asp Gly Val Glu Val His Asn Ala Lys Thr Lys Pro Arg Glu Glu Gln
385             390             395             400
Tyr Asn Ser Thr Tyr Arg Val Val Ser Val Leu Thr Val Leu His Gln
            405             410             415
Asp Trp Leu Asn Gly Lys Glu Tyr Lys Cys Ala Val Ser Asn Lys Ala
        420             425             430
Leu Pro Ala Pro Ile Glu Lys Thr Ile Ser Lys Ala Lys Gly Gln Pro
            435             440             445
Arg Glu Pro Gln Val Tyr Thr Leu Pro Pro Ser Arg Glu Glu Met Thr
        450             455             460
Lys Asn Gln Val Ser Leu Thr Cys Leu Val Lys Gly Phe Tyr Pro Ser
465             470             475             480
Asp Ile Ala Val Glu Trp Glu Ser Asn Gly Gln Pro Glu Asn Asn Tyr
            485             490             495
Lys Thr Thr Pro Pro Val Leu Asp Ser Asp Gly Ser Phe Phe Leu Tyr
            500             505             510
Ser Lys Leu Thr Val Asp Lys Ser Arg Trp Gln Gln Gly Asn Val Phe
            515             520             525
Ser Cys Ser Val Met His Glu Ala Leu His Asn His Tyr Thr Gln Lys
            530             535             540
Ser Leu Ser Leu Ser Pro Gly Gly Gly Gly Ser Gly Gly Gly Gly
545             550             555             560
Ser Gln Val Gln Leu Val Gln Ser Gly Ala Glu Val Lys Lys Pro Gly
            565             570             575
Ala Ser Val Lys Leu Ser Cys Lys Ala Ser Gly Tyr Thr Phe Ser Ser
            580             585             590
Tyr Trp Met His Trp Val Arg Gln Ala Pro Gly Gln Gly Leu Glu Trp
            595             600             605
```

Ile Gly Glu Ile Asn Pro Gly Asn Gly His Thr Asn Tyr Asn Glu Lys
610                 615                 620

Phe Lys Ser Arg Val Thr Met Thr Arg Asp Thr Ser Thr Ser Thr Ala
625                 630                 635                 640

Tyr Met Glu Leu Ser Ser Leu Arg Ser Glu Asp Thr Ala Val Tyr Tyr
            645                 650                 655

Cys Ala Arg Ser Phe Lys Thr Ala Arg Ala Phe Ala Tyr Trp Gly Gln
            660                 665                 670

Gly Thr Leu Val Thr Val Ser Ser Gly Ser Thr Ser Gly Ser Gly Lys
            675                 680                 685

Pro Gly Ser Gly Glu Gly Ser Thr Lys Gly Asp Ile Val Met Thr Gln
690                 695                 700

Ser Pro Ala Phe Leu Ser Val Thr Pro Gly Glu Lys Val Thr Ile Thr
705                 710                 715                 720

Cys Arg Ala Ser Gln Thr Ile Ser Asp Tyr Leu His Trp Tyr Gln Gln
            725                 730                 735

Lys Pro Asp Gln Ala Pro Lys Leu Leu Ile Lys Tyr Ala Ser Gln Ser
            740                 745                 750

Ile Ser Gly Ile Pro Ser Arg Phe Ser Gly Ser Gly Ser Gly Thr Asp
755                 760                 765

Phe Thr Phe Thr Ile Ser Ser Leu Glu Ala Glu Asp Ala Ala Thr Tyr
770                 775                 780

Tyr Cys Gln Asp Gly His Ser Trp Pro Pro Thr Phe Gly Gln Gly Thr
785                 790                 795                 800

Lys Leu Glu Ile Lys
            805

<210> SEQ ID NO 7
<211> LENGTH: 641
<212> TYPE: PRT
<213> ORGANISM: Artificial Sequence
<220> FEATURE:
<223> OTHER INFORMATION: Bispecific epitope binding protein S07

<400> SEQUENCE: 7

Phe Leu Glu Ser Pro Asp Arg Pro Trp Asn Ala Pro Thr Phe Ser Pro
1               5                   10                  15

Ala Leu Leu Leu Val Ala Glu Gly Asp Asn Ala Thr Phe Thr Cys Ser
            20                  25                  30

Phe Ser Asn Ala Ser Glu Ser Phe His Val Val Trp His Arg Glu Ser
        35                  40                  45

Pro Ser Gly Gln Thr Asp Thr Leu Ala Ala Phe Pro Glu Asp Arg Ser
    50                  55                  60

Gln Pro Gly Gln Asp His Arg Phe Arg Val Thr Arg Leu Pro Asn Gly
65                  70                  75                  80

Arg Asp Phe His Met Ser Val Val Arg Ala Gln Arg Asn Asp Ser Gly
                85                  90                  95

Thr Tyr Val Cys Gly Val Ile Ser Leu Ala Pro Lys Ile Gln Ile Lys
            100                 105                 110

Glu Ser Leu Arg Ala Glu Leu Arg Val Thr Glu Arg Arg Ala Glu Val
        115                 120                 125

Pro Thr Ala His Pro Ser Pro Ser Pro Arg Pro Ala Gly Gln Phe Gln
    130                 135                 140

Thr Leu Val Val Gly Ala Ser Gly Gly Gly Gly Ser Gly Gly Gly Gly
145                 150                 155                 160

```
Ser Asp Lys Thr His Thr Cys Pro Cys Pro Ala Pro Glu Ala Ala
                165                 170                 175

Gly Gly Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
    210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Ala Val Ser Asn Lys Ala Leu Pro Ala Pro
            260                 265                 270

Ile Glu Lys Thr Ile Ser Lys Ala Lys Gly Gln Pro Arg Glu Pro Gln
        275                 280                 285

Val Tyr Thr Leu Pro Pro Ser Arg Glu Glu Met Thr Lys Asn Gln Val
    290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
    370                 375                 380

Ser Pro Gly Gly Gly Gly Ser Gly Gly Gly Ser Asp Ile Val
385                 390                 395                 400

Met Thr Gln Ser Pro Ala Phe Leu Ser Val Thr Pro Gly Glu Lys Val
                405                 410                 415

Thr Ile Thr Cys Arg Ala Ser Gln Thr Ile Ser Asp Tyr Leu His Trp
            420                 425                 430

Tyr Gln Gln Lys Pro Asp Gln Ala Pro Lys Leu Leu Ile Lys Tyr Ala
        435                 440                 445

Ser Gln Ser Ile Ser Gly Ile Pro Ser Arg Phe Ser Gly Ser Gly Ser
    450                 455                 460

Gly Thr Asp Phe Thr Phe Thr Ile Ser Ser Leu Glu Ala Glu Asp Ala
465                 470                 475                 480

Ala Thr Tyr Tyr Cys Gln Asp Gly His Ser Trp Pro Pro Thr Phe Gly
                485                 490                 495

Gln Gly Thr Lys Leu Glu Ile Lys Gly Ser Thr Ser Gly Ser Gly Lys
            500                 505                 510

Pro Gly Ser Gly Glu Gly Ser Thr Lys Gly Gln Val Gln Leu Val Gln
        515                 520                 525

Ser Gly Ala Glu Val Lys Lys Pro Gly Ala Ser Val Lys Leu Ser Cys
    530                 535                 540

Lys Ala Ser Gly Tyr Thr Phe Ser Ser Tyr Trp Met His Trp Val Arg
545                 550                 555                 560

Gln Ala Pro Gly Gln Gly Leu Glu Trp Ile Gly Glu Ile Asn Pro Gly
                565                 570                 575
```

```
Asn Gly His Thr Asn Tyr Asn Glu Lys Phe Lys Ser Arg Val Thr Met
                580                 585                 590

Thr Arg Asp Thr Ser Thr Ser Thr Ala Tyr Met Glu Leu Ser Ser Leu
        595                 600                 605

Arg Ser Glu Asp Thr Ala Val Tyr Tyr Cys Ala Arg Ser Phe Lys Thr
    610                 615                 620

Ala Arg Ala Phe Ala Tyr Trp Gly Gln Gly Thr Leu Val Thr Val Ser
625                 630                 635                 640

Ser

<210> SEQ ID NO 8
<211> LENGTH: 805
<212> TYPE: PRT
<213> ORGANISM: Artificial Sequence
<220> FEATURE:
<223> OTHER INFORMATION: Bispecific epitope binding protein S08

<400> SEQUENCE: 8

Phe Leu Glu Ser Pro Asp Arg Pro Trp Asn Ala Pro Thr Phe Ser Pro
1               5                   10                  15

Ala Leu Leu Leu Val Ala Glu Gly Asp Asn Ala Thr Phe Thr Cys Ser
            20                  25                  30

Phe Ser Asn Ala Ser Glu Ser Phe His Val Val Trp His Arg Glu Ser
        35                  40                  45

Pro Ser Gly Gln Thr Asp Thr Leu Ala Ala Phe Pro Glu Asp Arg Ser
    50                  55                  60

Gln Pro Gly Gln Asp His Arg Phe Arg Val Thr Arg Leu Pro Asn Gly
65                  70                  75                  80

Arg Asp Phe His Met Ser Val Val Arg Ala Gln Arg Asn Asp Ser Gly
                85                  90                  95

Thr Tyr Val Cys Gly Val Ile Ser Leu Ala Pro Lys Ile Gln Ile Lys
            100                 105                 110

Glu Ser Leu Arg Ala Glu Leu Arg Val Thr Glu Arg Arg Ala Glu Val
        115                 120                 125

Pro Thr Ala His Pro Ser Pro Ser Pro Arg Pro Ala Gly Gln Phe Gln
    130                 135                 140

Thr Leu Val Val Gly Gly Gly Gly Ser Gly Gly Gly Gly Ser Gly
145                 150                 155                 160

Gly Gly Gly Ser Phe Leu Glu Ser Pro Asp Arg Pro Trp Asn Ala Pro
                165                 170                 175

Thr Phe Ser Pro Ala Leu Leu Leu Val Ala Glu Gly Asp Asn Ala Thr
            180                 185                 190

Phe Thr Cys Ser Phe Ser Asn Ala Ser Glu Ser Phe His Val Val Trp
        195                 200                 205

His Arg Glu Ser Pro Ser Gly Gln Thr Asp Thr Leu Ala Ala Phe Pro
    210                 215                 220

Glu Asp Arg Ser Gln Pro Gly Gln Asp His Arg Phe Arg Val Thr Arg
225                 230                 235                 240

Leu Pro Asn Gly Arg Asp Phe His Met Ser Val Val Arg Ala Gln Arg
                245                 250                 255

Asn Asp Ser Gly Thr Tyr Val Cys Gly Val Ile Ser Leu Ala Pro Lys
            260                 265                 270

Ile Gln Ile Lys Glu Ser Leu Arg Ala Glu Leu Arg Val Thr Glu Arg
        275                 280                 285

Arg Ala Glu Val Pro Thr Ala His Pro Ser Pro Ser Pro Arg Pro Ala
```

```
              290                 295                 300
Gly Gln Phe Gln Thr Leu Val Val Gly Ala Ser Gly Gly Gly Ser
305                 310                 315                 320

Gly Gly Gly Gly Ser Asp Lys Thr His Thr Cys Pro Pro Cys Pro Ala
                325                 330                 335

Pro Glu Ala Ala Gly Gly Pro Ser Val Phe Leu Phe Pro Pro Lys Pro
            340                 345                 350

Lys Asp Thr Leu Met Ile Ser Arg Thr Pro Glu Val Thr Cys Val Val
                355                 360                 365

Val Asp Val Ser His Glu Asp Pro Glu Val Lys Phe Asn Trp Tyr Val
        370                 375                 380

Asp Gly Val Glu Val His Asn Ala Lys Thr Lys Pro Arg Glu Glu Gln
385                 390                 395                 400

Tyr Asn Ser Thr Tyr Arg Val Val Ser Val Leu Thr Val Leu His Gln
                405                 410                 415

Asp Trp Leu Asn Gly Lys Glu Tyr Lys Cys Ala Val Ser Asn Lys Ala
            420                 425                 430

Leu Pro Ala Pro Ile Glu Lys Thr Ile Ser Lys Ala Lys Gly Gln Pro
        435                 440                 445

Arg Glu Pro Gln Val Tyr Thr Leu Pro Pro Ser Arg Glu Glu Met Thr
450                 455                 460

Lys Asn Gln Val Ser Leu Thr Cys Leu Val Lys Gly Phe Tyr Pro Ser
465                 470                 475                 480

Asp Ile Ala Val Glu Trp Glu Ser Asn Gly Gln Pro Glu Asn Asn Tyr
                485                 490                 495

Lys Thr Thr Pro Pro Val Leu Asp Ser Asp Gly Ser Phe Phe Leu Tyr
            500                 505                 510

Ser Lys Leu Thr Val Asp Lys Ser Arg Trp Gln Gln Gly Asn Val Phe
        515                 520                 525

Ser Cys Ser Val Met His Glu Ala Leu His Asn His Tyr Thr Gln Lys
530                 535                 540

Ser Leu Ser Leu Ser Pro Gly Gly Gly Gly Ser Gly Gly Gly Gly
545                 550                 555                 560

Ser Asp Ile Val Met Thr Gln Ser Pro Ala Phe Leu Ser Val Thr Pro
                565                 570                 575

Gly Glu Lys Val Thr Ile Thr Cys Arg Ala Ser Gln Thr Ile Ser Asp
            580                 585                 590

Tyr Leu His Trp Tyr Gln Gln Lys Pro Asp Gln Ala Pro Lys Leu Leu
        595                 600                 605

Ile Lys Tyr Ala Ser Gln Ser Ile Ser Gly Ile Pro Ser Arg Phe Ser
610                 615                 620

Gly Ser Gly Ser Gly Thr Asp Phe Thr Phe Thr Ile Ser Ser Leu Glu
625                 630                 635                 640

Ala Glu Asp Ala Ala Thr Tyr Tyr Cys Gln Asp Gly His Ser Trp Pro
                645                 650                 655

Pro Thr Phe Gly Gln Gly Thr Lys Leu Glu Ile Lys Gly Ser Thr Ser
            660                 665                 670

Gly Ser Gly Lys Pro Gly Ser Gly Glu Gly Ser Thr Lys Gly Gln Val
        675                 680                 685

Gln Leu Val Gln Ser Gly Ala Glu Val Lys Lys Pro Gly Ala Ser Val
        690                 695                 700

Lys Leu Ser Cys Lys Ala Ser Gly Tyr Thr Phe Ser Ser Tyr Trp Met
705                 710                 715                 720
```

```
His Trp Val Arg Gln Ala Pro Gly Gln Gly Leu Glu Trp Ile Gly Glu
            725                 730                 735

Ile Asn Pro Gly Asn Gly His Thr Asn Tyr Asn Glu Lys Phe Lys Ser
            740                 745                 750

Arg Val Thr Met Thr Arg Asp Thr Ser Thr Ser Thr Ala Tyr Met Glu
            755                 760                 765

Leu Ser Ser Leu Arg Ser Glu Asp Thr Ala Val Tyr Tyr Cys Ala Arg
            770                 775                 780

Ser Phe Lys Thr Ala Arg Ala Phe Ala Tyr Trp Gly Gln Gly Thr Leu
785                 790                 795                 800

Val Thr Val Ser Ser
            805
```

<210> SEQ ID NO 9
<211> LENGTH: 607
<212> TYPE: PRT
<213> ORGANISM: Artificial Sequence
<220> FEATURE:
<223> OTHER INFORMATION: Bispecific epitope binding protein S09 (HC)

<400> SEQUENCE: 9

```
Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
            35                  40                  45

Gly Glu Ile Asn Pro Gly Asn Gly His Thr Asn Tyr Asn Glu Lys Phe
        50                  55                  60

Lys Ser Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Lys Thr Ala Arg Ala Phe Ala Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Ala Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Gly Gly Gly Gly Ser Gly Gly Gly Ser Phe Leu Glu Ser Pro Asp
450                 455                 460

Arg Pro Trp Asn Ala Pro Thr Phe Ser Pro Ala Leu Leu Leu Val Ala
465                 470                 475                 480

Glu Gly Asp Asn Ala Thr Phe Thr Cys Ser Phe Ser Asn Ala Ser Glu
                485                 490                 495

Ser Phe His Val Val Trp His Arg Glu Ser Pro Ser Gly Gln Thr Asp
            500                 505                 510

Thr Leu Ala Ala Phe Pro Glu Asp Arg Ser Gln Pro Gly Gln Asp His
        515                 520                 525

Arg Phe Arg Val Thr Arg Leu Pro Asn Gly Arg Asp Phe His Met Ser
530                 535                 540

Val Val Arg Ala Gln Arg Asn Asp Ser Gly Thr Tyr Val Cys Gly Val
545                 550                 555                 560

Ile Ser Leu Ala Pro Lys Ile Gln Ile Lys Glu Ser Leu Arg Ala Glu
                565                 570                 575

Leu Arg Val Thr Glu Arg Arg Ala Glu Val Pro Thr Ala His Pro Ser
            580                 585                 590

Pro Ser Pro Arg Pro Ala Gly Gln Phe Gln Thr Leu Val Val Gly
        595                 600                 605

<210> SEQ ID NO 10
<211> LENGTH: 616
<212> TYPE: PRT
<213> ORGANISM: Artificial Sequence
<220> FEATURE:
<223> OTHER INFORMATION: Bispecific epitope binding protein S10 (HC)

<400> SEQUENCE: 10

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30
```

```
Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
 50                  55                  60

Lys Ser Arg Val Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Phe Lys Thr Ala Arg Ala Phe Ala Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Ala Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

Gly Ser Thr Ser Gly Ser Gly Lys Pro Gly Ser Gly Glu Gly Ser Thr
        450                 455                 460

Lys Gly Ser Phe Leu Glu Ser Pro Asp Arg Pro Trp Asn Ala Pro Thr
465                 470                 475                 480

Phe Ser Pro Ala Leu Leu Leu Val Ala Glu Gly Asp Asn Ala Thr Phe
                485                 490                 495

Thr Cys Ser Phe Ser Asn Ala Ser Glu Ser Phe His Val Val Trp His
                500                 505                 510

Arg Glu Ser Pro Ser Gly Gln Thr Asp Thr Leu Ala Ala Phe Pro Glu
            515                 520                 525

Asp Arg Ser Gln Pro Gly Gln Asp His Arg Phe Arg Val Thr Arg Leu
530                 535                 540

Pro Asn Gly Arg Asp Phe His Met Ser Val Val Arg Ala Gln Arg Asn
545                 550                 555                 560

Asp Ser Gly Thr Tyr Val Cys Gly Val Ile Ser Leu Ala Pro Lys Ile
                565                 570                 575

Gln Ile Lys Glu Ser Leu Arg Ala Glu Leu Arg Val Thr Glu Arg Arg
            580                 585                 590

Ala Glu Val Pro Thr Ala His Pro Ser Pro Ser Pro Arg Pro Ala Gly
                595                 600                 605

Gln Phe Gln Thr Leu Val Val Gly
        610                 615

<210> SEQ ID NO 11
<211> LENGTH: 735
<212> TYPE: PRT
<213> ORGANISM: Artificial Sequence
<220> FEATURE:
<223> OTHER INFORMATION: Peptide sequence from S11 antibody

<400> SEQUENCE: 11

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30

Leu His Trp Tyr Gln Gln Lys Pro Asp Gln Ala Pro Lys Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Trp Pro Pro
                85                  90                  95

Thr Phe Gly Gln Gly Thr Lys Leu Glu Ile Lys Gly Ser Thr Ser Gly
            100                 105                 110

Ser Gly Lys Pro Gly Ser Gly Glu Ser Thr Lys Gly Gln Val Gln
        115                 120                 125

Leu Val Gln Ser Gly Ala Glu Val Lys Lys Pro Gly Ala Ser Val Lys
130                 135                 140

Leu Ser Cys Lys Ala Ser Gly Tyr Thr Phe Ser Ser Tyr Trp Met His
145                 150                 155                 160

Trp Val Arg Gln Ala Pro Gly Gln Gly Leu Glu Trp Ile Gly Glu Ile
                165                 170                 175

Asn Pro Gly Asn Gly His Thr Asn Tyr Asn Glu Lys Phe Lys Ser Arg
            180                 185                 190

-continued

```
Val Thr Met Thr Arg Asp Thr Ser Thr Ser Thr Ala Tyr Met Glu Leu
        195                 200                 205
Ser Ser Leu Arg Ser Glu Asp Thr Ala Val Tyr Tyr Cys Ala Arg Ser
    210                 215                 220
Phe Lys Thr Ala Arg Ala Phe Ala Tyr Trp Gly Gln Gly Thr Leu Val
225                 230                 235                 240
Thr Val Ser Ser Ala Ser Gly Gly Gly Gly Ser Gly Gly Gly Gly Ser
                245                 250                 255
Asp Lys Thr His Thr Cys Pro Pro Cys Pro Ala Pro Glu Ala Ala Gly
            260                 265                 270
Gly Pro Ser Val Phe Leu Phe Pro Pro Lys Pro Lys Asp Thr Leu Met
        275                 280                 285
Ile Ser Arg Thr Pro Glu Val Thr Cys Val Val Val Asp Val Ser His
    290                 295                 300
Glu Asp Pro Glu Val Lys Phe Asn Trp Tyr Val Asp Gly Val Glu Val
305                 310                 315                 320
His Asn Ala Lys Thr Lys Pro Arg Glu Glu Gln Tyr Asn Ser Thr Tyr
                325                 330                 335
Arg Val Val Ser Val Leu Thr Val Leu His Gln Asp Trp Leu Asn Gly
            340                 345                 350
Lys Glu Tyr Lys Cys Ala Val Ser Asn Lys Ala Leu Pro Ala Pro Ile
        355                 360                 365
Glu Lys Thr Ile Ser Lys Ala Lys Gly Gln Pro Arg Glu Pro Gln Val
    370                 375                 380
Tyr Thr Leu Pro Pro Ser Arg Glu Glu Met Thr Lys Asn Gln Val Ser
385                 390                 395                 400
Leu Thr Cys Leu Val Lys Gly Phe Tyr Pro Ser Asp Ile Ala Val Glu
                405                 410                 415
Trp Glu Ser Asn Gly Gln Pro Glu Asn Asn Tyr Lys Thr Thr Pro Pro
            420                 425                 430
Val Leu Asp Ser Asp Gly Ser Phe Phe Leu Tyr Ser Lys Leu Thr Val
        435                 440                 445
Asp Lys Ser Arg Trp Gln Gln Gly Asn Val Phe Ser Cys Ser Val Met
    450                 455                 460
His Glu Ala Leu His Asn His Tyr Thr Gln Lys Ser Leu Ser Leu Ser
465                 470                 475                 480
Pro Gly Gly Gly Gly Ser Gly Gly Gly Gly Ser Glu Val Gln Leu
                485                 490                 495
Val Glu Ser Gly Gly Gly Leu Val Gln Pro Gly Gly Ser Leu Arg Leu
            500                 505                 510
Ser Cys Ala Ala Ser Gly Phe Thr Phe Ser Asp Ser Trp Ile His Trp
        515                 520                 525
Val Arg Gln Ala Pro Gly Lys Gly Leu Glu Trp Val Ala Trp Ile Ser
    530                 535                 540
Pro Tyr Gly Gly Ser Thr Tyr Tyr Ala Asp Ser Val Lys Gly Arg Phe
545                 550                 555                 560
Thr Ile Ser Ala Asp Thr Ser Lys Asn Thr Ala Tyr Leu Gln Met Asn
                565                 570                 575
Ser Leu Arg Ala Glu Asp Thr Ala Val Tyr Tyr Cys Ala Arg Arg His
            580                 585                 590
Trp Pro Gly Gly Phe Asp Tyr Trp Gly Gln Gly Thr Leu Val Thr Val
        595                 600                 605
Ser Ser Gly Ser Thr Ser Gly Ser Gly Lys Pro Gly Ser Gly Glu Gly
```

```
            610                 615                 620
Ser Thr Lys Gly Asp Ile Gln Met Thr Gln Ser Pro Ser Ser Leu Ser
625                 630                 635                 640

Ala Ser Val Gly Asp Arg Val Thr Ile Thr Cys Arg Ala Ser Gln Asp
                645                 650                 655

Val Ser Thr Ala Val Ala Trp Tyr Gln Gln Lys Pro Gly Lys Ala Pro
                660                 665                 670

Lys Leu Leu Ile Tyr Ser Ala Ser Phe Leu Tyr Ser Gly Val Pro Ser
            675                 680                 685

Arg Phe Ser Gly Ser Gly Ser Gly Thr Asp Phe Thr Leu Thr Ile Ser
        690                 695                 700

Ser Leu Gln Pro Glu Asp Phe Ala Thr Tyr Tyr Cys Gln Gln Tyr Leu
705                 710                 715                 720

Tyr His Pro Ala Thr Phe Gly Gln Gly Thr Lys Val Glu Ile Lys
                725                 730                 735

<210> SEQ ID NO 12
<211> LENGTH: 639
<212> TYPE: PRT
<213> ORGANISM: Artificial Sequence
<220> FEATURE:
<223> OTHER INFORMATION: Bispecific antigen binding protein S12

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Gly Ser Thr Ser
            100                 105                 110

Gly Ser Gly Lys Pro Gly Ser Gly Glu Gly Ser Thr Lys Gly Glu Val
        115                 120                 125

Gln Leu Leu Glu Ser Gly Gly Gly Leu Val Gln Pro Gly Gly Ser Leu
    130                 135                 140

Arg Leu Ser Cys Ala Ala Ser Gly Phe Thr Phe Ser Ser Tyr Ala Met
145                 150                 155                 160

Ser Trp Val Arg Gln Ala Pro Gly Lys Gly Leu Glu Trp Val Ser Ala
                165                 170                 175

Ile Ser Gly Ser Gly Gly Ser Thr Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Ala Lys
    210                 215                 220

Pro Phe Pro Tyr Phe Asp Tyr Trp Gly Gln Gly Thr Leu Val Thr Val
225                 230                 235                 240

Ser Ser Ala Ser Gly Gly Gly Gly Ser Gly Gly Gly Gly Ser Asp Lys
```

```
                    245                 250                 255
Thr His Thr Cys Pro Cys Pro Ala Pro Glu Ala Ala Gly Gly Pro
                260                 265                 270

Ser Val Phe Leu Phe Pro Pro Lys Pro Lys Asp Thr Leu Met Ile Ser
                275                 280                 285

Arg Thr Pro Glu Val Thr Cys Val Val Val Asp Val Ser His Glu Asp
            290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Ala Val Ser Asn Lys Ala Leu Pro Ala Pro Ile Glu Lys
                355                 360                 365

Thr Ile Ser Lys Ala Lys Gly Gln Pro Arg Glu Pro Gln Val Tyr Thr
            370                 375                 380

Leu Pro Pro Ser Arg Glu Glu Met Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
            435                 440                 445

Ser Arg Trp Gln Gln Gly Asn Val Phe Ser Cys Ser Val Met His Glu
        450                 455                 460

Ala Leu His Asn His Tyr Thr Gln Lys Ser Leu Ser Leu Ser Pro Gly
465                 470                 475                 480

Gly Gly Gly Gly Ser Gly Gly Gly Ser Phe Leu Glu Ser Pro Asp
                485                 490                 495

Arg Pro Trp Asn Ala Pro Thr Phe Ser Pro Ala Leu Leu Val Val Ala
            500                 505                 510

Glu Gly Asp Asn Ala Thr Phe Thr Cys Ser Phe Ser Asn Ala Ser Glu
        515                 520                 525

Ser Phe His Val Val Trp His Arg Glu Ser Pro Ser Gly Gln Thr Asp
        530                 535                 540

Thr Leu Ala Ala Phe Pro Glu Asp Arg Ser Gln Pro Gly Gln Asp His
545                 550                 555                 560

Arg Phe Arg Val Thr Arg Leu Pro Asn Gly Arg Asp Phe His Met Ser
                565                 570                 575

Val Val Arg Ala Gln Arg Asn Asp Ser Gly Thr Tyr Val Cys Gly Val
            580                 585                 590

Ile Ser Leu Ala Pro Lys Ile Gln Ile Lys Glu Ser Leu Arg Ala Glu
                595                 600                 605

Leu Arg Val Thr Glu Arg Arg Ala Glu Val Pro Thr Ala His Pro Ser
        610                 615                 620

Pro Ser Pro Arg Pro Ala Gly Gln Phe Gln Thr Leu Val Val Gly
625                 630                 635

<210> SEQ ID NO 13
<211> LENGTH: 641
<212> TYPE: PRT
<213> ORGANISM: Artificial Sequence
```

<220> FEATURE:
<223> OTHER INFORMATION: Bispecific epitope binding protein S13

<400> SEQUENCE: 13

| | | | | | | | | | | | | | | |
|---|---|---|---|---|---|---|---|---|---|---|---|---|---|---|
| Asp | Ile | Val | Met | Thr | Gln | Ser | Pro | Ala | Phe | Leu | Ser | Val | Thr | Pro | Gly |
| 1 | | | | 5 | | | | | 10 | | | | | 15 | |
| Glu | Lys | Val | Thr | Ile | Thr | Cys | Arg | Ala | Ser | Gln | Thr | Ile | Ser | Asp | Tyr |
| | | | 20 | | | | | 25 | | | | | 30 | | |
| Leu | His | Trp | Tyr | Gln | Gln | Lys | Pro | Asp | Gln | Ala | Pro | Lys | Leu | Leu | Ile |
| | | | 35 | | | | | 40 | | | | | 45 | | |
| Lys | Tyr | Ala | Ser | Gln | Ser | Ile | Ser | Gly | Ile | Pro | Ser | Arg | Phe | Ser | Gly |
| | | | 50 | | | | | 55 | | | | | 60 | | |
| Ser | Gly | Ser | Gly | Thr | Asp | Phe | Thr | Phe | Thr | Ile | Ser | Ser | Leu | Glu | Ala |
| 65 | | | | | 70 | | | | | 75 | | | | | 80 |
| Glu | Asp | Ala | Ala | Thr | Tyr | Tyr | Cys | Gln | Asp | Gly | His | Ser | Trp | Pro | Pro |
| | | | | 85 | | | | | 90 | | | | | 95 | |
| Thr | Phe | Gly | Gln | Gly | Thr | Lys | Leu | Glu | Ile | Lys | Gly | Ser | Thr | Ser | Gly |
| | | | | 100 | | | | | 105 | | | | | 110 | |
| Ser | Gly | Lys | Pro | Gly | Ser | Gly | Glu | Gly | Ser | Thr | Lys | Gly | Gln | Val | Gln |
| | | | 115 | | | | | 120 | | | | | 125 | | |
| Leu | Val | Gln | Ser | Gly | Ala | Glu | Val | Lys | Lys | Pro | Gly | Ala | Ser | Val | Lys |
| | | 130 | | | | | 135 | | | | | 140 | | | |
| Leu | Ser | Cys | Lys | Ala | Ser | Gly | Tyr | Thr | Phe | Ser | Ser | Tyr | Trp | Met | His |
| 145 | | | | | 150 | | | | | 155 | | | | | 160 |
| Trp | Val | Arg | Gln | Ala | Pro | Gly | Gln | Gly | Leu | Glu | Trp | Ile | Gly | Glu | Ile |
| | | | | 165 | | | | | 170 | | | | | 175 | |
| Asn | Pro | Gly | Asn | Gly | His | Thr | Asn | Tyr | Asn | Glu | Lys | Phe | Lys | Ser | Arg |
| | | | | 180 | | | | | 185 | | | | | 190 | |
| Val | Thr | Met | Thr | Arg | Asp | Thr | Ser | Thr | Ser | Thr | Ala | Tyr | Met | Glu | Leu |
| | | | 195 | | | | | 200 | | | | | 205 | | |
| Ser | Ser | Leu | Arg | Ser | Glu | Asp | Thr | Ala | Val | Tyr | Tyr | Cys | Ala | Arg | Ser |
| | | 210 | | | | | 215 | | | | | 220 | | | |
| Phe | Lys | Thr | Ala | Arg | Ala | Phe | Ala | Tyr | Trp | Gly | Gln | Gly | Thr | Leu | Val |
| 225 | | | | | 230 | | | | | 235 | | | | | 240 |
| Thr | Val | Ser | Ser | Ala | Ser | Gly | Gly | Gly | Gly | Ser | Gly | Gly | Gly | Gly | Ser |
| | | | | 245 | | | | | 250 | | | | | 255 | |
| Asp | Lys | Thr | His | Thr | Cys | Pro | Pro | Cys | Pro | Ala | Pro | Glu | Ala | Ala | Gly |
| | | | | 260 | | | | | 265 | | | | | 270 | |
| Gly | Pro | Ser | Val | Phe | Leu | Phe | Pro | Pro | Lys | Pro | Lys | Asp | Thr | Leu | Met |
| | | | 275 | | | | | 280 | | | | | 285 | | |
| Ile | Ser | Arg | Thr | Pro | Glu | Val | Thr | Cys | Val | Val | Val | Asp | Val | Ser | His |
| | | | 290 | | | | | 295 | | | | | 300 | | |
| Glu | Asp | Pro | Glu | Val | Lys | Phe | Asn | Trp | Tyr | Val | Asp | Gly | Val | Glu | Val |
| 305 | | | | | 310 | | | | | 315 | | | | | 320 |
| His | Asn | Ala | Lys | Thr | Lys | Pro | Arg | Glu | Glu | Gln | Tyr | Asn | Ser | Thr | Tyr |
| | | | | 325 | | | | | 330 | | | | | 335 | |
| Arg | Val | Val | Ser | Val | Leu | Thr | Val | Leu | His | Gln | Asp | Trp | Leu | Asn | Gly |
| | | | 340 | | | | | 345 | | | | | 350 | | |
| Lys | Glu | Tyr | Lys | Cys | Ala | Val | Ser | Asn | Lys | Ala | Leu | Pro | Ala | Pro | Ile |
| | | | | 355 | | | | | 360 | | | | | 365 | |
| Glu | Lys | Thr | Ile | Ser | Lys | Ala | Lys | Gly | Gln | Pro | Arg | Glu | Pro | Gln | Val |
| | | | 370 | | | | | 375 | | | | | 380 | | |
| Tyr | Thr | Leu | Pro | Pro | Ser | Arg | Glu | Glu | Met | Thr | Lys | Asn | Gln | Val | Ser |
| 385 | | | | | 390 | | | | | 395 | | | | | 400 |

```
Leu Thr Cys Leu Val Lys Gly Phe Tyr Pro Ser Asp Ile Ala Val Glu
            405                 410                 415

Trp Glu Ser Asn Gly Gln Pro Glu Asn Asn Tyr Lys Thr Thr Pro Pro
        420                 425                 430

Val Leu Asp Ser Asp Gly Ser Phe Phe Leu Tyr Ser Lys Leu Thr Val
            435                 440                 445

Asp Lys Ser Arg Trp Gln Gln Gly Asn Val Phe Ser Cys Ser Val Met
        450                 455                 460

His Glu Ala Leu His Asn His Tyr Thr Gln Lys Ser Leu Ser Leu Ser
465                 470                 475                 480

Pro Gly Gly Gly Gly Ser Gly Gly Gly Ser Phe Leu Glu Ser
            485                 490                 495

Pro Asp Arg Pro Trp Asn Ala Pro Thr Phe Ser Pro Ala Leu Leu Leu
        500                 505                 510

Val Ala Glu Gly Asp Asn Ala Thr Phe Thr Cys Ser Phe Ser Asn Ala
            515                 520                 525

Ser Glu Ser Phe His Val Val Trp His Arg Glu Ser Pro Ser Gly Gln
        530                 535                 540

Thr Asp Ala Leu Ala Ala Phe Pro Glu Asp Arg Ser Gln Pro Gly Gln
545                 550                 555                 560

Asp His Arg Phe Arg Val Thr Arg Leu Pro Asn Gly Arg Asp Phe His
            565                 570                 575

Met Ser Val Val Arg Ala Gln Arg Asn Asp Ser Gly Thr Tyr Val Cys
        580                 585                 590

Gly Val Ala Ser Leu Ala Pro Lys Ile Gln Ala Lys Glu Ser Leu Arg
            595                 600                 605

Ala Glu Leu Arg Val Thr Glu Arg Arg Ala Glu Val Pro Thr Ala His
        610                 615                 620

Pro Ser Pro Ser Pro Arg Pro Ala Gly Gln Phe Gln Thr Leu Val Val
625                 630                 635                 640

Gly

<210> SEQ ID NO 14
<211> LENGTH: 234
<212> TYPE: PRT
<213> ORGANISM: Artificial Sequence
<220> FEATURE:
<223> OTHER INFORMATION: LC of S09, S10, 94kvt-engineered IgG1

<400> SEQUENCE: 14

Met Asp Ser Gln Ala Gln Val Leu Met Leu Leu Leu Leu Ser Val Ser
1               5                   10                  15

Gly Thr Cys Gly Asp Ile Val Met Thr Gln Ser Pro Ala Phe Leu Ser
            20                  25                  30

Val Thr Pro Gly Glu Lys Val Thr Ile Thr Cys Arg Ala Ser Gln Thr
        35                  40                  45

Ile Ser Asp Tyr Leu His Trp Tyr Gln Gln Lys Pro Asp Gln Ala Pro
    50                  55                  60

Lys Leu Leu Ile Lys Tyr Ala Ser Gln Ser Ile Ser Gly Ile Pro Ser
65                  70                  75                  80

Arg Phe Ser Gly Ser Gly Ser Gly Thr Asp Phe Thr Phe Thr Ile Ser
            85                  90                  95

Ser Leu Glu Ala Glu Asp Ala Ala Thr Tyr Tyr Cys Gln Asp Gly His
            100                 105                 110
```

Ser Trp Pro Pro Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 15
<211> LENGTH: 15
<212> TYPE: PRT
<213> ORGANISM: Artificial Sequence
<220> FEATURE:
<223> OTHER INFORMATION: (G4S)3 peptide linker

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 10
<212> TYPE: PRT
<213> ORGANISM: Artificial Sequence
<220> FEATURE:
<223> OTHER INFORMATION: (G4S)2 peptide linker

<400> SEQUENCE: 16

Gly Gly Gly Gly Ser Gly Gly Gly Gly Ser
1               5                   10

<210> SEQ ID NO 17
<211> LENGTH: 18
<212> TYPE: PRT
<213> ORGANISM: Artificial Sequence
<220> FEATURE:
<223> OTHER INFORMATION: 218 peptide linker

<400> SEQUENCE: 17

Gly Ser Thr Ser Gly Ser Gly Lys Pro Gly Ser Gly Glu Gly Ser Thr
1               5                   10                  15

Lys Gly

<210> SEQ ID NO 18
<211> LENGTH: 19
<212> TYPE: PRT
<213> ORGANISM: Artificial Sequence
<220> FEATURE:
<223> OTHER INFORMATION: 218S peptide linker

<400> SEQUENCE: 18

Gly Ser Thr Ser Gly Ser Gly Lys Pro Gly Ser Gly Glu Gly Ser Thr
1               5                   10                  15

Lys Gly Ser

```
<210> SEQ ID NO 19
<211> LENGTH: 288
<212> TYPE: PRT
<213> ORGANISM: Homo sapiens
<220> FEATURE:
<221> NAME/KEY: MISC_FEATURE
<222> LOCATION: (1)..(288)
<223> OTHER INFORMATION: Wild type PD-1

<400> SEQUENCE: 19
```

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

```
<210> SEQ ID NO 20
<211> LENGTH: 449
<212> TYPE: PRT
<213> ORGANISM: Artificial Sequence
<220> FEATURE:
<223> OTHER INFORMATION: HC of 94 kvt-IgG1

<400> SEQUENCE: 20
```

Gln Val Gln Leu Val Gln Ser Gly Ala Glu Val Lys Lys Pro Gly Ala
1               5                   10                  15

```
Ser Val Lys Leu Ser Cys Lys Ala Ser Gly Tyr Thr Phe Ser Ser Tyr
         20                  25                  30
Trp Met His Trp Val Arg Gln Ala Pro Gly Gln Gly Leu Glu Trp Ile
         35                  40                  45
Gly Glu Ile Asn Pro Gly Asn Gly His Thr Asn Tyr Asn Glu Lys Phe
 50                  55                  60
Lys Ser Arg Val Thr Met Thr Arg Asp Thr Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ser Phe Lys Thr Ala Arg Ala Phe Ala Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
```

```
Ala Leu His Asn His Tyr Thr Gln Lys Ser Leu Ser Leu Ser Pro Gly
            435                 440                 445

Lys

<210> SEQ ID NO 21
<211> LENGTH: 449
<212> TYPE: PRT
<213> ORGANISM: Artificial Sequence
<220> FEATURE:
<223> OTHER INFORMATION: HC of 94kvt-engineered IgG1 (Anti-4-1BB
      antibody)

<400> SEQUENCE: 21

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
    50                  55                  60

Lys Ser Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Lys Thr Ala Arg Ala Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Ala Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 22
<211> LENGTH: 394
<212> TYPE: PRT
<213> ORGANISM: Artificial Sequence
<220> FEATURE:
<223> OTHER INFORMATION: euPD-1 Fc

<400> SEQUENCE: 22

Phe Leu Glu Ser Pro Asp Arg Pro Trp Asn Ala Pro Thr Phe Ser Pro
1               5                   10                  15

Ala Leu Leu Leu Val Ala Glu Gly Asp Asn Ala Thr Phe Thr Cys Ser
            20                  25                  30

Phe Ser Asn Ala Ser Glu Ser Phe His Val Val Trp His Arg Glu Ser
        35                  40                  45

Pro Ser Gly Gln Thr Asp Thr Leu Ala Ala Phe Pro Glu Asp Arg Ser
    50                  55                  60

Gln Pro Gly Gln Asp His Arg Phe Arg Val Thr Arg Leu Pro Asn Gly
65                  70                  75                  80

Arg Asp Phe His Met Ser Val Val Arg Ala Gln Arg Asn Asp Ser Gly
                85                  90                  95

Thr Tyr Val Cys Gly Val Ile Ser Leu Ala Pro Lys Ile Gln Ile Lys
            100                 105                 110

Glu Ser Leu Arg Ala Glu Leu Arg Val Thr Glu Arg Arg Ala Glu Val
        115                 120                 125

Pro Thr Ala His Pro Ser Pro Ser Pro Arg Pro Ala Gly Gln Phe Gln
    130                 135                 140

Thr Leu Val Val Gly Gly Gly Gly Ser Ser Asn Thr Lys Val Asp
145                 150                 155                 160

Lys Arg Val Glu Pro Lys Ser Cys Asp Lys Thr His Thr Cys Pro Pro
                165                 170                 175

Cys Pro Ala Pro Pro Val Ala Gly Pro Ser Val Phe Leu Phe Pro Pro
            180                 185                 190

Lys Pro Lys Asp Thr Leu Met Ile Ser Arg Thr Pro Glu Val Thr Cys
        195                 200                 205

Val Val Val Asp Val Ser His Glu Asp Pro Glu Val Gln Phe Asn Trp
    210                 215                 220

Tyr Val Asp Gly Val Glu Val His Asn Ala Lys Thr Lys Pro Arg Glu
225                 230                 235                 240

Glu Gln Phe Asn Ser Thr Phe Arg Val Val Ser Val Leu Thr Val Val
```

```
                    245                 250                 255
His Gln Asp Trp Leu Asn Gly Lys Glu Tyr Lys Cys Lys Val Ser Asn
                260                 265                 270

Lys Gly Leu Pro Ala Pro Ile Glu Lys Thr Ile Ser Lys Thr Lys Gly
            275                 280                 285

Gln Pro Arg Glu Pro Gln Val Tyr Thr Leu Pro Pro Ser Arg Glu Glu
        290                 295                 300

Met Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Met Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
    370                 375                 380

Gln Lys Ser Leu Ser Leu Ser Pro Gly Lys
385                 390

<210> SEQ ID NO 23
<211> LENGTH: 119
<212> TYPE: PRT
<213> ORGANISM: Artificial Sequence
<220> FEATURE:
<223> OTHER INFORMATION: VH peptide sequence

<400> SEQUENCE: 23

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
    50                  55                  60

Lys Ser Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Lys Thr Ala Arg Ala Phe Ala Tyr Trp Gly Gln Gly
            100                 105                 110

Thr Leu Val Thr Val Ser Ser
        115

<210> SEQ ID NO 24
<211> LENGTH: 357
<212> TYPE: DNA
<213> ORGANISM: Artificial Sequence
<220> FEATURE:
<223> OTHER INFORMATION: VH nucleic acid sequence

<400> SEQUENCE: 24
caggtccagc tggtgcagag cggcgccgaa gtgaaaaaac ctggggcaag tgtcaagctg    60
tcctgtaagg ccagcggtta taccttctcc tcatattgga tgcactgggt gaggcaagcc   120
cctggacaag ggctggaatg gatcggtgaa attaatcccg gaaatggcca tacaaactac   180
```

```
aatgaaaaat tcaaaagtcg agtgaccatg acacgggaca catccacttc cactgcatac    240
atggagcttt cgagtctgcg ctccgaggat acagctgtct attactgcgc acgcagtttt    300
aaaactgcca gagcctttgc ctactggggt cagggaaccc tggtcaccgt tagcagc       357

<210> SEQ ID NO 25
<211> LENGTH: 107
<212> TYPE: PRT
<213> ORGANISM: Artificial Sequence
<220> FEATURE:
<223> OTHER INFORMATION: VL peptide sequence

<400> SEQUENCE: 25

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30

Leu His Trp Tyr Gln Gln Lys Pro Asp Gln Ala Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Trp Pro Pro
                85                  90                  95

Thr Phe Gly Gln Gly Thr Lys Leu Glu Ile Lys
            100                 105

<210> SEQ ID NO 26
<211> LENGTH: 321
<212> TYPE: DNA
<213> ORGANISM: Artificial Sequence
<220> FEATURE:
<223> OTHER INFORMATION: VL nucleic acid sequence

<400> SEQUENCE: 26
gacattgtga tgacacagtc ccctgctttc ctgagcgtta cacccggcga aaaggtgact    60
atcacatgca gggctagtca gaccatctca gactaccttc attggtatca acagaagcca    120
gaccaggctc ctaagttgct gataaagtac gcctcccaat ccatttccgg cattccttcc    180 cgttttccg  gctccggctc cggcaccgac tttacgttca ccatctcttc tttggaggct    240
gaagacgcag ctacctatta ctgtcaggat ggtcacagct ggccaccaac tttcgggcaa    300
ggcaccaagc tggagatcaa a                                              321

<210> SEQ ID NO 27
<211> LENGTH: 149
<212> TYPE: PRT
<213> ORGANISM: Artificial Sequence
<220> FEATURE:
<223> OTHER INFORMATION: euPD-1 peptide sequence

<400> SEQUENCE: 27

Phe Leu Glu Ser Pro Asp Arg Pro Trp Asn Ala Pro Thr Phe Ser Pro
1               5                   10                  15

Ala Leu Leu Leu Val Ala Glu Gly Asp Asn Ala Thr Phe Thr Cys Ser
            20                  25                  30

Phe Ser Asn Ala Ser Glu Ser Phe His Val Val Trp His Arg Glu Ser
        35                  40                  45

Pro Ser Gly Gln Thr Asp Thr Leu Ala Ala Phe Pro Glu Asp Arg Ser
```

```
                50                  55                  60
Gln Pro Gly Gln Asp His Arg Phe Arg Val Thr Arg Leu Pro Asn Gly
 65                  70                  75                  80

Arg Asp Phe His Met Ser Val Val Arg Ala Gln Arg Asn Asp Ser Gly
                 85                  90                  95

Thr Tyr Val Cys Gly Val Ile Ser Leu Ala Pro Lys Ile Gln Ile Lys
            100                 105                 110

Glu Ser Leu Arg Ala Glu Leu Arg Val Thr Glu Arg Arg Ala Glu Val
        115                 120                 125

Pro Thr Ala His Pro Ser Pro Ser Pro Arg Pro Ala Gly Gln Phe Gln
    130                 135                 140

Thr Leu Val Val Gly
145

<210> SEQ ID NO 28
<211> LENGTH: 447
<212> TYPE: DNA
<213> ORGANISM: Artificial Sequence
<220> FEATURE:
<223> OTHER INFORMATION: euPD-1 nucleic acid sequence

<400> SEQUENCE: 28
tttctcgaat caccggacag accctggaat gcgcccacat tctcaccagc acttttgctg      60
gtagcagagg gcgataatgc tacattcacg tgttccttca gtaatgcaag cgagtcattt     120
catgtggttt ggcatcgaga gtcacctagt gggcagactg atacacttgc cgcattcccg     180
gaagatcgct cccagccagg tcaggatcac cggttcaggg taacccgact gccgaatggg     240
cgcgatttcc atatgagcgt tgtccgggcg caacggaacg atagtggaac atacgtgtgt     300
ggcgtaatat ccctcgctcc caaaatacaa ataaggagt ctctgagagc agagctgaga      360
gtgacagaac gacgggcgga agttcccacg gctcatccgt caccaagtcc gcgccccgca     420
ggccaatttc aaacgctcgt cgtaggc                                        447

<210> SEQ ID NO 29
<211> LENGTH: 17
<212> TYPE: PRT
<213> ORGANISM: Artificial Sequence
<220> FEATURE:
<223> OTHER INFORMATION: Signal peptide

<400> SEQUENCE: 29

Met Glu Trp Ser Trp Val Phe Leu Val Thr Leu Leu Asn Gly Ile Gln
 1               5                  10                  15

Cys

<210> SEQ ID NO 30
<211> LENGTH: 15
<212> TYPE: PRT
<213> ORGANISM: Artificial Sequence
<220> FEATURE:
<223> OTHER INFORMATION: Hinge peptide

<400> SEQUENCE: 30

Glu Pro Lys Ser Cys Asp Lys Thr His Thr Cys Pro Pro Cys Pro
 1               5                  10                  15

<210> SEQ ID NO 31
<211> LENGTH: 10
<212> TYPE: PRT
<213> ORGANISM: Artificial Sequence
```

<220> FEATURE:
<223> OTHER INFORMATION: Hinge peptide

<400> SEQUENCE: 31

Asp Lys Thr His Thr Cys Pro Pro Cys Pro
1               5                   10

<210> SEQ ID NO 32
<211> LENGTH: 330
<212> TYPE: PRT
<213> ORGANISM: Artificial Sequence
<220> FEATURE:
<223> OTHER INFORMATION: CH domain (IgG1)

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys

```
                      325                 330

<210> SEQ ID NO 33
<211> LENGTH: 329
<212> TYPE: PRT
<213> ORGANISM: Artificial Sequence
<220> FEATURE:
<223> OTHER INFORMATION: Modified CH domain

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 34
<211> LENGTH: 326
<212> TYPE: PRT
```

<213> ORGANISM: Artificial Sequence
<220> FEATURE:
<223> OTHER INFORMATION: CH domain (IgG2)

<400> SEQUENCE: 34

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 35
<211> LENGTH: 377
<212> TYPE: PRT
<213> ORGANISM: Artificial Sequence
<220> FEATURE:
<223> OTHER INFORMATION: CH domain (IgG3)

<400> SEQUENCE: 35

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
            130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 36
<211> LENGTH: 327
<212> TYPE: PRT
<213> ORGANISM: Artificial Sequence
<220> FEATURE:
<223> OTHER INFORMATION: CH domain (IgG4)

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 37
<211> LENGTH: 107
<212> TYPE: PRT
<213> ORGANISM: Artificial Sequence
<220> FEATURE:
<223> OTHER INFORMATION: CL domain (Immunoglobin kappa)

<400> SEQUENCE: 37

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 38
<211> LENGTH: 106
<212> TYPE: PRT
<213> ORGANISM: Artificial Sequence
<220> FEATURE:
<223> OTHER INFORMATION: CL domain (Immunoglobin lambda 1)

<400> SEQUENCE: 38

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Gly Ser Pro
            35                  40                  45

Val Lys Ala Gly Val Glu Thr Thr Lys Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 39
<211> LENGTH: 106
<212> TYPE: PRT
<213> ORGANISM: Artificial Sequence
<220> FEATURE:
<223> OTHER INFORMATION: CL domain (immunoglobin lambda 2)

<400> SEQUENCE: 39

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

-continued

```
Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```